US006846448B2

(12) United States Patent
Rymer et al.

(10) Patent No.: US 6,846,448 B2
(45) Date of Patent: Jan. 25, 2005

(54) METHOD AND APPARATUS FOR MAKING ON-LINE STABILIZED ABSORBENT MATERIALS

(75) Inventors: Timothy James Rymer, Appleton, WI (US); Michael Barth Venturino, Appleton, WI (US); Mark Scott Lancaster, Neenah, WI (US); Robert Eugene Vogt, Neenah, WI (US); Dennis John DeGroot, Appleton, WI (US); Michael Joseph Garvey, Appleton, WI (US); James Alvin Boldra, Menasha, WI (US); Frank Paul Abuto, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 313 days.

(21) Appl. No.: 10/037,385

(22) Filed: Dec. 20, 2001

(65) Prior Publication Data

US 2003/0116888 A1 Jun. 26, 2003

(51) Int. Cl.⁷ .................................................. B27N 3/04
(52) U.S. Cl. ...................................... 264/460; 264/122
(58) Field of Search ................................. 264/460, 122

(56) References Cited

U.S. PATENT DOCUMENTS

| 3,759,775 A | 9/1973 | Shepherd |
| 3,802,817 A | 4/1974 | Matsuki et al. |
| 3,803,453 A | 4/1974 | Hull |
| 3,849,241 A | 11/1974 | Butin et al. |
| 3,860,002 A | 1/1975 | Kolbach |
| 3,901,236 A | 8/1975 | Assarsson et al. |
| 4,016,628 A | 4/1977 | Kolbach |
| 4,076,663 A | 2/1978 | Masuda et al. |
| 4,100,324 A | 7/1978 | Anderson et al. |
| RE29,789 E | 10/1978 | Kolbach |
| 4,186,165 A | 1/1980 | Aberson et al. |
| 4,286,082 A | 8/1981 | Tsubakimoto et al. |
| 4,297,410 A | 10/1981 | Tsuchiya et al. |
| 4,309,479 A | 1/1982 | Naruse et al. |
| 4,340,563 A | 7/1982 | Appel et al. |
| 4,375,448 A | 3/1983 | Appel et al. |

(List continued on next page.)

FOREIGN PATENT DOCUMENTS

| DE | 4024053 A1 | 1/1992 |
| EP | 0 345 523 A1 | 5/1989 |

(List continued on next page.)

OTHER PUBLICATIONS

Patent Abstracts of Japan 05263318: Description of Nakamura Eiichiro/Kuraray Co. Ltd., "Electrically Conductive Conjugate Fiber."

(List continued on next page.)

*Primary Examiner*—Mary Lynn Theisen
(74) *Attorney, Agent, or Firm*—Paul Y. Yee; Thomas M. Parker

(57) ABSTRACT

A method for forming a stabilized airlaid layer (86) can include an airforming of a substantially unbonded fibrous layer (66) which includes absorbent fibers and binder-fibers. The fibrous layer (66) is exposed to high-frequency electromagnetic energy during a distinctively short activation period to activate the binder-fibers to provide the stabilized, airlaid layer (86). In a particular aspect the activation period can be not more than about 3 sec.

20 Claims, 33 Drawing Sheets

U.S. PATENT DOCUMENTS

| | | |
|---|---|---|
| 4,392,908 A | 7/1983 | Dehnel |
| 4,401,708 A | 8/1983 | Paul |
| 4,429,001 A | 1/1984 | Kolpin et al. |
| 4,494,278 A | 1/1985 | Kroyer et al. |
| 4,530,353 A | 7/1985 | Lauritzen |
| 4,542,199 A | 9/1985 | Kaminsky et al. |
| 4,640,810 A | 2/1987 | Laursen et al. |
| 4,663,220 A | 5/1987 | Wisneski et al. |
| 4,666,647 A | 5/1987 | Enloe et al. |
| 4,674,966 A | 6/1987 | Johnson et al. |
| 4,704,116 A | 11/1987 | Enloe |
| 4,721,647 A | 1/1988 | Nakanishi et al. |
| 4,725,448 A | 2/1988 | Fitzpatrick |
| 4,743,505 A | 5/1988 | Yamada et al. |
| 4,755,178 A | 7/1988 | Insley et al. |
| 4,756,969 A | 7/1988 | Takeda |
| 4,761,258 A | 8/1988 | Enloe |
| 4,767,825 A | 8/1988 | Pazos et al. |
| 4,786,915 A | 11/1988 | Cartwright et al. |
| 4,795,668 A | 1/1989 | Krueger et al. |
| 4,798,603 A | 1/1989 | Meyer et al. |
| 4,813,948 A | 3/1989 | Insley |
| 4,818,315 A | 4/1989 | Hellgren et al. |
| 4,818,464 A | 4/1989 | Lau |
| 4,921,645 A | 5/1990 | Insley |
| 4,927,582 A | 5/1990 | Bryson |
| 4,939,016 A | 7/1990 | Radwanski et al. |
| 5,002,814 A | 3/1991 | Knack et al. |
| 5,057,368 A | 10/1991 | Largman et al. |
| 5,064,802 A | 11/1991 | Stevens et al. |
| 5,069,970 A | 12/1991 | Largman et al. |
| 5,108,820 A | 4/1992 | Kaneko et al. |
| 5,108,827 A | 4/1992 | Gessner |
| 5,139,861 A | 8/1992 | Williams et al. |
| 5,143,680 A | 9/1992 | Molnar et al. |
| 5,147,343 A | 9/1992 | Kellenberger |
| 5,148,172 A | 9/1992 | Kumurdjian |
| 5,155,316 A | 10/1992 | Chiu |
| 5,176,668 A | 1/1993 | Bernardin |
| 5,176,672 A | 1/1993 | Bruemmer et al. |
| 5,185,506 A | 2/1993 | Walters |
| 5,188,624 A | 2/1993 | Young, Sr. et al. |
| 5,192,606 A | 3/1993 | Proxmire et al. |
| 5,217,768 A | 6/1993 | Walters et al. |
| 5,220,143 A | 6/1993 | Kemske et al. |
| 5,226,992 A | 7/1993 | Morman |
| 5,230,959 A | 7/1993 | Young, Sr. et al. |
| 5,246,770 A | 9/1993 | Bottiglione et al. |
| 5,254,821 A | 10/1993 | Walters |
| 5,277,976 A | 1/1994 | Hogle et al. |
| 5,294,482 A | 3/1994 | Gessner |
| 5,304,161 A | 4/1994 | Noel et al. |
| 5,318,650 A | 6/1994 | Kerawalla |
| 5,334,446 A | 8/1994 | Quantrille et al. |
| 5,336,552 A | 8/1994 | Strack et al. |
| 5,350,904 A | 9/1994 | Kemske et al. |
| 5,368,918 A | 11/1994 | Harada et al. |
| 5,374,696 A | 12/1994 | Rosen et al. |
| 5,382,400 A | 1/1995 | Pike et al. |
| 5,393,599 A | 2/1995 | Quantrille et al. |
| 5,418,045 A | 5/1995 | Pike et al. |
| 5,431,991 A | 7/1995 | Quantrille et al. |
| 5,436,066 A | 7/1995 | Chen |
| 5,466,409 A | 11/1995 | Partridge et al. |
| 5,466,410 A | 11/1995 | Hills |
| 5,486,166 A | 1/1996 | Bishop et al. |
| 5,489,469 A | 2/1996 | Kobayashi et al. |
| 5,490,846 A | 2/1996 | Ellis et al. |
| 5,492,754 A | 2/1996 | Chen |
| 5,496,298 A | 3/1996 | Kuepper et al. |
| 5,509,915 A | 4/1996 | Hanson et al. |
| 5,516,585 A | 5/1996 | Young, Sr. et al. |
| 5,527,171 A | 6/1996 | Soerensen |
| 5,536,921 A | 7/1996 | Hedrick et al. |
| 5,540,796 A | 7/1996 | Fries |
| 5,540,992 A | 7/1996 | Marcher et al. |
| 5,562,646 A | 10/1996 | Goldman et al. |
| 5,567,744 A | 10/1996 | Nagata et al. |
| 5,585,170 A | 12/1996 | Morris et al. |
| 5,595,618 A | 1/1997 | Fries et al. |
| 5,599,763 A | 2/1997 | Harada et al. |
| 5,601,542 A | 2/1997 | Melius et al. |
| 5,601,544 A | 2/1997 | Glaug et al. |
| 5,672,419 A | 9/1997 | Mukaida et al. |
| 5,674,339 A | 10/1997 | Groeger et al. |
| 5,722,967 A | 3/1998 | Coles |
| 5,786,785 A | 7/1998 | Gindrup et al. |
| 5,800,418 A | 9/1998 | Ahr |
| 5,858,515 A | 1/1999 | Stokes et al. |
| 5,858,535 A | 1/1999 | Wang et al. |
| 5,885,516 A | 3/1999 | Christensen |
| 5,916,203 A | 6/1999 | Brandon et al. |
| 5,916,506 A | 6/1999 | Breznak et al. |
| 5,962,108 A | 10/1999 | Nestegard et al. |
| 5,972,808 A | 10/1999 | Groeger et al. |
| 5,981,410 A | 11/1999 | Hansen et al. |
| 5,993,433 A | 11/1999 | St. Louis et al. |
| 5,994,615 A | 11/1999 | Dodge, II et al. |
| 6,004,422 A | 12/1999 | Janovec et al. |
| 6,024,813 A | 2/2000 | Groeger et al. |
| 6,024,822 A | 2/2000 | Alper et al. |
| 6,078,035 A | 6/2000 | Chittipeddi et al. |
| 6,140,550 A | 10/2000 | Beihoffer et al. |
| H1909 H | 11/2000 | Ahr |
| 6,160,197 A | 12/2000 | Lassen et al. |
| 6,214,274 B1 | 4/2001 | Melius et al. |
| 6,239,230 B1 | 5/2001 | Eckert et al. |
| 6,242,094 B1 | 6/2001 | Breznak et al. |
| 6,248,097 B1 | 6/2001 | Beitz et al. |
| 6,323,388 B1 | 11/2001 | Melius et al. |
| 6,328,779 B1 | 12/2001 | He et al. |
| 6,330,735 B1 | 12/2001 | Hahn et al. |
| 6,376,011 B1 | 4/2002 | Reeves et al. |
| 6,413,634 B1 | 7/2002 | Tanaka et al. |
| 6,419,798 B1 | 7/2002 | Topolkaraev et al. |
| 6,495,656 B1 | 12/2002 | Haile et al. |
| 6,533,987 B2 | 3/2003 | Topolkaraev et al. |
| 6,562,938 B2 | 5/2003 | Haile et al. |
| 6,593,255 B1 | 7/2003 | Lawton et al. |
| 6,617,490 B1 | 9/2003 | Chen et al. |
| 2002/0115977 A1 | 8/2002 | Topolkaraev et al. |
| 2002/0135103 A1 | 9/2002 | Odorzynski et al. |
| 2002/0150761 A1 | 10/2002 | Lange et al. |
| 2003/0116890 A1 | 6/2003 | Chambers Jr. et al. |
| 2003/0118814 A1 | 6/2003 | Workman, Jr. et al. |
| 2003/0118825 A1 | 6/2003 | Melius et al. |
| 2003/0119394 A1 | 6/2003 | Ranganathan et al. |
| 2003/0119400 A1 | 6/2003 | Beitz et al. |
| 2003/0119401 A1 | 6/2003 | Chakravarty et al. |
| 2003/0119402 A1 | 6/2003 | Melius et al. |
| 2003/0119405 A1 | 6/2003 | Abuto et al. |
| 2003/0119406 A1 | 6/2003 | Abuto et al. |
| 2003/0119413 A1 | 6/2003 | Chakravarty et al. |
| 2003/0129392 A1 | 7/2003 | Abuto et al. |

FOREIGN PATENT DOCUMENTS

| | | |
|---|---|---|
| EP | 0 217 032 B1 | 2/1992 |
| EP | 0479442 A1 | 4/1992 |
| EP | 0509708 A1 | 10/1992 |
| EP | 0525778 A2 | 2/1993 |
| EP | 0533982 A1 | 3/1993 |

| | | | |
|---|---|---|---|
| EP | 0625602 A1 | 11/1994 |
| EP | 0627211 A1 | 12/1994 |
| EP | 0 540 041 B1 | 4/1998 |
| EP | 0842650 A1 | 5/1998 |
| EP | 0916328 A1 | 5/1999 |
| EP | 0 665 315 B1 | 2/2000 |
| EP | 0 649 644 B1 | 5/2000 |
| EP | 1029886 A2 | 8/2000 |
| EP | 1 145 724 A1 | 10/2001 |
| EP | 1 160 426 A2 | 12/2001 |
| GB | 1071191 A | 6/1967 |
| GB | 1092373 | 11/1967 |
| GB | 2 196 343 A | 4/1988 |
| GB | 2301350 A | 12/1996 |
| WO | WO 90/11171 A1 | 10/1990 |
| WO | WO 91/18042 A1 | 11/1991 |
| WO | WO 91/19036 A1 | 12/1991 |
| WO | WO 95/31165 A1 | 11/1995 |
| WO | WO 96/14885 A1 | 5/1996 |
| WO | WO 97/27884 A1 | 8/1997 |
| WO | WO 98/48857 A1 | 11/1998 |
| WO | WO 99/16399 A1 | 4/1999 |
| WO | WO 99/22685 A1 | 5/1999 |
| WO | WO 99/63923 A1 | 12/1999 |
| WO | WO 00/29655 A1 | 5/2000 |
| WO | WO 00/29657 A1 | 5/2000 |
| WO | WO 00/31331 A1 | 6/2000 |
| WO | WO 00/37002 A1 | 6/2000 |
| WO | WO 00/59439 A1 | 10/2000 |
| WO | WO 00/62825 A2 | 10/2000 |
| WO | WO 00/62922 A1 | 10/2000 |
| WO | WO 00/69383 A1 | 11/2000 |
| WO | WO 00/71790 A1 | 11/2000 |
| WO | WO 00/78369 A1 | 12/2000 |
| WO | WO 01/05440 A2 | 1/2001 |
| WO | WO 01/26592 A1 | 4/2001 |
| WO | WO 01/26595 A1 | 4/2001 |
| WO | WO 01/35886 A1 | 5/2001 |
| WO | WO 01/48291 A1 | 7/2001 |
| WO | WO 01/85824 A2 | 11/2001 |
| WO | WO 01/95347 A2 | 12/2001 |
| WO | WO 02/076520 A2 | 10/2002 |
| WO | WO 02/077347 A2 | 10/2002 |

OTHER PUBLICATIONS

Derwent World Patent Database abstract of JP 58019360 A: Description of Unitika Ltd., "Electroconducting Polymer Composition Fibre Produce Preparation Add Cuprous Iodide Electroconducting Carbon Black Granule Polymer."

Derwent World Patent Database abstract of JP 61055249 A: Description of Kanebo Gosen KK, "Electroconducting Nonwoven Antistatic Elastic Polyurethane Fabric Manufacture Mix Poly Isocyanate Molten Polyurethane Elastomer Incorporate Electroconducting Fibre Forming Sheet."

Derwent World Patent Database abstract of Korea: Description of KR 8901835 B, Kim et al./Kolon Co.."Conducting Polyester Fibre Produce Spin Mixture Polyethylene Terephthalate Contain Second Polyester Resin Conducting Carbon Black."

Cavlin, Soren and Christer Fellers, "A New Method for Measuring the Edgewise Compression Properties of Paper," *Svensk Papperstidning*, No. 9, 1975, pp. 329–332.

Mark, Richard E. et al., editors, *Handbook of Physical Testing of Paper*, vol. 1, Second Edition, published by Marcel Dekker, Inc., New York, NY, 2002, including "Edgewise Compression Tests," by Curt A. Bronkhorst and Keith A. Bennett, Chapter 7, pp. 345–349; "Aspects of Sheet Characterization," and "Short–Span Specimen Geometry," by Christer Fellers and Benjamin C. Donner, Chapter 9, pp. 499–503.

Patent Abstracts of Japan 06038814 B4: Description of Igaue Takamitsu et al., "Absorbing Body for Absorfable Article and Preparation Thereof."

American Society for Testing Materials (ASTM) Designation: D 1921–89, "Standard Test Methods for Particle Size (Sieve Analysis) of Plastic Materials," pp. 493–496, published Aug. 1989.

TAPPI Official Test Method T494 om–96, "Tensile properties of paper and paperboard", published by the TAPPI Press, Atlanta, Georgia, revised 1996, pp. 1–10.

*Polymer Blends and Composites*, John A. Manson and Leslie H. Sperling, 1976, Plenum Press, New York, pp. 273–277.

Microwave Processing of Materials, Publication NMAB–473, National Academy Press, Washington, D.C., 1994.

"Reversible Microwave Bonding", Oak Ridge National Laboratory, Mar. 24, 2000, www.ornl.gov/orccmt/pages/projects.html.

"Radio–Frequency Sealing for Disposable Medical Products", Medical Devicelink.com, Mar. 24, 2000, www.devicelink.com/mddi/archive/99/12/003.html.

*Industrial Microwave Heating*, A. C. Metaxas & R. J. Meredith, Peter Peregrinus Ltd., London, England, 1983, p. 152.

METHOD AND APPARATUS FOR MAKING ON-LINE STABILIZED ABSORBENT MATERIALS

FIELD OF THE INVENTION

This invention generally relates to apparatus and method for forming an airformed, stabilized fibrous material. The fibrous material can be a fibrous web which can be employed to produce an absorbent pad for applications such as disposable diapers, child's training pants, feminine care articles, incontinence articles, and the like.

BACKGROUND OF THE INVENTION

In the general practice of forming fibrous web materials, such as airformed webs of absorbent material, it has been common to utilize a fibrous sheet of cellulosic or other suitable absorbent material which has been fiberized in a conventional fiberizer, or other shredding or comminuting device, to form discrete fibers. In addition, particles of superabsorbent material have been mixed with the fibers. The fibers and superabsorbent particles have then been entrained in an air stream and directed to a porous, foraminous forming surface upon which the fibers and superabsorbent particles have been deposited to form an absorbent fibrous web.

The forming surfaces utilized in such systems have been constructed with a wire screen or fluted grid, and a pneumatic flow mechanism, such as provided by a vacuum suction system, has been employed to define a differential pressure zone on the forming surface and impose a pressure differential thereon. The pressure difference has typically provided an airflow through the openings or perforations in the screen or grid of the forming surface. The use of vacuum suction to draw the air-entrained fiber stream onto the forming surface, and pass the airflow through the forming surface has been employed in high-speed commercial operations.

The prior practice of forming airformed fibrous webs has also employed various mechanisms to produce gradations in basis weight along the fibrous webs. For example, the mechanisms have been employed to produce gradations of basis weight along a longitudinal direction of the formed web, i.e., in the direction of movement of the fibrous web through the forming process. Conventional mechanisms have also been employed for providing basis weight variations along a transverse, cross-direction of the formed web.

To form an airlaid, stabilized web, binder materials have been added to the web structure. Such binder materials have included adhesives, powders, netting, and binder fibers. The binder fibers have included one or more of the following types of fibers: homofilaments, heat-fusible fibers, bicomponent fibers, meltblown polyethylene fibers, meltblown polypropylene fibers, and the like.

Conventional systems for producing airlaid, stabilized fibrous webs have mixed the binder fibers with absorbent fibers, and then deposited the mixed fibers onto a porous forming surface by using a vacuum system to draw the fibers onto the forming surface. Such conventional systems, however, have been limited with regard to the lengths of the binder fibers that can be efficiently employed. In the operation of the conventional systems, the lengths of the binder fibers have typically been 6 mm or less. Attempts to use longer binder fibers have caused plugging of distribution screens, non-uniform distribution of fibers, fiber clumping, and other basis weight uniformity problems.

Conventional systems for producing stabilized airlaid webs have required the use of excessive amounts of energy. Where the binder fibers are heat-activated to provide the stabilized web structure, it has been necessary to subject the fibrous web to an excessively long heating time to adequately heat the binder fibers. For instance, typical heating times with through-air bonding systems are in the range of 7–8 seconds. Additionally, it has been necessary to subject the fibrous web to an excessively long cooling time, such as during roll storage in warehouses, to establish and preserve the desired stabilized structure prior to further processing operations. As a result, such conventional systems have been inadequate for manufacturing stabilized airlaid webs directly in-line on consumer product converting machines at high-speeds. A previously used approach has been to manufacture wide, multi-lane base webs off-line. The wide webs have been slit and subsequently converted into desired products on separate manufacturing machines.

Conventional systems for producing off-line stabilized airlaid webs have been configured to make fibrous webs that have straight side edges and substantially uniform basis weights. The stabilized airlaid webs have been cut after the stabilization operation to provide segments of web material having shaped side edges suitable for use in typical consumer products such as feminine care products, diapers, children's training pants, adult incontinent products, and the like. As a result, such conventional systems have been inadequate for making fibrous structures having varied, contoured shapes and contoured basis weights. Additionally, the cutting and shaping of the selected segments of the stabilized web material has wasted excessive amounts of the stabilized material, and has excessively complicated the manufacturing operations. In addition, conventional systems have resulted in excessive costs associated with the shipping, storage, and roll handling of the relatively low density materials.

BRIEF DESCRIPTION OF THE INVENTION

The present invention can provide a method and apparatus for forming a distinctively stabilized, airlaid fibrous layer. The technique of the invention can include: an airforming of a fibrous layer; and an exposing of the fibrous layer to high-frequency electromagnetic energy during a distinctively short activation period to activate the binder-fibers to provide the stabilized, airlaid layer. Additionally, the fibrous layer can be substantially unbonded. In a particular aspect, the activation period can be not more than a maximum of about 3 sec. In another aspect, the fibrous layer can be substantially free of activate, inter-fiber bonds. In a further aspect, the fibrous layer can include substantially unbonded absorbent fibers and substantially unbonded binder-fibers which are substantially unbonded to one another.

In its various aspects and features, the present invention can more effectively and more efficiently make webs of airlaid, stabilized material. For example, the method and apparatus of the invention can more efficiently handle binder-fibers having relatively long lengths. The activation of the binder-fibers to form the desired stabilized structures can be performed at higher speed, and can be conducted with shorter heating times and shorter cooling times. As a result, the binder-fibers can be more efficiently activated with lower amounts of expended energy. Additionally, the method and apparatus can be more efficiently configured to occupy a smaller amount of space. Further, the method and apparatus of this invention can be readily started and stopped without experiencing the detrimental effects produced by commercially available heating and cooling chambers. When a manufacturing line is stopped, the residence of the stopped web within conventional heating and cooling systems can produce non-standard or defective product.

BRIEF DESCRIPTION OF THE DRAWINGS

The invention will be more fully understood and further advantages will become apparent when reference is made to the following detailed description of the invention and to the drawings in which.

DETAILED DESCRIPTION OF THE INVENTION

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

Figure 1:
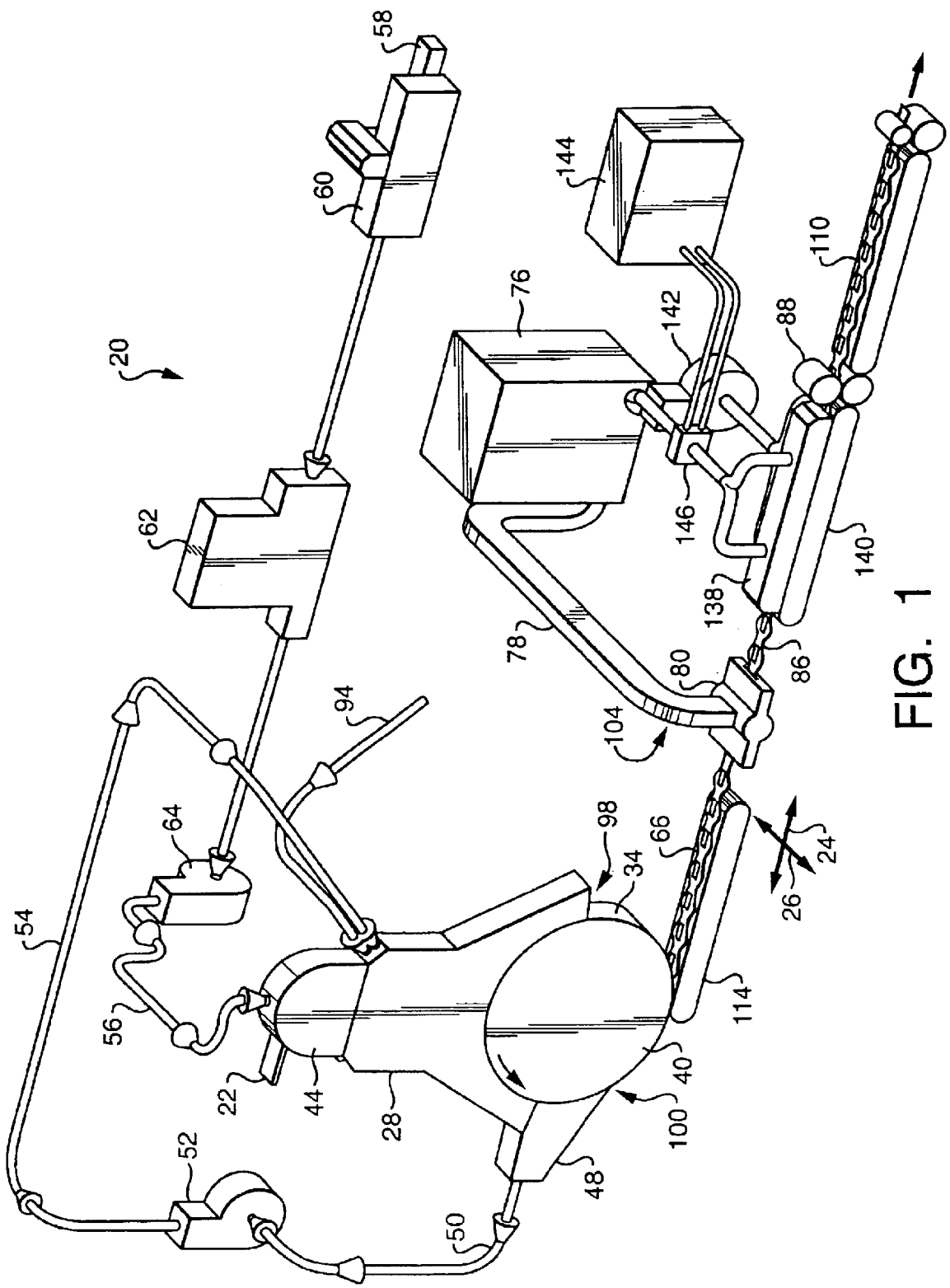
FIG. 1 shows a schematic, perspective view of a representative method and apparatus that can incorporate the present invention to provide an airlaid, stabilized fibrous layer.
Figure 3:
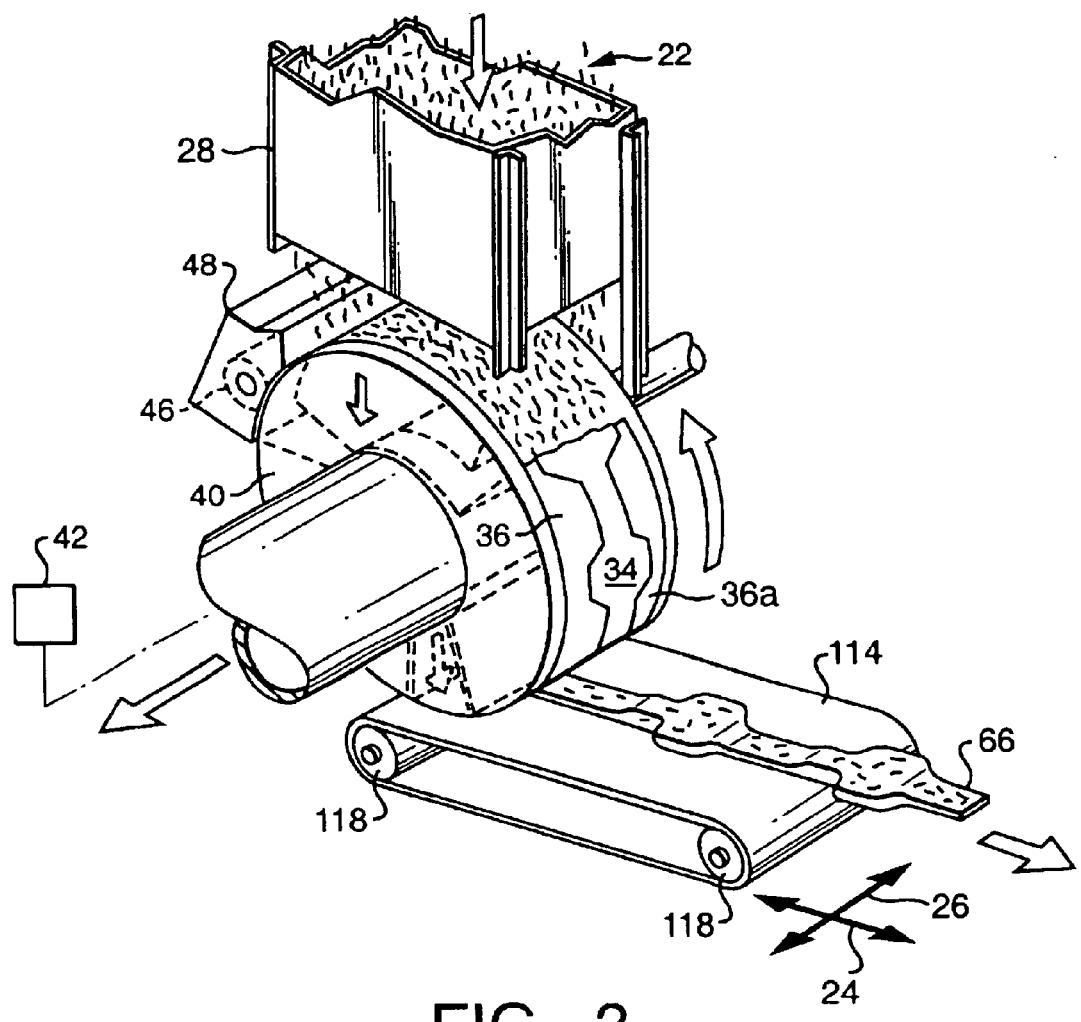
FIG. 3 shows a schematic, partially cut-away, perspective view of a representative airforming system that can be employed with the present invention.
Figure 5:
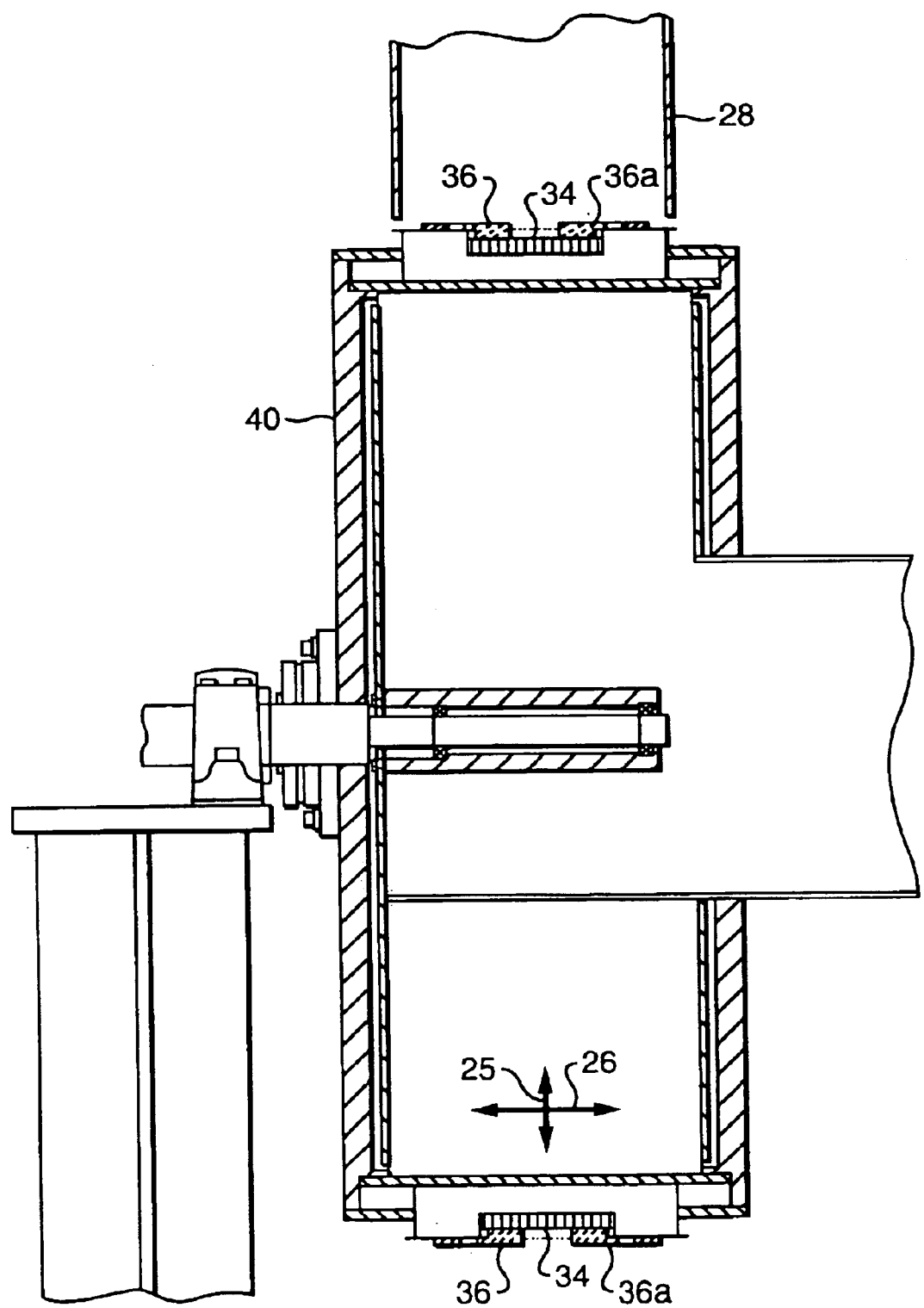
FIG. 5 shows an end view of a representative airforming system that can be employed with the present invention.

With reference to FIGS. 1, 3 and 5, the process and apparatus of the invention can have a lengthwise, machine-direction 24 which extends longitudinally, a lateral cross-direction 26 which extends transversely, and an appointed z-direction 25. For the purposes of the present disclosure, the machine-direction 24 is the direction along which a particular component or material is transported length-wise along and through a particular, local position of the apparatus and method. The cross-direction 26 lies generally within the plane of the material being transported through the process, and is aligned perpendicular to the local machine-direction 24. The z-direction 25 is aligned substantially perpendicular to both the machine-direction 24 and the cross-direction 26, and extends generally along a depth-wise, thickness dimension.

As illustrated, the present invention can provide a distinctive method and apparatus for forming a stabilized, airlaid fibrous web layer 86. The technique of the invention can include an airforming of a fibrous layer 66, and an exposing of the fibrous layer 66 to high-frequency electromagnetic energy during a distinctively short activation period to activate the binder-fibers to provide the stabilized, airlaid web layer 86. Additionally, the fibrous layer can be substantially unbonded. In a particular aspect, the activation period can be not more than a maximum of about 3 sec. In another aspect, the fibrous layer 66 can be substantially free of active or activated, inter-fiber bonds. In a further aspect, the fibrous layer 66 can include substantially unbonded absorbent fibers and substantially unbonded binder-fibers. Additionally, the absorbent fibers and binder-fibers can be substantially unbonded to one another.

It should be appreciated that the fibrous layer 66 may be a part of a composite. In such composite, the fibrous layer 66 can be a web or layer portion which has been or is being airformed by the technique of the invention. The airformed fibrous web layer 66 can be the portion of the composite that is essentially free of a substantially continuously extending, reinforcing or strengthening component, where such strengthening component has been independently formed and arrayed in an operation that is separate from the air-forming operation. Such strengthening component may, for example, be provided by a scrim material, an array of continuous filament fibers, an array of yarns, an array of elastic filaments, a tissue, a woven fabric, a nonwoven fabric, an elastic film, a polymer film, a strengthening substrate, or the like, as well as combinations thereof.

In its various aspects and features, the present invention can more effectively and more efficiently make webs of airlaid, stabilized material. For example, the method and apparatus of the invention can more efficiently employ binder-fibers having relatively longer lengths. The activation of the binder-fibers and/or other web materials to form the desired stabilized structures can be performed at higher speed, and can be conducted with shorter activation times. For example, the activation can be conducted with shorter heating times and shorter cooling times. Additionally, the activation operation can be quickly turned on and off, as desired to accommodate any stops and starts of the method and apparatus. As a result, the activation operation can be conducted along an distinctively short length of processing space. This can allow a more compact arrangement which can be more readily incorporated into an online manufacturing process. In particular configurations, the method and apparatus can produce an airlaid, stabilized fibrous layer that has a selectively contoured basis weight and/or a selectively contoured shape. Additionally, the process and apparatus can more efficiently provide a stabilized web which has a selectively contoured density. The process and apparatus can also more efficiently provide a stabilized layer which has a contoured cross-directional width, wherein the width of the stabilized layer can vary between relatively wide and relatively narrow, as one moves along a longitudinal length of the layer.

Figure 14:
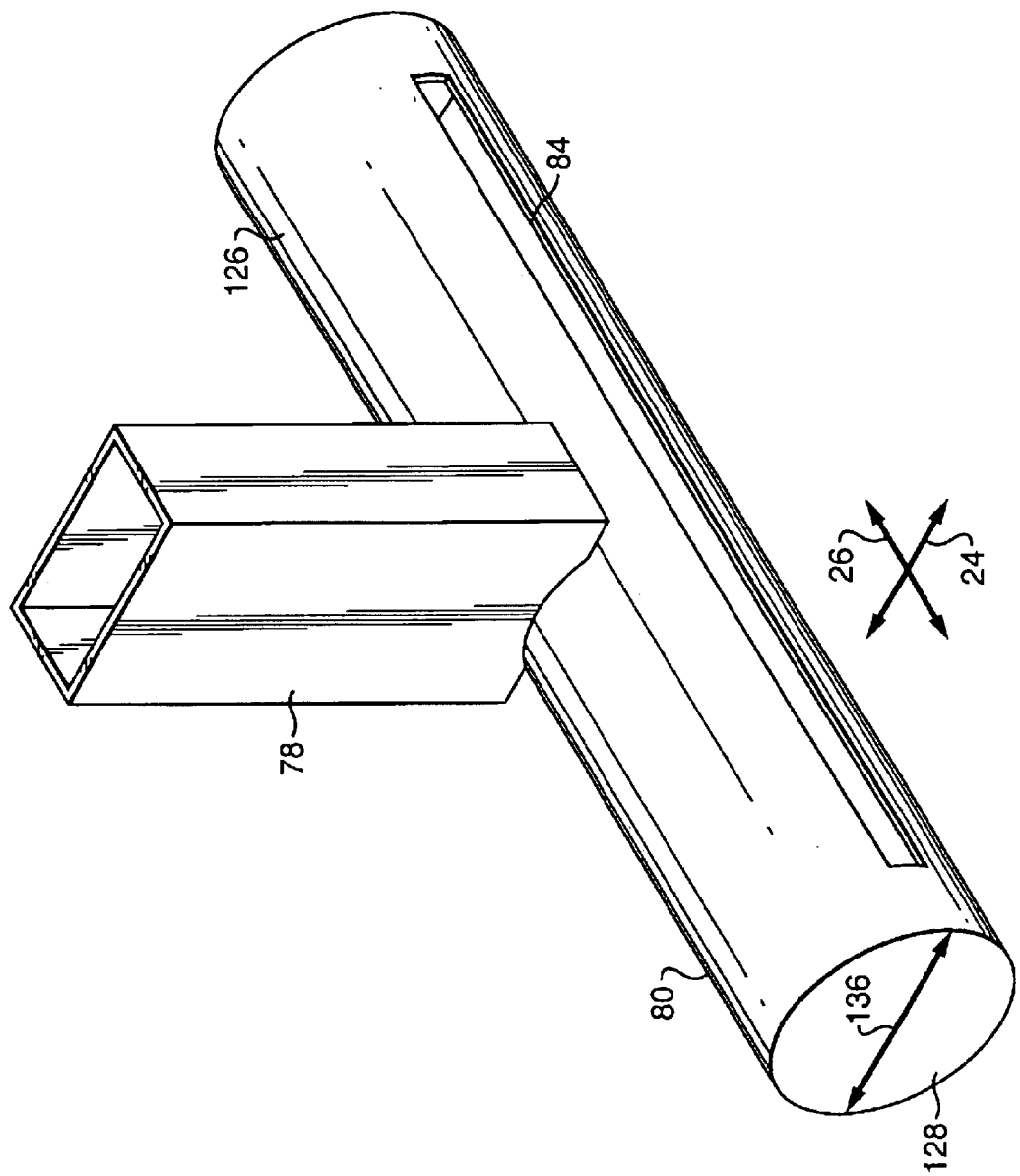
FIG. 14 representatively shows a schematic, perspective view of an activation chamber that can be employed with the present invention.
Figure 18:
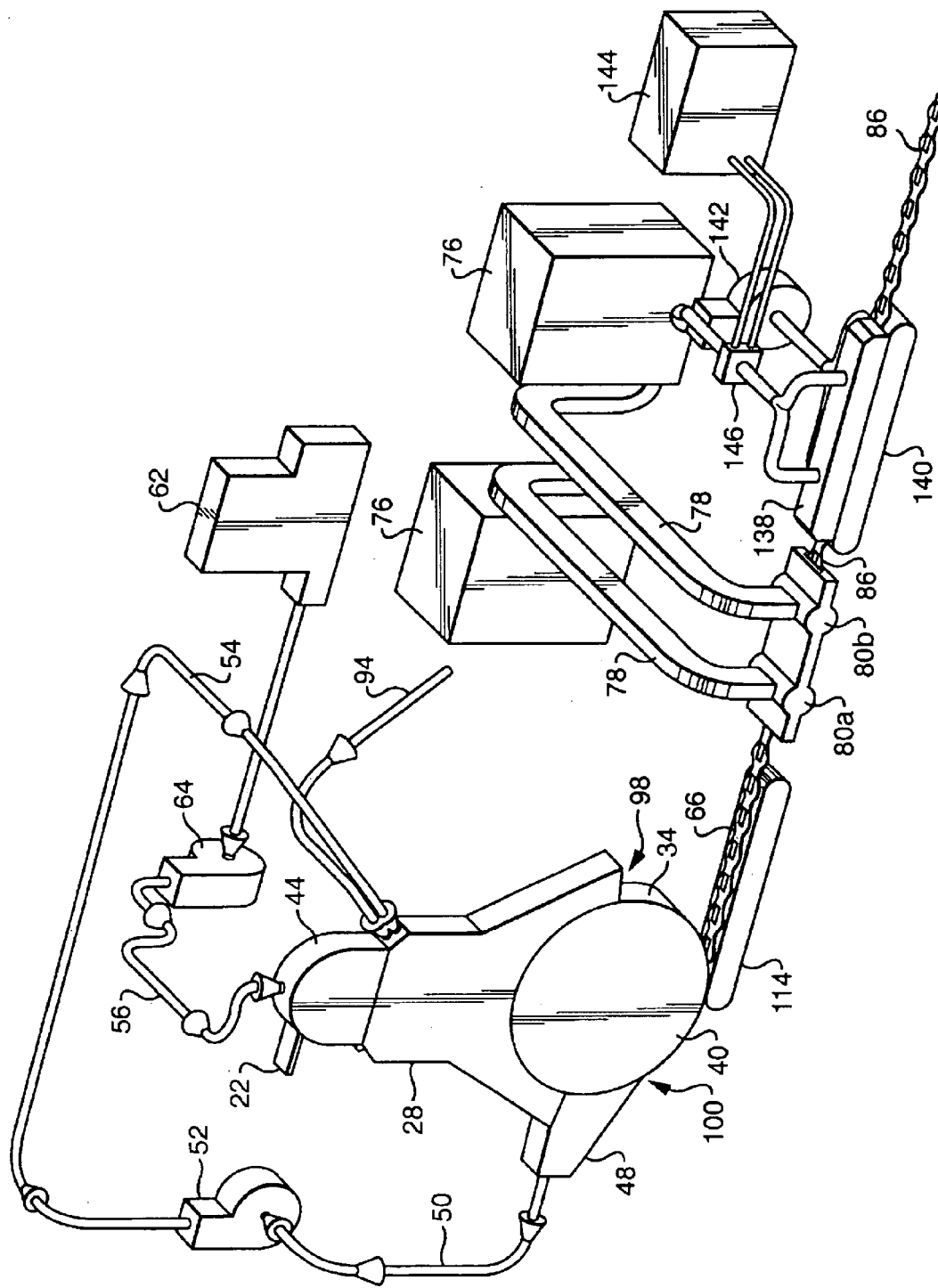
FIG. 18 representatively shows a schematic side view of a configuration that includes a multiplicity of activation chambers.
Figure 18A:
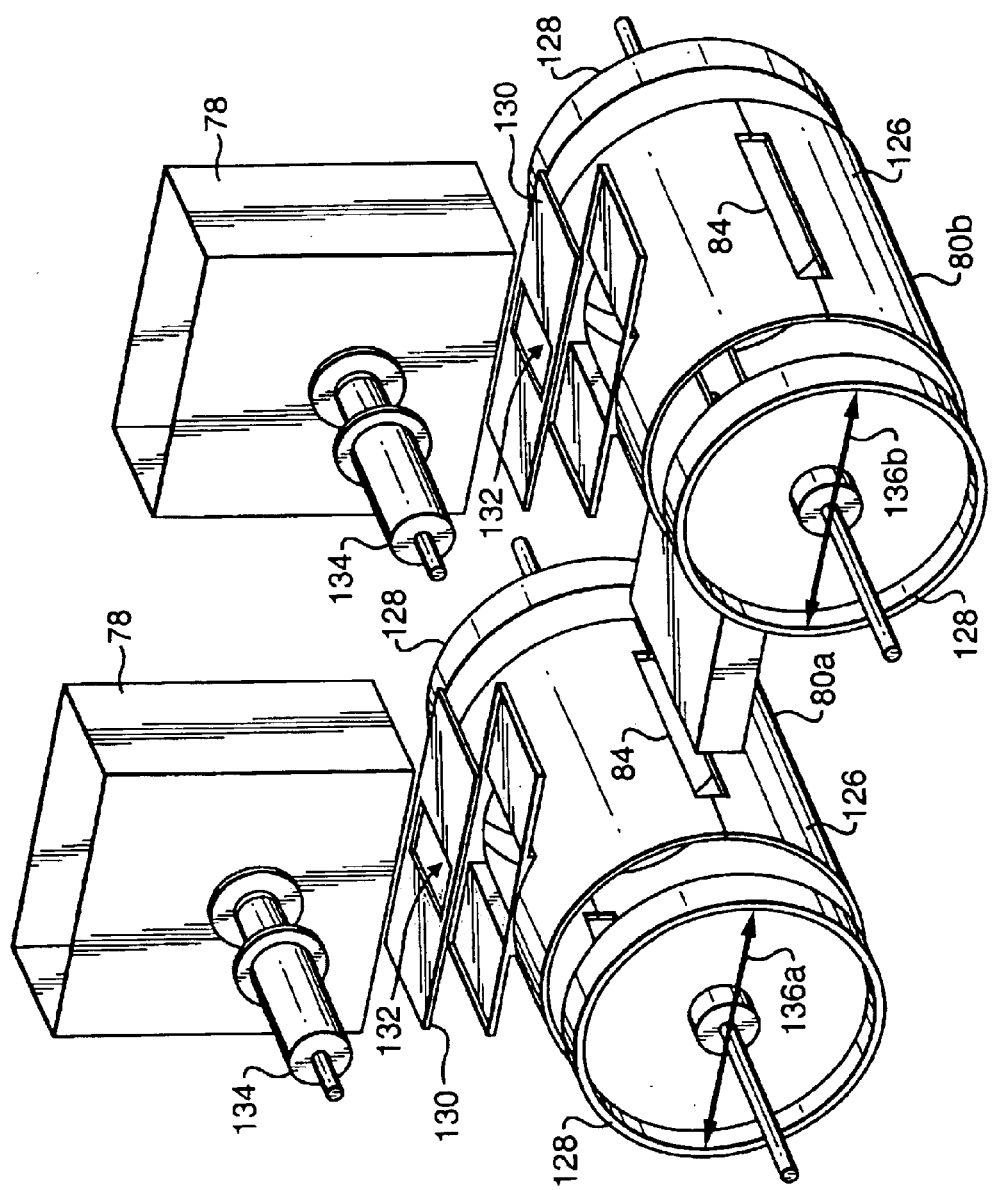
FIG. 18A representatively shows a perspective, exploded view of a plurality of activation chamber that can be selectively tuned.

With reference to FIGS. 1, 14 and 18, a method and apparatus 20 includes a forming chamber 28, a rotatable forming drum 40 and a fiberizer 44. The fiberizer operatively delivers absorbent fibers into the forming chamber. Additionally, a selected amount of binder-fiber can be delivered from a binder-fiber feeder 62, and operatively directed into the forming chamber 28. A fibrous web or layer 66 is airlaid on the forming drum 40, and the fibrous layer may have a longitudinal length which is discontinuous or substantially continuous along the machine-direction of the fibrous layer. The fibrous layer 66 can be directed to an activation system 104, such as a system which includes an activation chamber 80. Within the activation system, the fibrous layer materials can be activated or otherwise processed to provide a stabilized fibrous web or layer 86. A debulking device, such as provided by a counter-rotating pair of compression nip rollers 88, can debulk the stabilized layer 86 to a desired thickness. Additionally, the stabilized layer 86 can be directed for further processing operations, as desired.

A particular feature of the method and apparatus can be configured to deliver a previously shaped and/or contoured fibrous layer or web 66 into a selected activation system 104. In particular, the method and apparatus can be configured to introduce a previously shaped and/or contoured fibrous layer 66 into the activation chamber 80. The fibrous layer can have contoured depth dimensions, contoured side-edge portions, contoured end-edge portions or any desired combinations thereof.

An absorbent fiber material 22 is delivered from a suitable supply source, such as provided by a supply roll or any other operative supply source. The absorbent fiber material is directed into the fiberizer 44, such as provided by a conventional, rotary hammer mill or any other operative fiberizing device. The fiberizer 44 separates the absorbent fiber material 22 into a plurality of substantially individualized, loose absorbent fibers, and the absorbent fibers are directed from the fiberizer into the forming chamber 28. The absorbent fibers move through the forming chamber 28 and deposit onto a foraminous forming surface 34 which is disposed along an outer circumferential surface of the forming drum 40.

Figure 2:
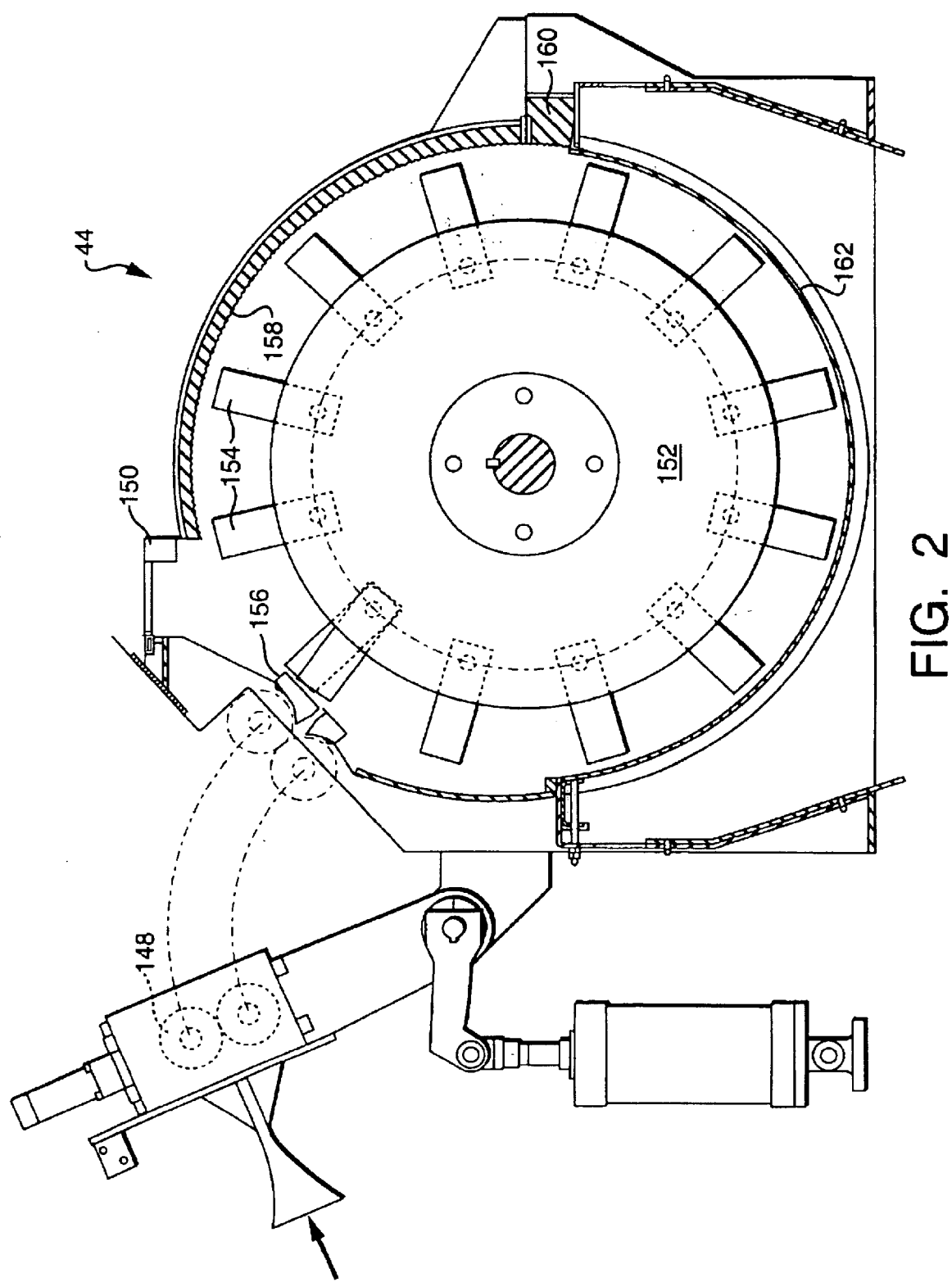
FIG. 2 representatively shows a partly cross-sectioned, side view of a rotary fiberizer that can be employed with the present invention.

With reference to FIG. 2, the fiberizer 44 may be provided by a hammermill. A supply web of absorbent fiber material 22 can be into an entrance of the fiberizer 44 by employing a suitable transport mechanism, such as provided by the representatively shown system of rollers 148. The hammermill includes an outer housing 150, and an operatively driven rotor disk 152 is rotatably disposed in the housing. A plurality of hammer elements 154 are distributed and arrayed along an outer peripheral surface of the rotor disk, and an anvil 156 is located operatively adjacent the entrance of the hammermill. Additionally, grinder plates 158 are distributed along an inner surface of the housing, and a breaker bar 160 can be positioned adjacent an exit region of the fiberizer. A fiberizer screen 162 may optionally be located between the rotor disk 150 (with its hammer elements 154), and the entrance to the forming chamber. Accordingly, the separated absorbent fibers can be directed out of the hammermill through the fiberizer screen and into the forming chamber 28. In a desired, configuration, the fiberizer screen 162 can be removed to provide an improved operation that is less susceptible to undesired, excessive clogging.

The absorbent fibers may be provided by various types of wettable, hydrophilic fibrous material. Examples of suitable fibers can include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber. For the present invention, it is contemplated that selected blends of the various types of fibers mentioned above may also be employed. Useful sources of fibers may include cellulosic fibers including: wood fibers, such as bleached kraft softwood or hardwood, high-yield wood fibers, and ChemiThermoMechanical Pulp fibers; bagasse fibers; milkweed fluff fibers; wheat straw; kenaf; hemp; pineapple leaf fibers; or peat moss. High-yield fibers, such as BCTMP (Bleached ChemiThermal Mechanical Pulp) fibers, can be flash-dried and compressed into densified pads. The high-yield fiber can expand to a higher loft when wetted, and can be used for the absorbent fiber material. Other absorbent fibers, such as regenerated cellulose and curled chemically stiffened cellulose fibers may also be densified to form pads that can expand to a higher loft when wetted. The fibers in the absorbent material may optionally be crosslinked, such as by chemical cross-linking. In a desired arrangement, the absorbent fibers may be suitably derived from a batt of cellulosic fibers (e.g., wood pulp fibers) or other source of natural or synthetic fibers, which has been subjected to an operative fiberization treatment, in a manner well known in the art.

Additionally, a selected quantity of superabsorbent material can be directed into the forming chamber 28 through a suitable superabsorbent conduit 94. Within the forming chamber 28, a conventional superabsorbent nozzle can be operatively configured and arranged to combine the superabsorbent material with the absorbent fiber material within the forming chamber. Particles or fibers of superabsorbent material may be introduced into the forming chamber 28 by employing conventional mechanisms, such as pipes, channels, spreaders, nozzles and the like, as well as combinations thereof. Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 superabsorbent is available from Dow Chemical Company, a business having offices located in Midland, Mich., U.S.A. The fibers and particles may be entrained in any suitable gaseous medium, and references herein to air as being the entraining medium should be understood to be a general reference which encompasses any other operative entrainment gas.

The absorbent fibers and binder-fibers can be cooperatively combined by employing any operative technique. For example, the binder fibers may have been previously combined with or otherwise incorporated into the source of the absorbent fiber material. For instance, the binder fiber may be blended with the absorbent fiber before the absorbent fiber is formed into a roll. In a desired arrangement, the binder-fiber can be separately provided and combined with the absorbent fibers during an on-line operation of the method and apparatus.

As representatively shown, binder-fiber material can be separately delivered from a suitable binder-fiber supply 58, and the binder-fiber material can be processed into individualized binder-fibers. For example, the binder-fiber material may be supplied in the form of bales, and the bales may be opened by employing known, conventional techniques to provide an operative supply of individualized binder-fibers. The operation of a suitable opening device 60 can, for example, include picking, carding, planing or the like, as well as combinations thereof.

Selected quantities of binder-fiber can be directed to a metering device 62, and the metering device can feed controlled quantities of the binder-fiber into a binder-fiber delivery conduit 56. A blower 64 or other suitable device may be employed to help transport the binder fiber through the delivery conduit. The binder-fiber conduit 56 can operatively direct the binder-fibers into the forming chamber 28. The binder-fiber metering device can be provided by a model number CAM-1X12 system which is available from Fiber Controls, Inc., a business having offices located in Gastonia, N.C., U.S.A.

The binder-fibers may, for example, be provided by staple short cut fibers, bicomponent fibers, homofilament fibers, biconstituent fibers and the like, as well as combinations thereof. Desirably, the binder fibers can bind to themselves and to the absorbent fibers upon exposure to an operative activation energy. In a particular feature, the binder fibers can be easily heated by microwave energy, and/or have relatively low melting temperature below about 200° C. In a further feature, the binder fibers can be easily heated by microwave energy, and/or have relatively low melting temperature below about 150° C.

In a desired aspect, the binder-fibers can have a fiber length which is at least about 0.061 mm. The binder-fiber length can alternatively be at least about 3 mm and can optionally be at least about 6 mm. In a further feature, the binder-fibers can have a length which is up to about 30 mm, or more. The binder-fiber length can alternatively be up to about 25 mm, and can optionally be up to about 19 mm. In a further aspect, the fibrous layer may include binder-fibers having lengths that approximate one of the dimensions of an appointed absorbent web segment 120 intended for a single finished product article.

The relatively long length of the binder-fibers can help the binder fiber have an increased number of contact points with the absorbent fibers to thereby increase the number of bonding points to help generate improved integrity and permeability In a desired feature the binder-fibers are individualized and substantially discontinuous.

In another aspect, the binder-fibers can be configured to provide an enhanced absorption of radio-frequency energy. In particular, the binder-fibers can be configured to provide an enhanced absorption of microwave energy. The enhanced absorption of radio-frequency energy can be provided by employing a binder-fiber material which includes a microwave-sensitized material having a high dielectric loss factor. The binder-fibers can, for example, have a loss factor which is not less than a minimum of about 0.05, as measured at a frequency of 1 GHz. The dielectric loss factor can alternatively be not less than about 0.1, and can optionally be not less than about 0.5 to provide improved performance. In other aspects, the dielectric loss factor can be up to a maximum of about 1000, or more. The dielectric loss factor can alternatively be up to about 500, and can optionally be up to about 250 to provide improved effectiveness.

In a desired feature, the dielectric loss factor of the binder-fibers can be much greater than the dielectric loss factor of the absorbent fibers. For example, absorbent cellulose fibers can have a dielectric loss factor of about 0.05, as measured at 1 GHz. Due to the difference in the dielectric loss factors, the binder-fibers can be heated significantly more than the absorbent fibers when the microwave energy is applied.

The "dielectric loss factor" is a measure of the receptivity of a material to high-frequency energy. The measured value of $\epsilon'$ is most often referred to as the dielectric constant, while the measured value of $\epsilon''$ is denoted as the dielectric loss factor. These values can be measured directly using a Network Analyzer with a low power, external electric field (i.e., 0 dBm to +5 dBm) typically over a frequency range of 300 KHz to 3 GHz, although Network Analyzers to 20 GHz are readily available. For example, a suitable measuring system can include an HP8720D Dielectric Probe, and a model HP8714C Network Analyzer, both available from Agilent Technologies, a business having offices located in Brookfield, Wis., U.S.A. Substantially equivalent devices may also be employed. By definition, $\epsilon''$ is always positive, and a value of less than zero is occasionally observed when $\epsilon''$ is near zero due to the measurement error of the analyzer.

For sensitizing the binder-fibers, exemplary materials can include polyamide or polyvinyl methyl based hotmelt adhesives, and other thermoplastics known in the art. Polyether block amides, polyvinylchloride (PVC), and related compounds also have high loss factors, and may be employed. Additives may be incorporated into the binder fibers to enhance microwave energy coupling with the binder fibers. Examples of additives can include but are not limited to various mixed valent oxides, such as magnetite ($Fe_3O_4$), nickel oxide (NiO) and the like; carbon, carbon black and graphite; sulfide semiconductors, such as $FeS_2$, $CuFeS_2$; silicon carbide; various metal powders such as powders of aluminum, iron and the like; various hydrated salts and other salts, such as calcium chloride dihydrate; diatomaceous earth; aliphatic polyesters (e.g. polybutylene succinate and poly(butylene succinate-co-adipate, polymers and co-polymers of polylactic acid, low melt temperature polymers such as PEO and copolymers of PEO); various hygroscopic or water absorbing materials or more generally polymers or copolymers or non-polymers with many sites of —OH groups; other inorganic microwave absorbers including aluminum hydroxide, zinc oxide, barium titanate and other organic absorbers such as polymers containing ester, aldehyde, ketone, isocyanate, phenol, nitrile, carboxyl, vinylidene chloride, ethylene oxide, methylene oxide, epoxy, amine groups, polypyrroles, polyanilines, polyalkylthiophenes; as well as combinations and mixtures thereof. The selected additive may be ionic or dipolar, such that the applied energy field can activate the molecule.

Suitable binder-fibers and structures which include such binder-fibers are disclosed in U.S. patent application Ser. No. 10/034,079 entitled TARGETED BONDING FIBERS FOR STABILIZED ABSORBENT STRUCTURES by F. Abuto et al., which was filed on Dec. 20, 2001: in U.S. patent application Ser. No. 10/034,021 entitled ABSORBENT STRUCTURES HAVING LOW MELTING FIBERS by J. Workman et al., which was filed on Dec. 20, 2001: and in U.S. patent application Ser. No. 10/033,860 entitled TARGETED ON-LINE STABILIZED ABSORBENT STRUCTURES by F. Abuto et al., which was filed on Dec. 20, 2001: . The entire disclosures of these documents are incorporated herein by reference in a manner that is consistent herewith.

The absorbent fibers, the binder-fibers and the superabsorbent material can be operatively mixed or otherwise combined within the forming chamber 28, and the mixing of the absorbent fiber, binder-fiber, superabsorbent particles and/or other constituent materials can be configured to be non-homogeneous or substantially homogeneous, as desired. The stream of air-entrained fibers and particles can pass through the forming chamber 28 to the forming drum system 40. The forming chamber can serve to direct and concentrate the air-entrained fibers and particles, and to provide a desired velocity profile in the air-entrained stream of fibers and particles. The forming chamber is typically supported by suitable structural members, which together form a support frame for the forming chamber. The frame may be anchored and/or joined to other suitable structural components, as necessary or desirable.

The forming chamber 28 can include an appointed entrance region 98, and an appointed exit region 100. When the binder-fibers are directed into a portion of the forming chamber 28 which is positioned more closely to the entrance region of the forming chamber, the binder-fibers can be more concentrated toward a forming surface side 68 (e.g. FIG. 19A) of the fibrous layer 66 formed on the forming surface 34. When the binder-fibers are directed into a portion of the forming chamber 28 which is relatively closer to the exit region of the forming chamber, the binder-fibers can be more concentrated toward a free-surface side 70 of the fibrous layer 66.

Figure 10:
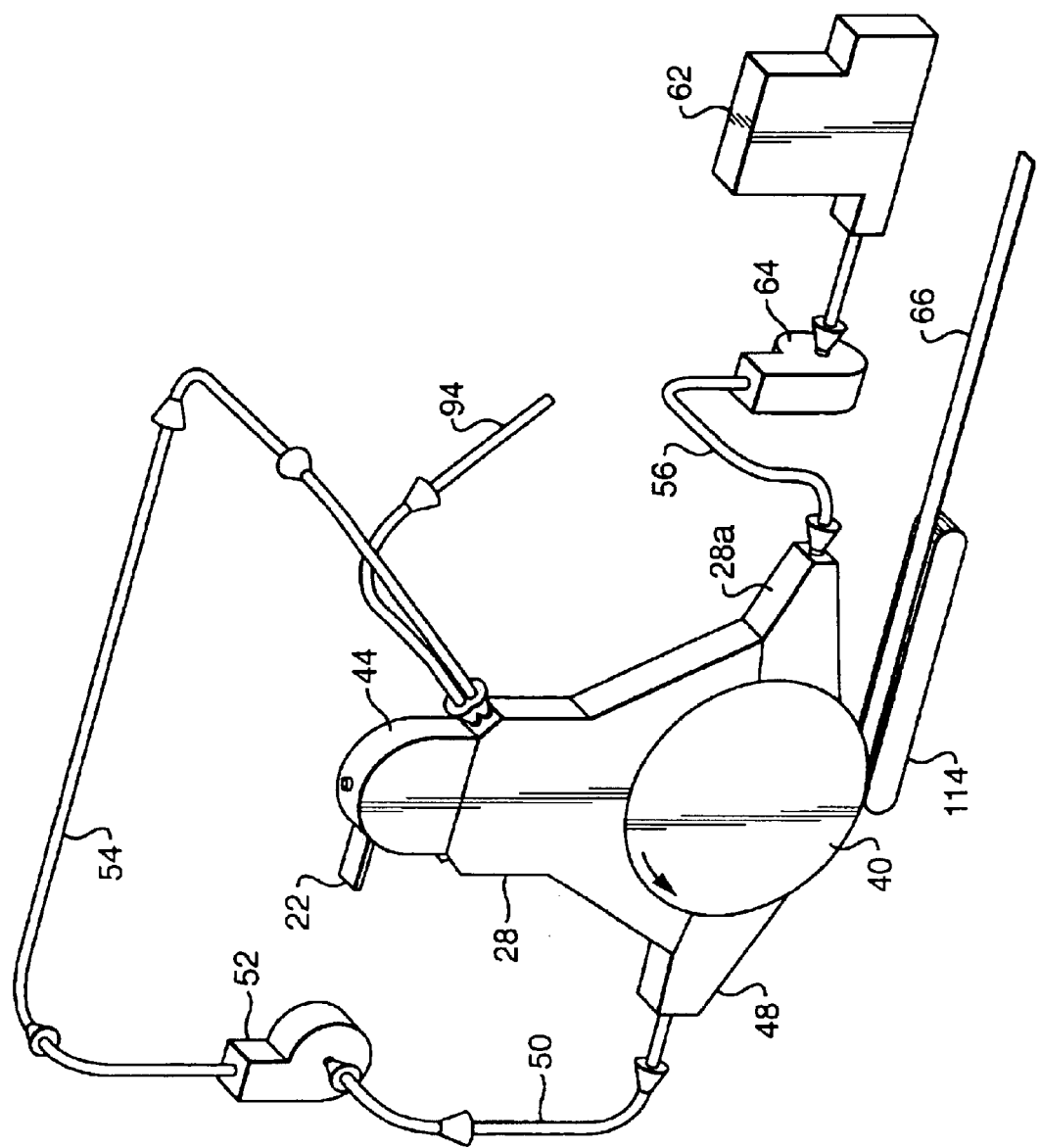
FIG. 10 shows a schematic, perspective view of an alternative forming system which is configured to introduce binder-fiber into a leading forming chamber which is located at an upstream, entrance-end of the forming system.

The binder-fibers may be directed or otherwise introduced into the forming chamber 28 at any desired location. In a particular arrangement, the binder-fibers can be introduced into the forming chamber at an inlet location that is relatively remotely spaced from the location at which the fiberizer 44 directs the absorbent fibers into the forming chamber 28. For example, a forming system can be configured to introduce the binder-fiber into a leading forming chamber 28a which is located at an upstream, entrance-end of the forming system (e.g. FIGS. 10 and 10A). In another configuration, the binder-fibers can be introduced into the forming chamber at an inlet location that is generally adjacent the location at which the fiberizer 44 directs the absorbent fibers into the forming chamber 28. For example, an alternative forming system may be configured to introduce binder-fiber into a relatively upstream portion of the forming chamber that is relatively closer to an entrance region of the forming system. In a particular arrangement, the inlet location can be upstream from and substantially immediately adjacent to the location at which the fiberizer directs the absorbent fibers into the forming chamber 28 (e.g. FIGS. 11 and 11A).

Figure 13:
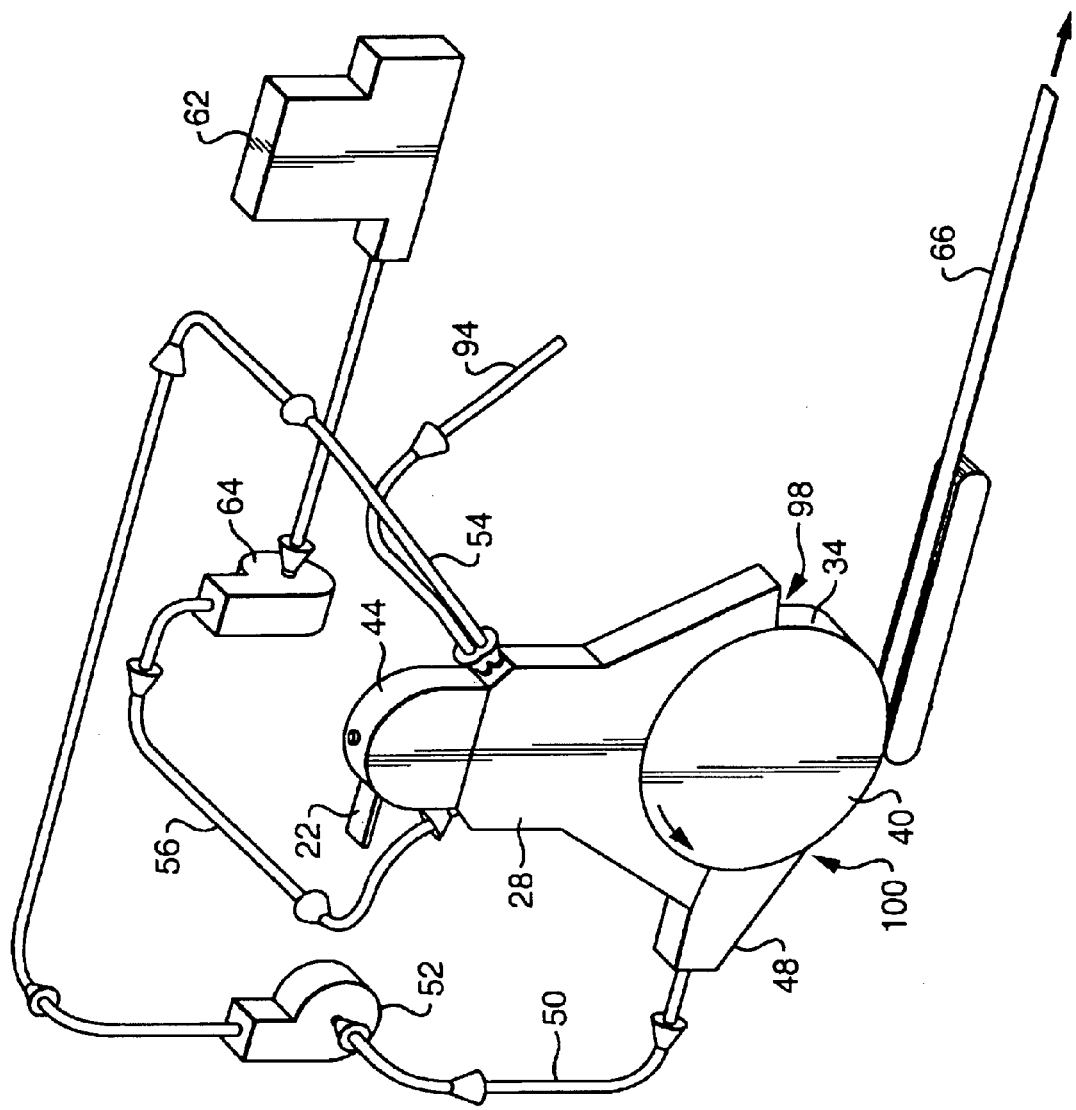
FIG. 13 shows a schematic, perspective view of an alternative forming system which is configured to introduce binder-fiber into a relatively downstream portion of the forming chamber that is relatively closer to an exit region of the forming system.

In another arrangement, the forming system can be configured to introduce the binder-fiber into a relatively downstream portion of the forming chamber that is relatively closer to an exit region of the forming system. For example, the inlet location can be downstream from and substantially immediately adjacent to the location at which the fiberizer directs the absorbent fibers into the forming chamber 28 (e.g. FIG. 13).

Figure 12:
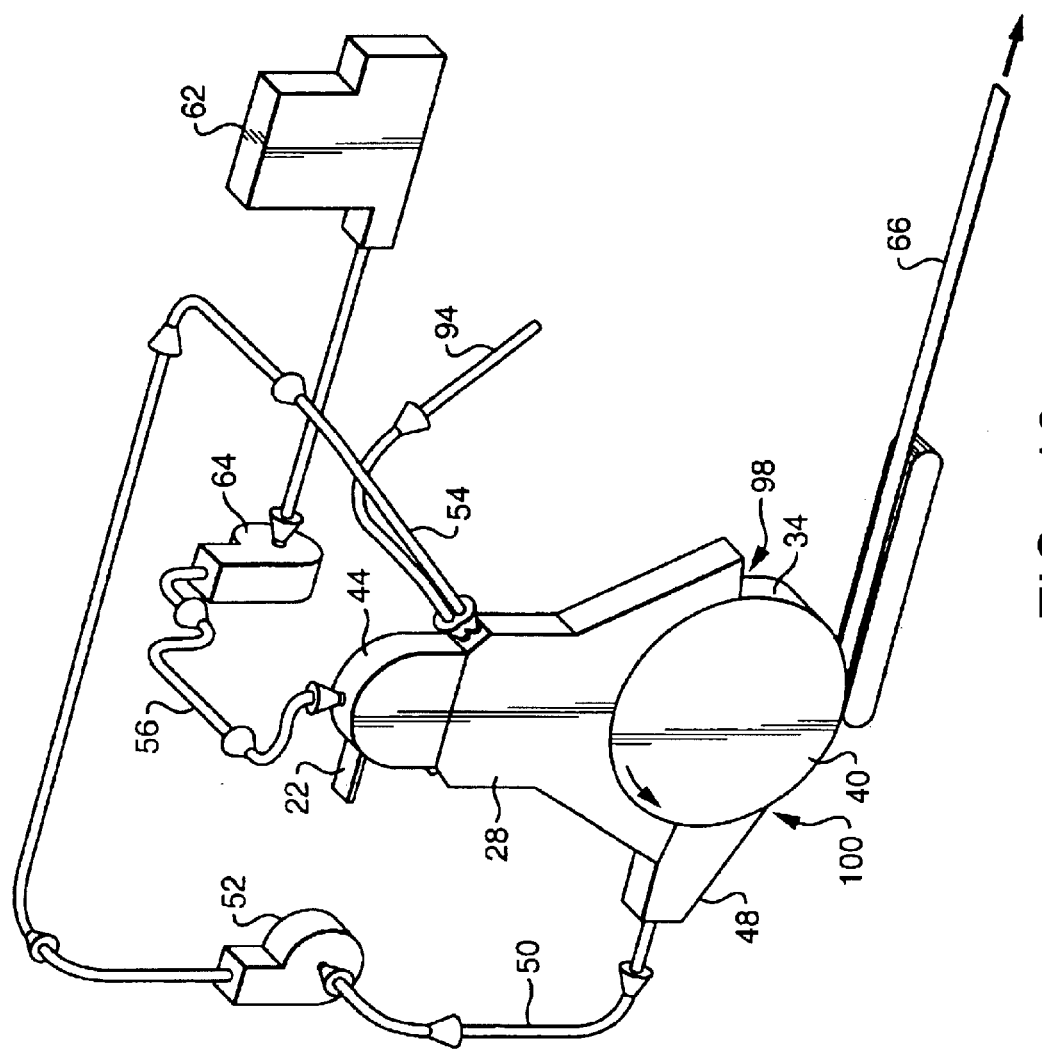
FIG. 12 shows a schematic, perspective view of an alternative forming system which is configured to introduce binder-fiber into the fiberizer employed with the forming system.

In a particular configuration, the closely-adjacent introduction of the binder-fiber into the forming chamber 28 can be accomplished by directing the binder-fiber into and through the fiberizer 44 (e.g. FIG. 12). A rotating motion within the fiberizer can help disperse and mix the binder-fibers with the absorbent fiber material. It has been found that the fiberizer did not excessively damage the binder-fibers. Where the binder-fibers are directed into the fiberizer 44, there can be rotary action that can help provide a substantially homogenous mixture of binder-fibers and absorbent fibers in the forming chamber. Accordingly, a substantially uniform or substantially homogeneous mixture of binder-fibers and absorbent fibers can be produced in the airformed fibrous layer 66. It should be appreciated that the combination of absorbent fibers, binder-fibers and optional superabsorbent particles can be operatively deposited and accumulated onto the forming surface 34 to produce the desired fibrous layer 66.

The binder-fibers may also be directed or otherwise introduced into the forming chamber 28 at one or more of the binder-fiber inlet locations that are disclosed herein. Accordingly, the binder-fibers may be directed or otherwise introduced into the forming chamber 28 at any desired combination of the binder-fiber inlet locations.

The forming drum 40 is rotatable in a selected direction of rotation, and can be rotated by employing a drum drive shaft that is operatively joined to any suitable drive mechanism (not shown). For example, the drive mechanism can include an electric or other motor which is directly or indirectly coupled to the drive shaft. While the shown arrangement provides a forming drum that is arranged to rotate in a counter-clockwise direction, it should be readily apparent that the forming drum may alternatively be arranged to rotate in a clockwise direction.

The forming drum can provide a laydown zone which is positioned within the forming chamber 28 and operatively provides a vacuum laydown zone of the foraminous forming surface 34. This vacuum laydown zone constitutes a circumferential, cylindrical surface portion of the rotatable drum 40. An operative pressure differential is imposed on the surface of the vacuum laydown zone under the action of a conventional vacuum generating mechanism 42, such as provided by a vacuum pump, an exhaust blower, a centrifugal fan or other suitable mechanism which can provide a relatively lower pressure under the forming surface 34. The vacuum mechanism can operatively withdraw air through a conventional air discharge duct from the arcuate segment of the forming drum that is cooperatively associated with the vacuum laydown surface.

In a particular feature, the level or strength of the vacuum suction can be selectively regulated to control the density of the fibrous layer 66 that is being airformed on the forming surface 34. A relatively greater suction strength can be employed to produce a relatively higher density or low porosity, in the airformed web 66, and a relatively lower suction strength can be employed to produce a relatively lower density or high porosity, in the airformed web. The specific level of suction strength will depend upon the specific flow characteristics that are present in the particular airforming system. It is readily apparent that a desired suction strength can be found by employing a short, iterative series of well known, trial steps. The density that is generated in the fibrous layer 66 prior to a subsequent activation operation can be important for controlling the desired functional properties that are provided in the final configuration of the web.

Figure 4:
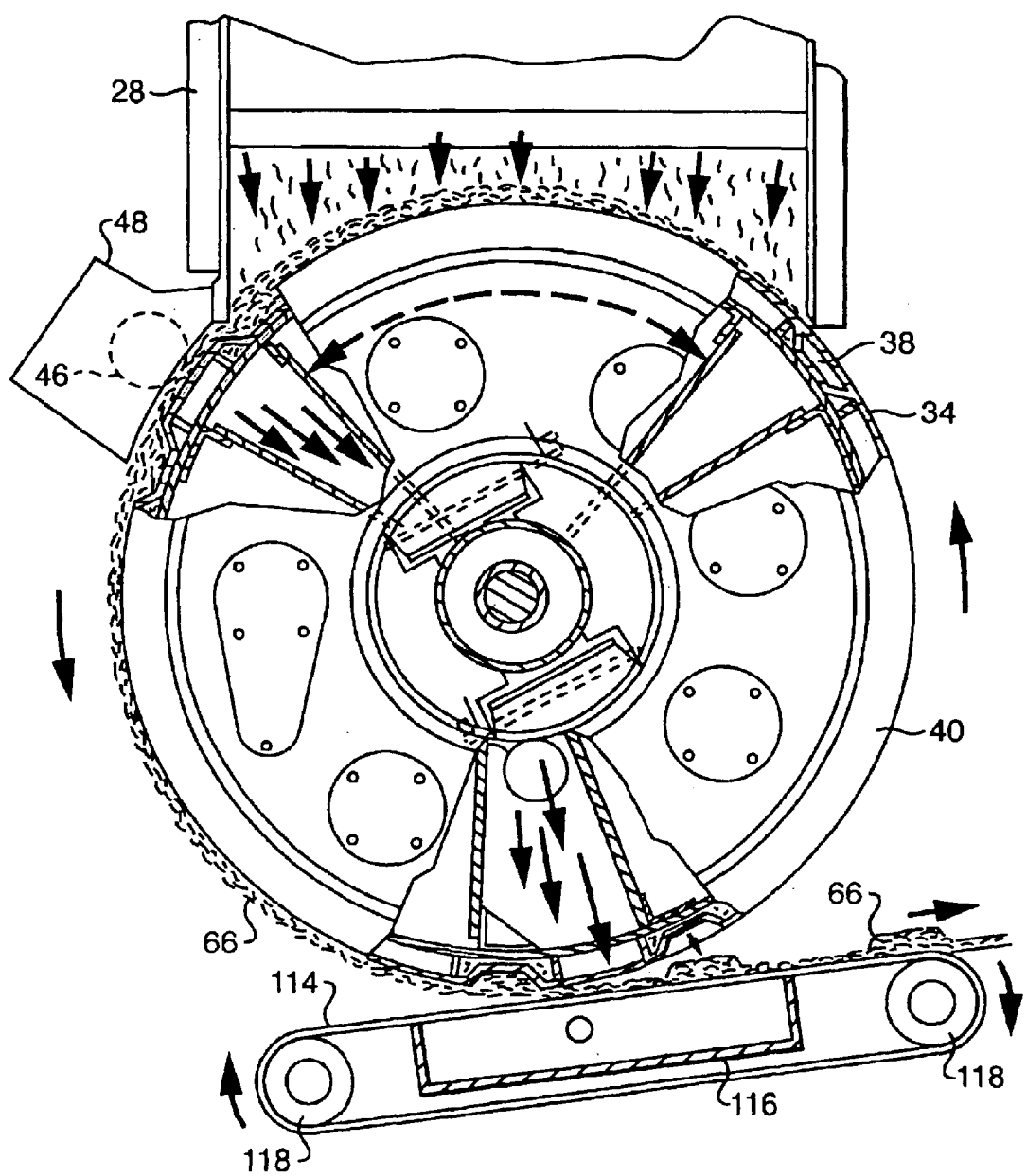
FIG. 4 shows a partially cut-away, side view of a representative airforming system that can be employed with the present invention.

With reference to FIGS. 1, 4 and 5, the forming surface 34 can be provided along the outer, cylindrical surface of the forming drum 40, and forming surface can include a plurality of concavely contoured forming surface portions that are circumferentially spaced apart along the outer surface of the forming drum. The foraminous forming surface 34 can include a series of forming sections which are distributed circumferentially along the periphery of the forming drum 40. In desired arrangements, the forming sections can provide a selected repeat pattern that is formed in the fibrous layer 66. The repeat pattern can correspond to a desired shape of an individual absorbent pad that is intended for assembly or other placement in a desired absorbent article.

Suitable forming drum systems for producing airformed fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are disclosed in U.S. patent application Ser. No. 09/785,959 entitled APPARATUS AND PROCESS FOR FORMING A LAID FIBROUS WEB WITH ENHANCED BASIS WEIGHT CAPABILITY by J. T. Hahn et al., which was filed Feb. 16, 2001: the entire disclosure of which is incorporated herein by reference in a manner that is consistent herewith. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

Thus, under the influence of the vacuum mechanism 42, a conveying air stream is drawn through the foraminous forming surface 34 into the interior of the forming drum, and is subsequently passed out of the drum through the discharge duct. As the air-entrained fibers and particles impinge on the foraminous forming surface 34, the air component thereof is passed through the forming surface and the fibers-particles component is retained on the forming surface to form a nonwoven fibrous layer 66 thereon. Subsequently, with the rotation of the drum, the formed web 66 can be removed from the forming surface by the weight of the fibrous layer 66, by centrifugal force, and by a removal force produced, for example, by a pressurized air flow through a blow-off zone and a transfer-vacuum suction. The pressurized air can exert a force directed outwardly through the forming surface. Additionally, the distinctive configurations of the forming surface and associated components, can produce a fibrous layer 66 which can be more readily removed from the forming drum 40.

The forming drum of the illustrated configuration can be rotatable about a series of stationary baffles which can present to the foraminous forming surface, a plurality of differential pressure zones. The pressure differentials imposed on the foraminous forming surface 34 can be produced by any conventional, vacuum generating mechanism 42, such as an exhaust fan, which is connected to an is air discharge duct and is operatively joined to the forming drum structure by employing a conventional coupling mechanism. The interior space of the forming drum 40 can includes a high vacuum forming zone which is in the general form of an arcuate segment that is operatively located at the portion of the forming surface 34 that is positioned within the forming chamber 28. In the shown configuration, the high vacuum forming zone is located generally subjacent the forming chamber. In operation, the airformed fibrous layer 66 can be produced from the stream of air-entrained fibers (and particles) as the entrainment gas flows the through the openings in the foraminous forming surface 34 and into the interior of the rotating forming drum 40.

After the fibrous web or layer 66 departs the forming chamber 28, the fibrous web or layer can be subjected to a scarfing operation to remove excess material and provide a desired basis weight distribution within the fibrous layer 66. The scarfing system can include a scarfing chamber 48, and a scarfing roll 46 which is operatively positioned within the scarfing chamber. The scarfing systems are conventional and well known in the art, and are readily available from commercial vendors.

The drum rotation can pass the airformed fibrous layer 66 from the vacuum laydown zone within the forming chamber to a scarfing zone within the scarfing chamber where excess thickness of the fibrous layer can be trimmed and removed to a predetermined extent. As representatively shown, the fibrous layer 66 can be operatively processed by the scarfing roll 46, which is disposed on a suitable shaft member and driven by a suitable drive mechanism (not shown) which may be any conventional mechanism. For example, the scarfing roll can be driven by a motor, or by a gear coupling or other transmission mechanism connected to the motor or drive device that is employed to drive the rotatable forming drum 40. The scarfing roll can provide a conventional trimming mechanism for removing any excess, radial thickness of the airformed fibrous layer that has been deposited on the forming surface 34. The scarfing operation can yield a fibrous layer having a selected contour on a major face surface of the fibrous layer that has been contacted by the scarfing roll 46. The surface of the scarfing roll can be adjusted to provide a desired contour along the scarfed surface of the fibrous layer 66. In the representatively shown arrangement, the scarfing roll can, for example, be configured to provide a substantially flat surface along the scarfed surface of the fibrous layer 66. The scarfing roll can optionally be configured to provide a non-flat surface. The scarfing roll 46 is disposed in spaced adjacent relationship to the forming surface, and the forming surface is translated past the scarfing roll. A conventional transporting mechanism, such as a suction fan 52 can draw the removed fibrous material away from the formed fibrous layer and out from the scarfing chamber 48.

In the representatively shown configuration, the scarfing roll 46 rotates in a direction which moves a contacting surface of the scarfing roll in a counter-direction that is opposite the movement direction of the airformed fibrous layer 66. Alternatively, the scarfing roll 46 may be rotated to provide a co-directional movement of the roller surface relative to the surface of the forming drum most proximate thereto. In either situation, the rotational speed of the scarfing roll 46 should be suitably selected to provide an effective scarfing action against the contacted surface of the formed fibrous layer. In like manner, any other suitable trimming mechanism may be employed in place of the scarfing roll assembly to provide a cutting or abrading action to the laid fibrous layer by a relative movement between the fibrous layer 66 and the selected trimming mechanism.

The scarfing roll 46 can operatively remove excess material from the fibrous layer 66. The excess material is directed out of the scarfing chamber 48 through a discharge conduit 50.

As representatively shown, the removed material can be recycled into the forming chamber 28 through a suitable recycle conduit 54. An operative transporting system can be employed to direct and move the recycled material from the scarfing chamber 48 to the forming chamber 28. As representatively shown, a convention blower system 52 can help move the recycled material into the forming chamber.

Figure 10A:
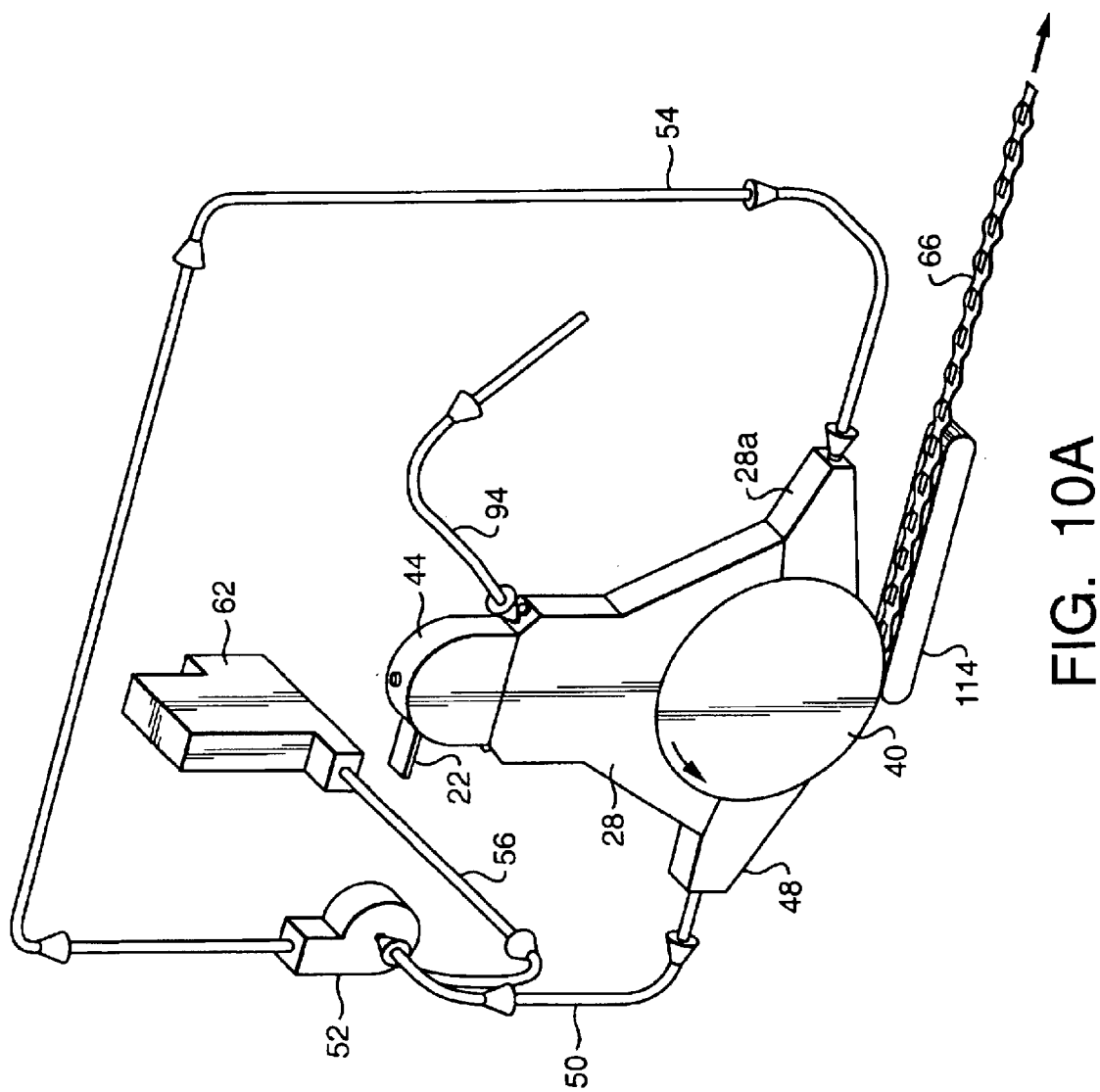
FIG. 10A shows a schematic, perspective view of an alternative forming system which is configured to combine the binder-fiber with scarfed material delivered from a scarfing operation, and introduce the combined binder-fiber and scarfed material into a leading forming chamber which is located at an upstream, entrance-end of the forming system.
Figure 11:
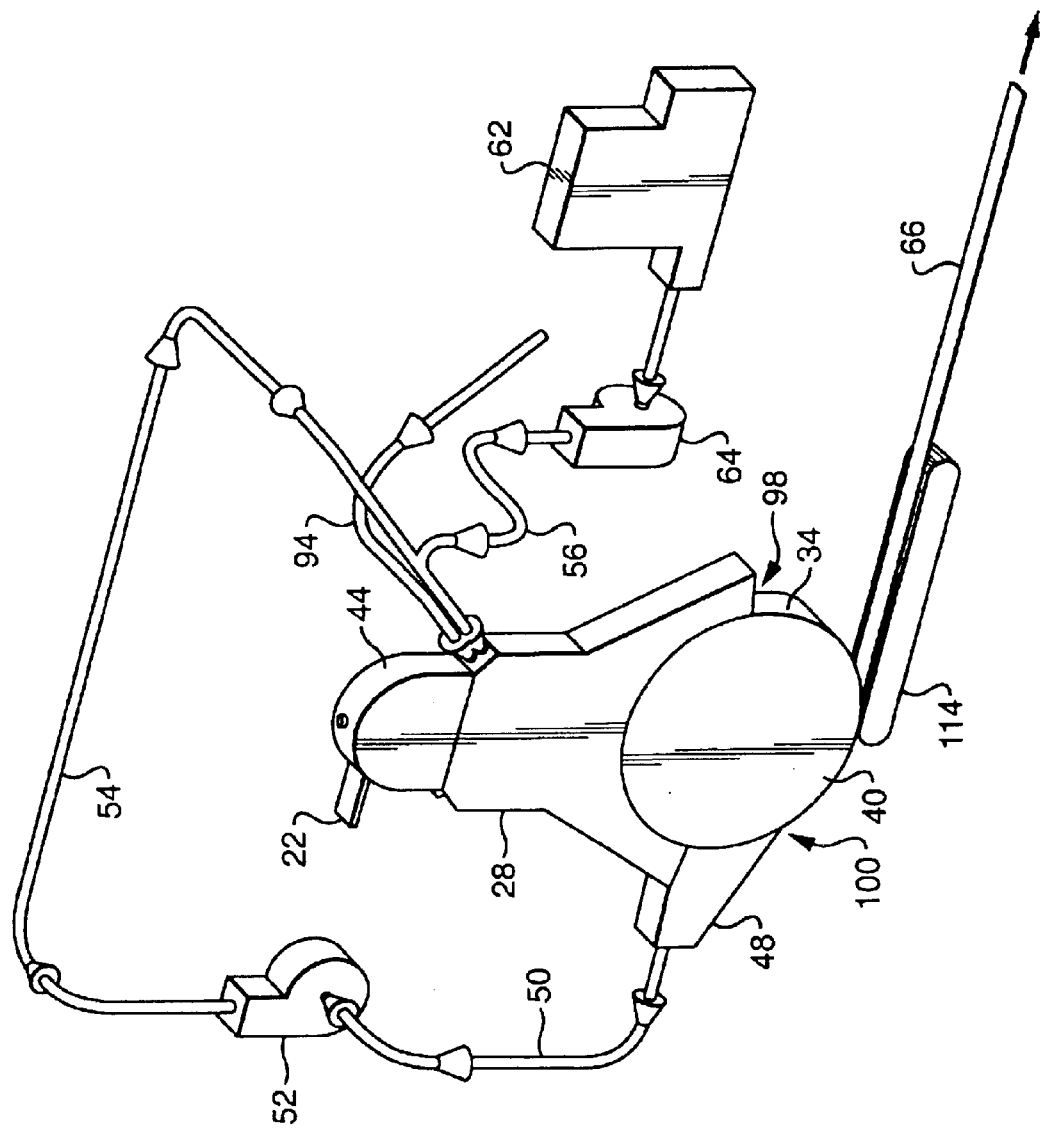
FIG. 11 shows a schematic, perspective view of an alternative forming system which is configured to introduce binder-fiber into a relatively upstream portion of the forming chamber that is relatively closer to an entrance region of the forming system.
Figure 11A:
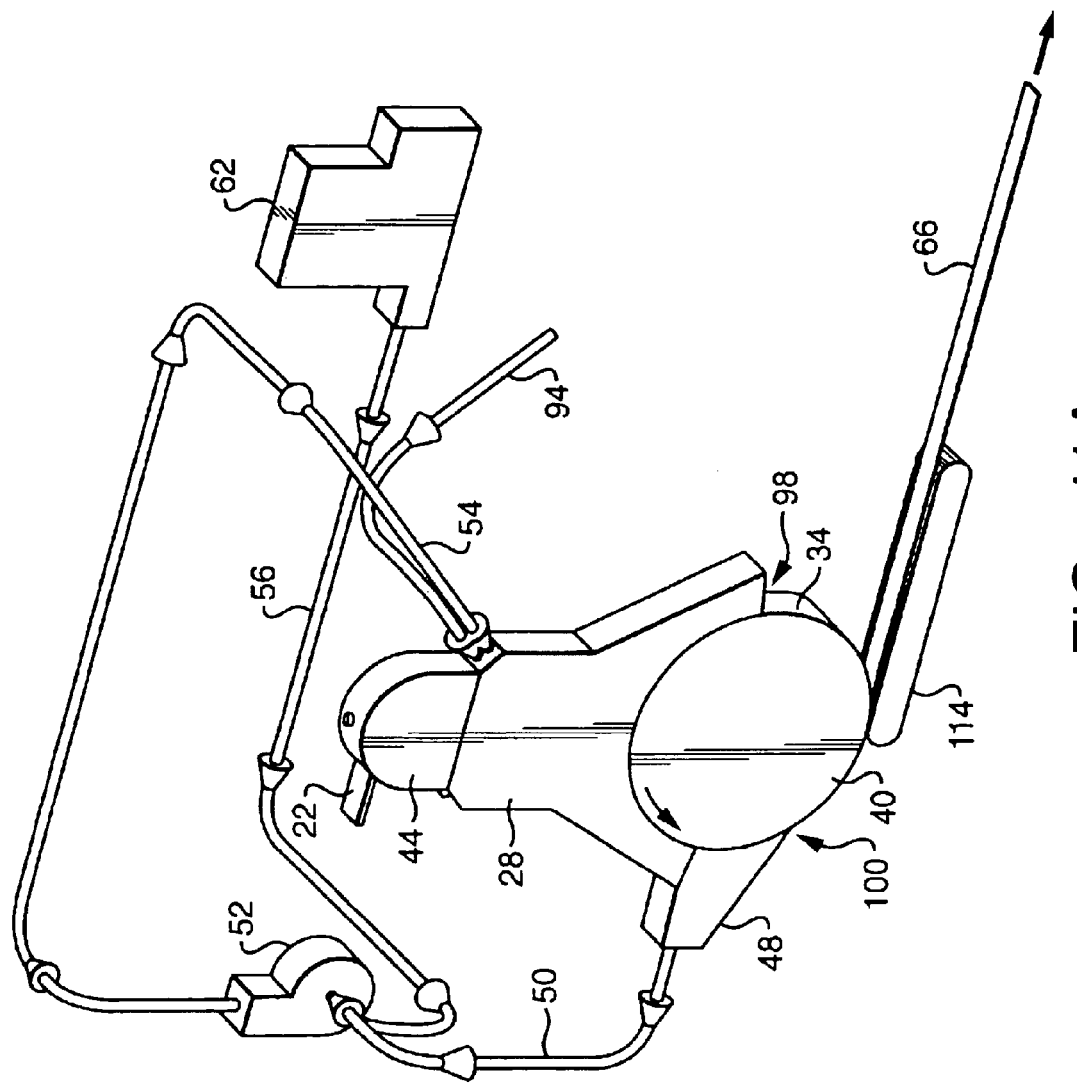
FIG. 11A shows a schematic, perspective view of an alternative forming system which is configured to combine the binder-fiber with scarfed material delivered from a scarfing operation, and introduce the combined binder-fiber and scarfed material into an upstream portion of the forming chamber that is relatively closer to an entrance region of the forming system.

With reference to FIGS. 10A and 11A, the binder-fiber material from the metering feeder 62 can be mixed with the recycled material from the scarfing chamber 48. As representatively shown, the binder-fiber can be combined with the recycled material in the transport blower 52. As a result, the combination of binder-fiber and recycled material can be operatively delivered to the forming chamber 28.

After the scarfing operation, the airformed fibrous layer can be moved to an optional pressure blow-off zone. In the blow-off zone, air can be introduced under pressure and directed radially outwardly against the fibrous layer on the portion of the forming surface that becomes aligned with the blow-off zone. The gas pressure can effect a ready release of the fibrous layer from the forming surface 34, and the fibrous layer 66 can be removed from the forming surface onto a suitable take-off conveyor, such as provided by a system which includes the representatively shown endless conveyor belt 114 disposed about rollers 118. In a particular configuration of the invention, a vacuum suction box 116 can be located below a conveyor belt 114 to help remove the web 66 from the forming surface 34. The vacuum box 116 opens onto the belt 114, and a suction of air out of the vacuum box can draw an air flow through perforations in the conveyor belt. Alternatively, a vacuum transfer roll may be employed. This flow of air can, in turn, operate to draw the web 66 away from the forming surface. The vacuum box can be employed with or without the use of a positive pressure in the blow-off zone. The removed fibrous layer can provide an interconnected series of pads 120, and each pad can have an selected surface contour which substantially corresponds to the contour provided by the corresponding portions of the forming surface 34 upon which each individual pad was formed.

To provide the desired transport operations needed by the various configurations of the invention, any suitable transport mechanism may be employed. Such transport mechanisms can, for example, be provided by transport rollers, conveyor belts, pneumatic conveyors, vacuum conveyors or the like, as well as combinations thereof.

Figure 6:
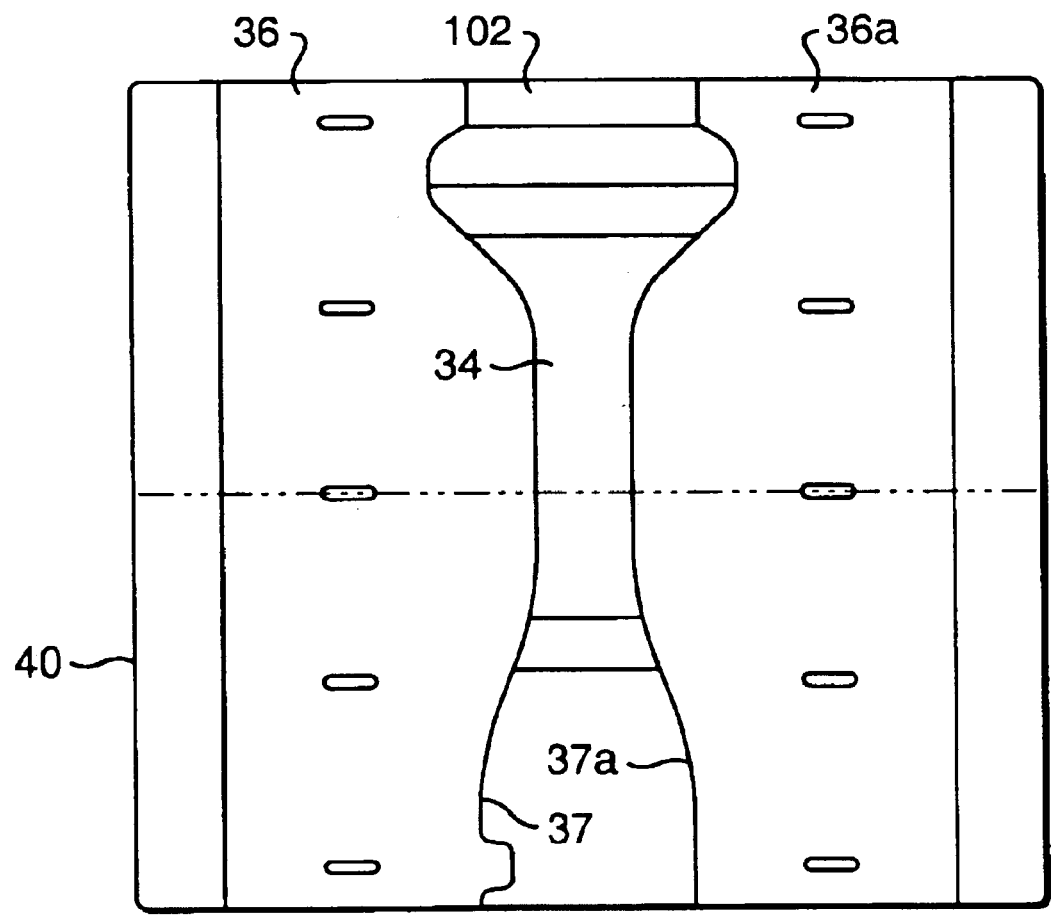
FIG. 6 shows a schematic, top view of a portion of a representative foraminous forming surface that has side-masking members with non-parallel, laterally-shaped and transversely undulating, inboard side walls.
Figure 7:
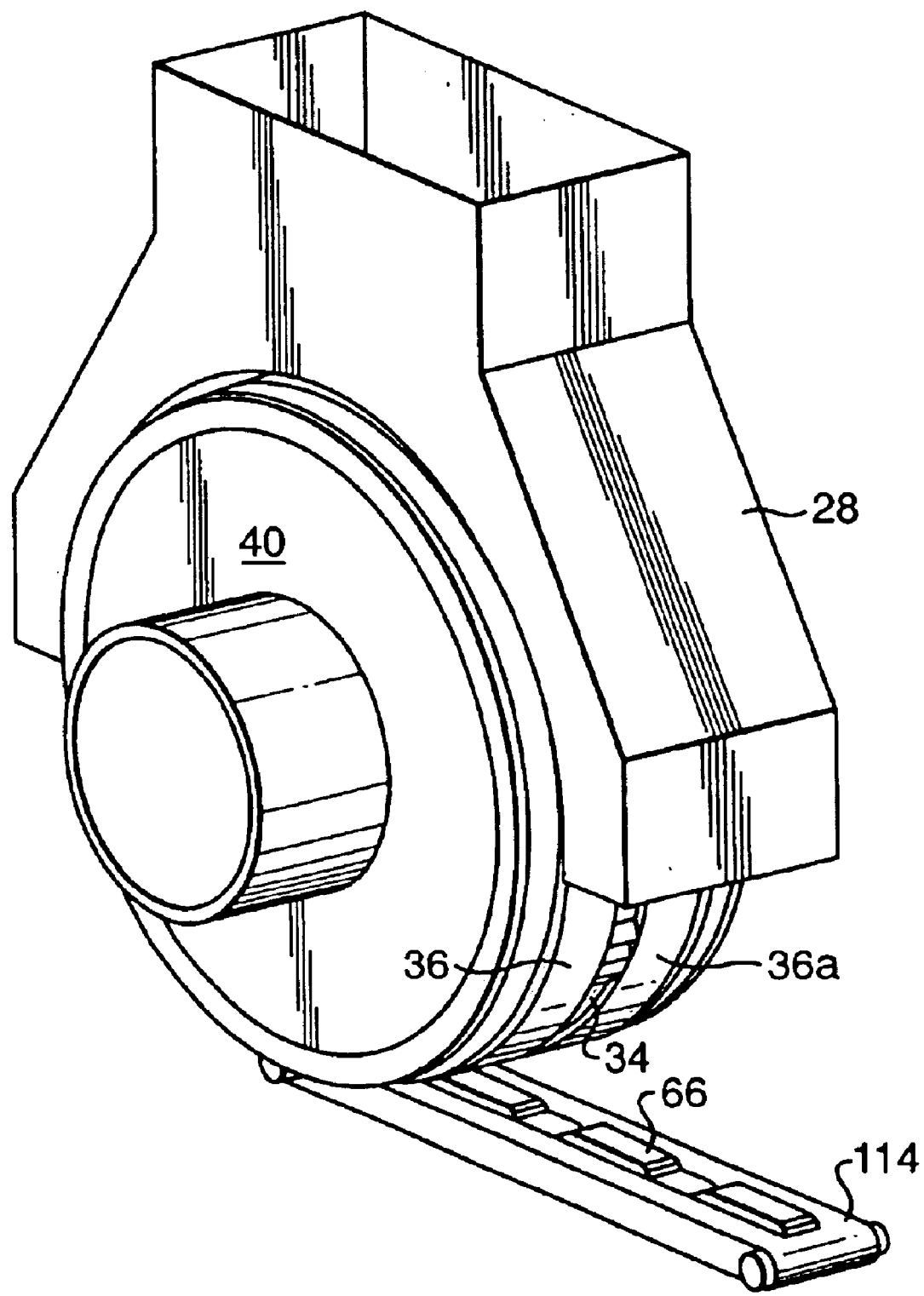
FIG. 7 representatively shows a schematic, perspective view of another representative airforming system that can be employed with the present invention to provide a fibrous layer with generally straight side edge contours.
Figure 8:
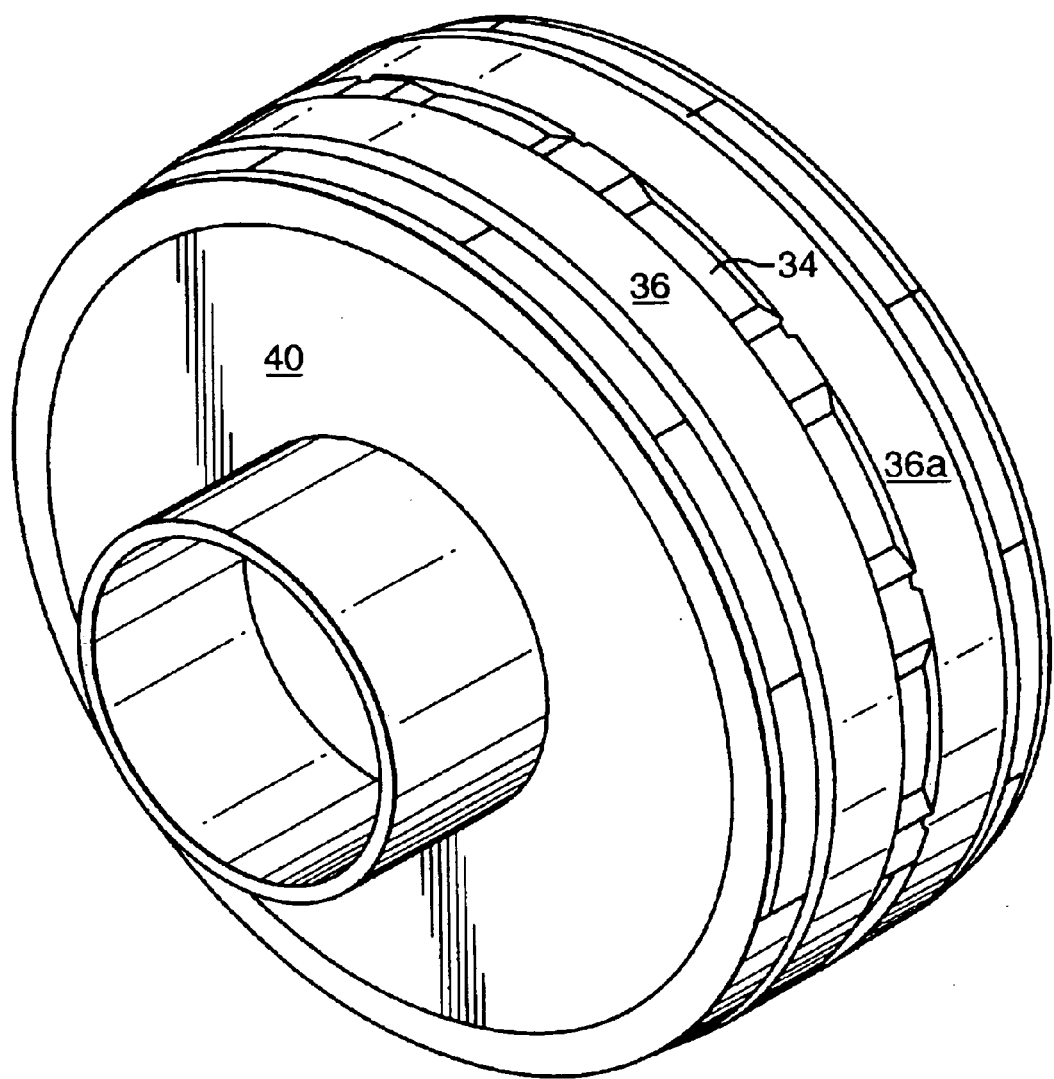
FIG. 8 representatively shows a schematic, perspective view of a forming drum that has been configured to provide a fibrous layer having generally parallel and generally straight side edge contours.
Figure 9:
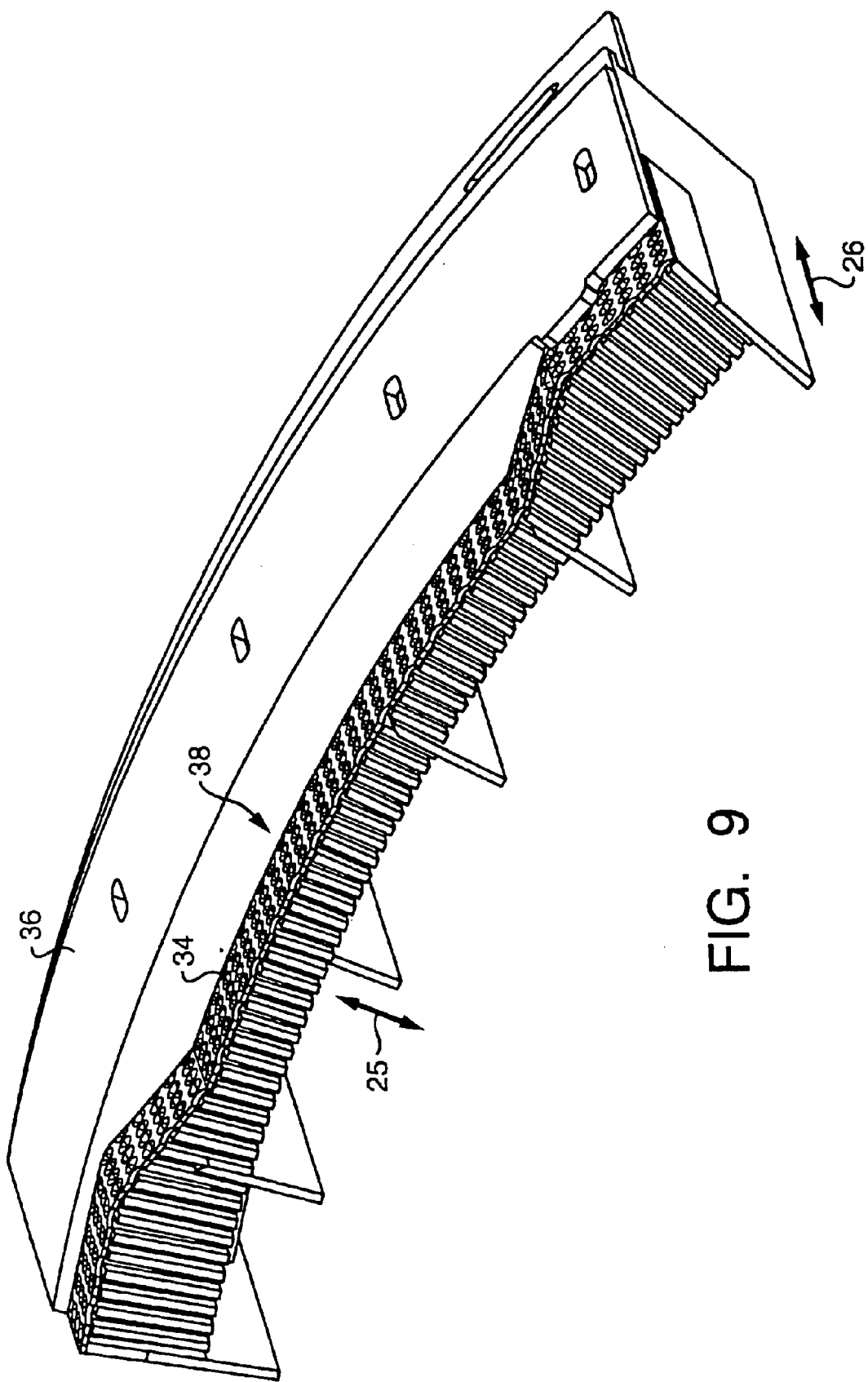
FIG. 9 shows a schematic, perspective view of a longitudinal cross-section through a portion of a representative forming surface which has been configured with a varying depth-wise contour, and can be employed to form a fibrous layer having a varying, depth contour.

As representatively shown in FIGS. 4 and 5, the forming surface 34 can be provided along the outer cylindrical surface of the forming drum 40, and can extend along the axial (cross-directional) and circumferential (machine-directional) dimensions of the forming drum. With reference to FIGS. 6, 8 and 9, the structure of the forming surface can be composed of an assembly, and can include a selected foraminous member which is operatively located on and secured to the forming drum 40. The foraminous member may include a screen, a wire mesh, a hard-wire cloth, a perforated member or the like, as well as combinations thereof. In a particular aspect, the foraminous member can include a fluted member having open channels which can extend generally radially and can allow a substantially free flow of air or other selected gas from the outward-side of the drum towards the center of the drum. The flutes or channels can have any desired cross-sectional shape, such as circular, oval, hexagonal, pentagonal, other polygonal shape or the like, as well as combinations thereof. The fluted foraminous member can, for example, have a fluted structure in which the channels are arranged to have a rectangular cross-sectional shape. Such honeycomb structures are well known in the art, and can be composed of various materials, such as plastic, metal, ceramics and the like, as well as combinations thereof. For example, suitable materials and structures are available from FT and D International, Ltd., a business having offices located in Lula, Ga., U.S.A.

In a desired feature of the invention, the radially outward surface of the fluted member or other foraminous member can be configured with a selected depth-wise, surface contour. Accordingly, the forming surface 34 can be configured to include a depth contour 38. The contoured surface regions of the foraminous member can be formed to have any operative shape. In desired arrangements, the contour shape can be trapezoidal. Alternatively, the contour shape can be domed or flat. In a particular arrangement, the depth contour 38 can be provided by forming one or more pocket regions that are selectively distributed along the circumferential length of the forming surface 34. The depth contour 38 can alternatively be provided by incorporating a scalloped scarfing roll, a shaped scarfing roll, a timed scarfing roll or the like, as well as combinations thereof.

The surface contour can be formed and distributed along the axial and circumferential dimensions of the foraminous member, and can be configured to have a non-constant, contoured depth. In the shown arrangement, the contoured depth can extend radially into or out of the z-directional thickness of the foraminous member, and can be configured to provide a desired variation in thickness of the formed fibrous layer 66. In desired arrangements, the variation in the z-directional surface contour can have a selected pattern, and the pattern may be regular or irregular in configuration. For example, the pattern of the surface contour can be configured to substantially provide a selected repeat-pattern along the circumferential dimension of the forming drum. The surface contour of the foraminous member can have one or more regions with a first average depth, and can further have one or more regions with a relatively greater second average depth. Each region with the first average depth can provide a lower-basis-weight region of the forming surface, and each region with the greater second depth can provide a relatively higher-basis-weight region of the forming surface. Desirably, each region with the first average depth can be substantially contiguous with an adjacent region with the greater second depth. Each low-basis-weight region can be employed to form a relatively lower-basis-weight portion or section of the fibrous layer 66, and each higher-basis-weight region can be employed to form a relatively higher-basis-weight portion or section of the fibrous layer 66. Subsequently, each lower-basis-weight section of the fibrous layer can be employed to form a relatively lower-basis-weight section of an individual fibrous pad 120, and each higher-basis-weight section of the fibrous layer can be employed to form a relatively lower-basis-weight section of such individual fibrous pad 120.

In a particular feature, the foraminous member can have a z-directional contour pattern 38 which may include compound curvatures, or may be substantially free of compound curvatures. For example, the contour pattern of the foraminous member can be configured to have a z-directional contour which varies depth-wise along the longitudinal direction 24. Additionally, the z-directional contour pattern along the surface of the foraminous member may provide a varying depth, or may provide a substantially constant depth with respect to the lateral cross-direction 26.

In a further aspect, one or more non-flow regions of the forming drum surface may be operatively formed by employing any suitable blocking mechanism that can cover or otherwise occlude the flow of gas through selected regions of the forming surface. As a result, the blocking mechanism can deflect or reduce the amount of fibers deposited on the areas of the forming surface that are covered by the blocking mechanism. To provide a desired fibrous layer 66, the forming surface 34 can include side side-masking members or contour rings 36, which are configured to provide a desired side-edge shaping to the fibrous layer 66. The side-edge shaping of the fibrous layer can alternatively be provided by cutting and removal, cutting and folding, or the like, as well as combinations thereof.

The blocking mechanism can optionally be configured to form other desired elements, such as a series of key notches on the laid fibrous layer 66. The key notches can, for example, provide sensing point for locating and positioning a subsequent severing of the longitudinally extending fibrous layer into discrete fibrous pads 120.

With reference to FIGS. 3, 5 and FIGS. 7 through 9, the forming surface 34 can have disposed thereon at least one side-masking member 36. Desirably, the invention can include a cooperating system side-masking members 36 and 36a. In the representatively shown configuration, the side-masking members can be provided by a pair of laterally opposed ring members which extend circumferentially around the forming drum 40. In desired arrangements, the side-masking members can be selectively shaped and contoured, and can be configured to provide opposed, symmetrically arranged contour rings. Each of the contour rings can have a cross-directional extent that is varied in a selected pattern to provide a laterally varying, inboard side contour. In particular arrangements the side contours in the first and second ring members can be substantial mirror-images of each other. In another feature, at least one ring member, can include one or more key tabs. The individual key tabs may, for example, be employed for marking or otherwise identifying each intended article length along the circumference of the forming drum. Such contour rings can be particularly advantageous when the forming drum system is employed to produce absorbent pads for use in disposable, shaped absorbent articles, such as diapers, children's training pants, feminine care products, adult incontinence products and the like. The contour rings or other side-masking members can be configured to substantially prevent a deposition of fibers in selected regions along the side margins of the forming surface 34 to thereby form corresponding arcuate, cut-out sections along the side regions of the airformed fibrous layer 66.

The side wall edges 37 and 37a of the contour rings 36 and 36a can have a substantially straight configuration along the machine direction 24 to produce a substantially rectangular, ribbon shaped fibrous layer 66. In other desired arrangements, the inboard side walls 37 and 37a of the ring members 36 and 36a can be shaped and contoured along the cross-direction 26 (e.g. FIGS. 3 and 6). In the representatively shown arrangement, the side walls of the contoured ring members can have a serpentine contour, which extends along the circumferential, machine-direction, and undulates along the cross-direction. Additionally, the first and second contour rings 36 and 36a can be cooperatively arranged and configured to provide alternating, narrow and wider regions of the forming surface 34.

Accordingly, the fibrous layer 66 delivered from the forming drum and scarfing chamber can include contoured side edges 72. Additionally, the fibrous layer can have a varying, non-constant depth contour 74, as representatively shown in FIG. 21. The contoured depth 74 can vary when moving along the machine-direction of the fibrous layer 66. Additionally, the depth contour 74 of the fibrous layer can vary when moving along the cross-direction of the fibrous layer.

In another aspect of the method and apparatus, the discrete fibrous articles 120 can be directly formed on forming surface 34. As representatively shown in FIGS. 6 and 20C, a plurality of blocking end-masking members 102 can be located at selected locations along the circumference of the forming surface 34. The end-masking members 102 can interconnect between the side-masking members 36 and 36a, and can extend along the axial and circumferential dimensions of the forming drum 40. The end-masking members can also overlie the forming surface 34 and can block the accumulation of fibers along relatively narrow, transverse portions of the forming surface. As a result, the deposition of fibers onto forming surface 34 can create a substantially non-continuous web which includes a serial plurality of individual, discrete fibrous articles, such as the discrete pads 120.

The end-masking members 102 can have a substantially rectilinear shape or a selected non-rectilinear shape. In a particular aspect, the end-masking members 102 can be selectively contoured along the cross-direction 26 to provide transverse end-edges with desired combinations of linear and/or curvilinear shapes.

The cross-directional width of the fibrous layer 66 that is delivered from the forming drum 40 can be at least a minimum of about 1 cm. The web width can alternatively be at least about 1.5 cm, and can optionally be at least about 2 cm to provide improved performance. In other aspects, the web width can be up to a maximum of about 75 cm, and may be up to 100 cm, or more. The web width can alternatively be up to about 62 cm, and can optionally be up to about 50 cm to provide desired performance.

The method and apparatus can be configured to provide a fibrous web or layer 66 having an average total basis weight which is at least a minimum of about 100 g/m². The average basis weight can alternatively be at least about 200 g/m², and can optionally be at least about 300 g/m² to provide improved performance. In other aspects, the average total basis weight can be up to a maximum of about 2500 g/m², or more. The average basis weight can alternatively be up to about 2000 g/m², and can optionally be up to about 1500 g/m² to provide improved performance. The basis weight may be non-uniformly distributed along the fibrous layer, or may be substantially uniformly distributed, as desired.

Where the method and apparatus have been configured to direct superabsorbent material into the forming chamber 28, the airformed fibrous layer 66 can include an amount of superabsorbent material which is at least a minimum of about 1 wt %, as determined with respect to the total weight of the fibrous layer. The amount of superabsorbent material can alternatively be at least about 2 wt %, and can optionally be at least about 3 wt % to provide improved performance. In other aspects, the amount of superabsorbent material can be up to a maximum of about 95 wt %, or more. The amount of superabsorbent material can alternatively be up to about 85 wt %, and can optionally be up to about 75 wt % to provide desired benefits.

Figure 19:
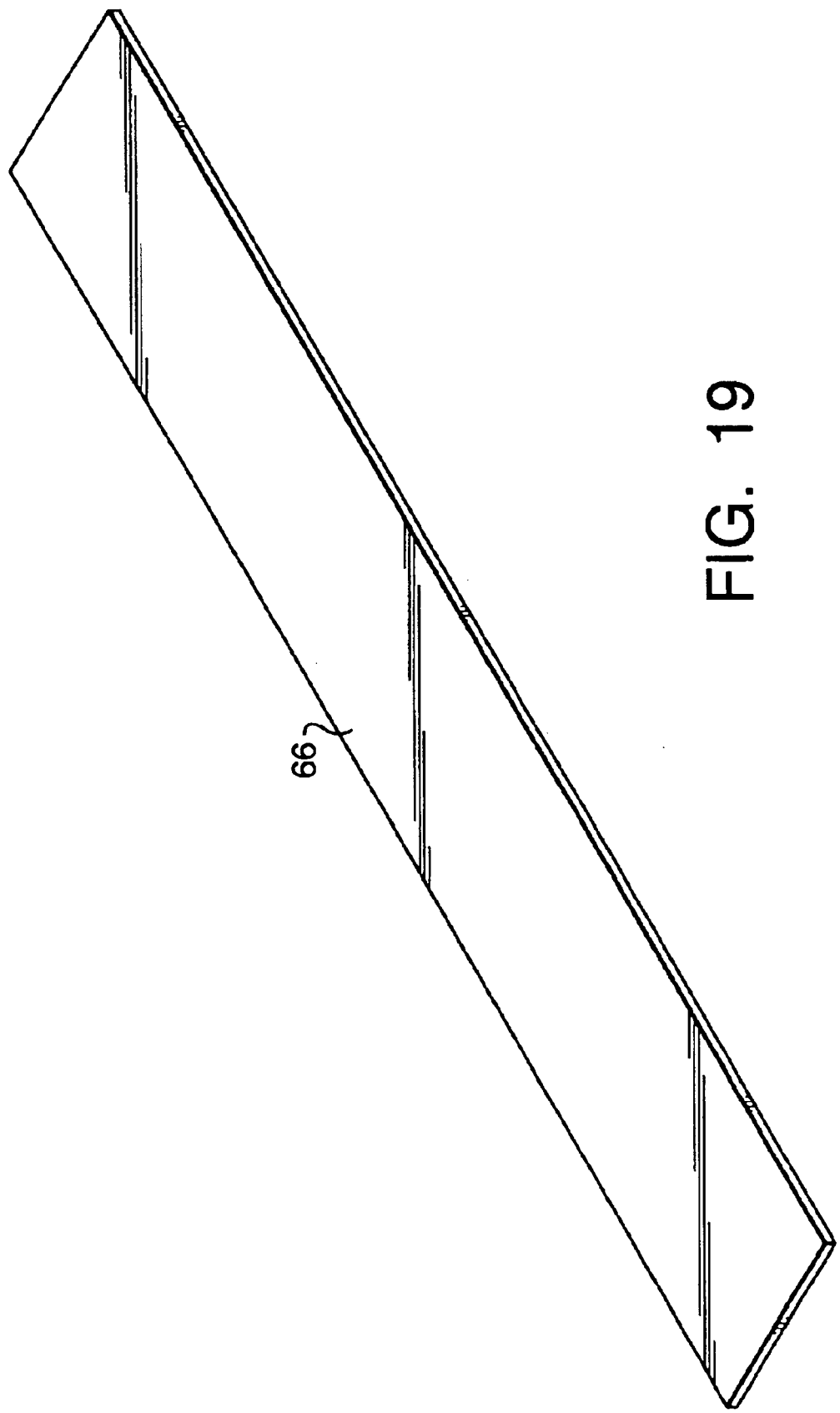
FIG. 19 shows a perspective view of a representative length of a substantially continuous fibrous layer which has been formed with substantially non-contoured side edge regions and with a substantially non-contoured thickness dimension.
Figure 19A:
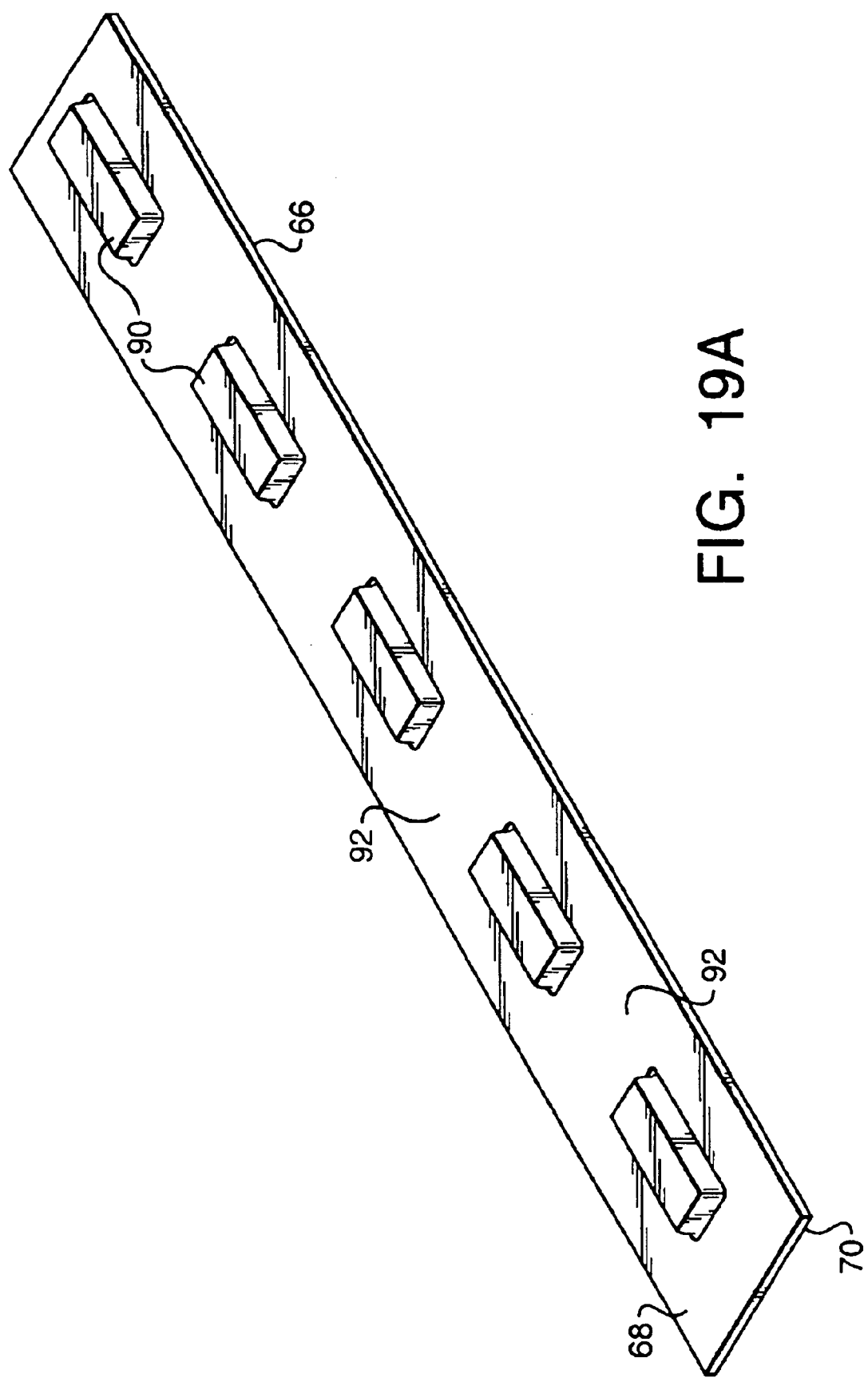
FIG. 19A shows a perspective view of a representative length of a substantially continuous fibrous layer which has been formed with substantially non-contoured side edge regions and with a selectively contoured thickness dimension.

The fibrous layer 66 can be configured to have a non-constant, contoured basis weight with one or more high-basis-weight regions 90, and one or more low-basis-weight regions 92 (e.g. FIG. 19A. In at least one high-basis-weight region, at least a significant portion of the z-contoured fibrous layer can have a composite basis weight which is at least about 500 g/m². The high-basis-weight region can alternatively have a basis weight of at least about 600 g/m², and can optionally have a basis weight of at least about 700 g/m² to provide improved performance. In other aspects, the high-basis-weight region of the fibrous layer 66 can have a composite basis weight of up to about 2500 g/m², or more. The high-basis-weight region can alternatively have a basis weight of up to about 2000 g/m², and can optionally have a basis weight of up to about 1500 g/m² to provide desired performance.

Additionally, in at least one low-basis-weight region, at least a significant portion of the z-contoured fibrous layer can have a composite basis weight is at least about 50 g/m². The low-basis-weight region can alternatively have a basis weight of at least about 100 g/m², and can optionally have a basis weight of at least about 150 g/m² to provide improved performance. In other aspects, the low-basis-weight region of the fibrous layer 66 can have a composite basis weight of up to about 1500 g/m², or more. The low-basis-weight region can alternatively have a basis weight of up to about 1200 g/m², and can optionally have a basis weight of up to about 1000 g/m² to provide desired performance.

In another aspect, the fibrous layer 66 can include an amount of binder-fibers which is the amount of binder-fibers can be at least a minimum of about 0.5 wt %, as determined with respect to the total weight of the fibrous layer 66. The amount of binder-fibers can alternatively be at least about 1 wt %, and can optionally be at least about 2 wt % to provide improved performance. In other aspects, the amount of binder-fibers can be up to a maximum of about 40 wt %, or more. The amount of binder-fibers can alternatively be up to about 30 wt %, and can optionally be up to about 20 wt % to provide an improved performance.

In a further aspect, the fibrous layer 66 prior to any debulking can be configured to have a density which is at least a minimum of about 0.01 g/cm³, as determined at a restraining pressure of 1.38 KPa (0.2 psi). The density can alternatively be at least about 0.02 g/cm³, and can optionally be at least about 0.03 g/cm³ to provide improved performance. In other aspects, the density of the fibrous layer 66 can be up to a maximum of about 0.12 g/cm³, or more. The density can alternatively be up to about 0.11 g/cm³, and can optionally be up to about 0.1 g/cm³ to provide improved effectiveness.

With reference to FIG. 19, the method and apparatus can be configured to produce a substantially flat fibrous layer 66 which extends substantially continuously along its lengthwise, machine-direction 24. The fibrous layer may be formed with substantially non-contoured, generally straight side edge regions, and with a substantially non-contoured thickness dimension. Additionally, the fibrous layer may have a substantially uniform basis weight distribution.

In an alternative arrangement, the method and apparatus can be configured to produce a substantially continuous fibrous layer 66 which has been formed with substantially non-contoured side edge regions and with a selectively contoured thickness dimension (e.g. FIG. 19A). Accordingly, portions of the fibrous layer can have a relatively lower thickness, and other portions of the fibrous layer can have a relatively higher thickness. Additionally, portions 92 of the fibrous layer can have a relatively lower basis weight, and other portions 90 of the fibrous layer can have a relatively higher basis weight.

Figure 19B:
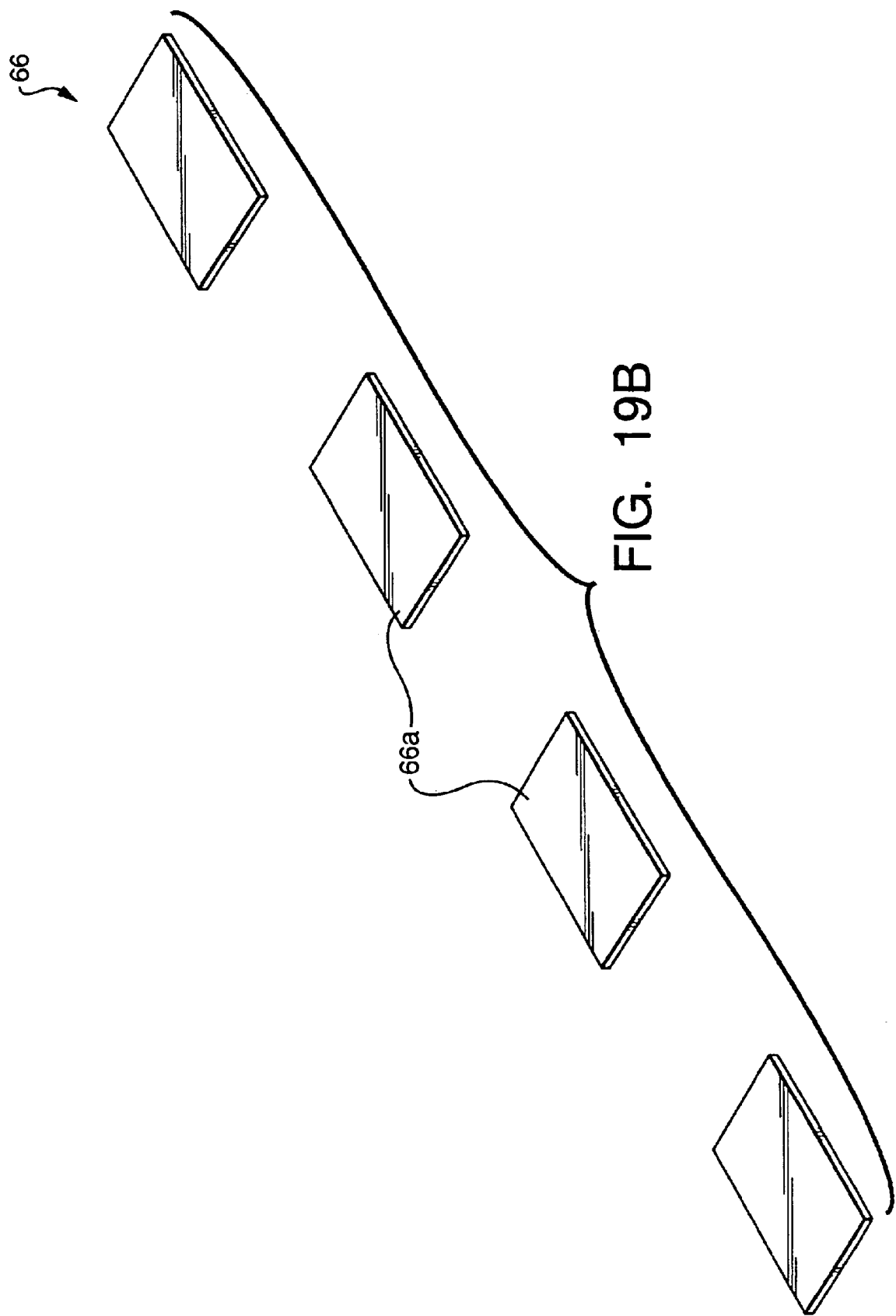
FIG. 19B representatively shows a schematic, perspective view of a representative length of a discontinuous fibrous layer which has been formed with substantially non-contoured side edge regions and with a substantially non-contoured thickness dimension.

With reference to FIG. 19B, the method and apparatus can be configured to produce a discontinuous fibrous layer 66 which includes a serial plurality of separated web portions or segments 66a distributed along the machine-direction. The separated portions of the discontinuous fibrous layer can each be formed with substantially non-contoured, generally straight and generally parallel side edge regions. Additionally, each of the separated portions of the formed web can have a generally flat, and substantially non-contoured thickness dimension.

Figure 19C:
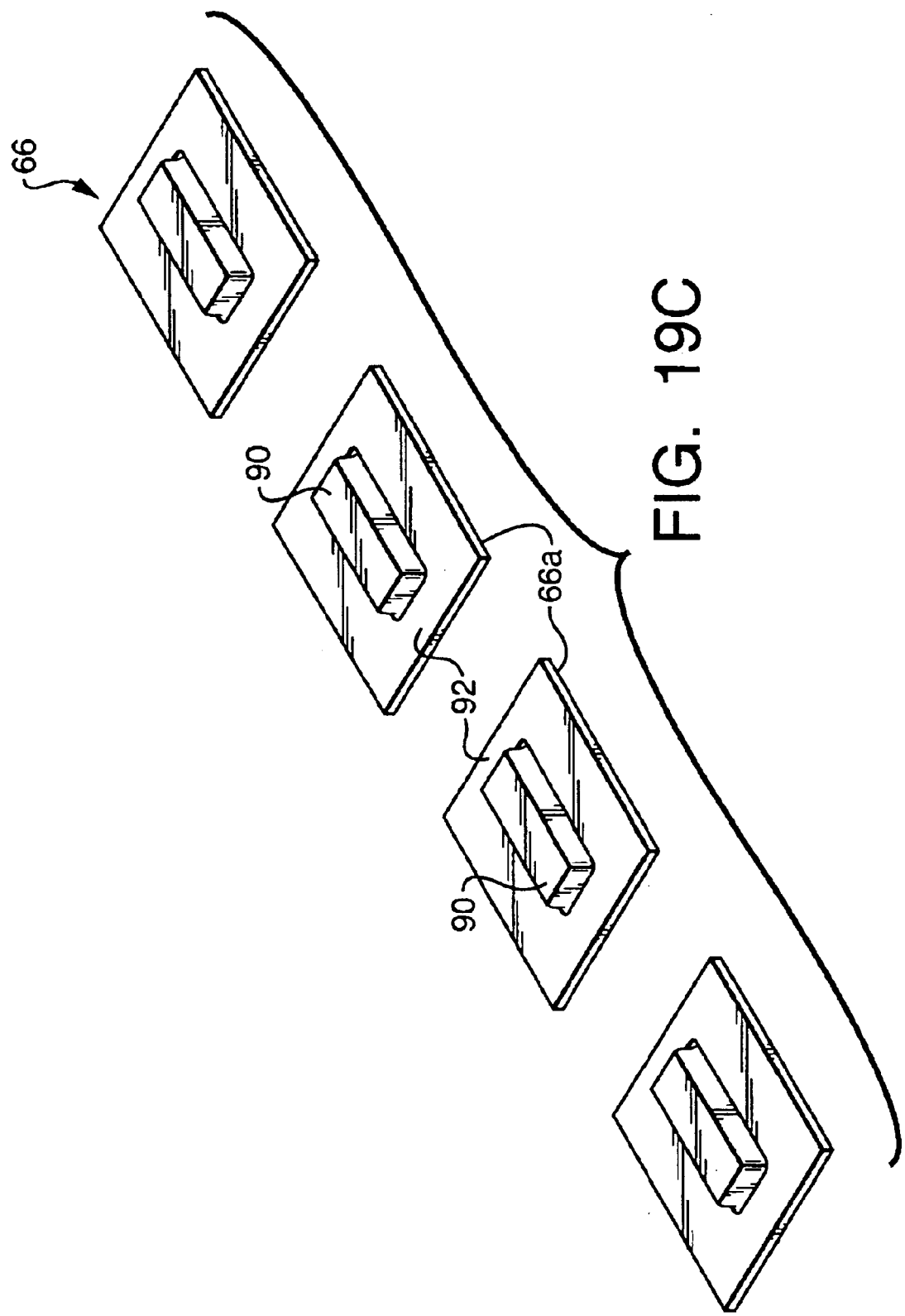
FIG. 19C representatively shows a schematic, perspective view of a representative length of a discontinuous fibrous layer which has been formed with substantially non-contoured side edge regions and with a selectively contoured thickness dimension.

In another arrangement, the method and apparatus can be configured to produce a discontinuous fibrous layer which has been formed with substantially non-contoured side edge regions and with a selectively contoured thickness dimension (e.g. FIG. 19C). Each separated portion of the discontinuous fibrous layer can have a relatively-lower thickness region, and a relatively-higher thickness region. Additionally, each separate portion of the discontinuous fibrous layer can have a relatively-lower basis weight region, and a relatively-higher basis weight region.

Figure 20:
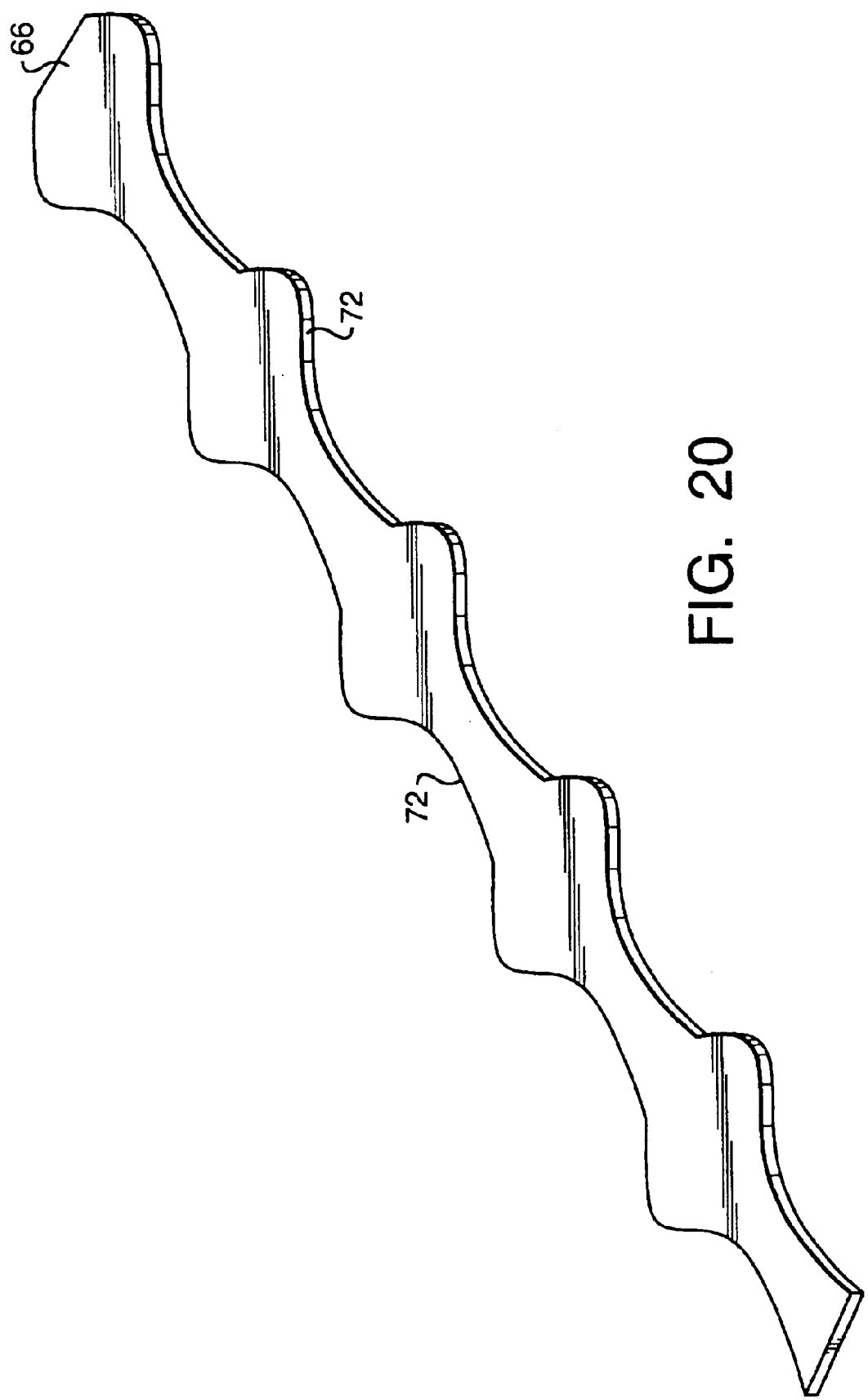
FIG. 20 shows a perspective view of a representative length of a substantially continuous fibrous layer which has been formed with selectively contoured side edge regions and with a substantially non-contoured thickness dimension.

With reference to FIG. 20, the method and apparatus can be configured to produce a substantially continuous fibrous layer 66 which has been formed with selectively contoured side edge regions 72 and with a substantially non-contoured thickness dimension. The side edge regions of the fibrous layer can be laterally contoured with a selected, undulating, serpentine outline shape.

Figure 20A:
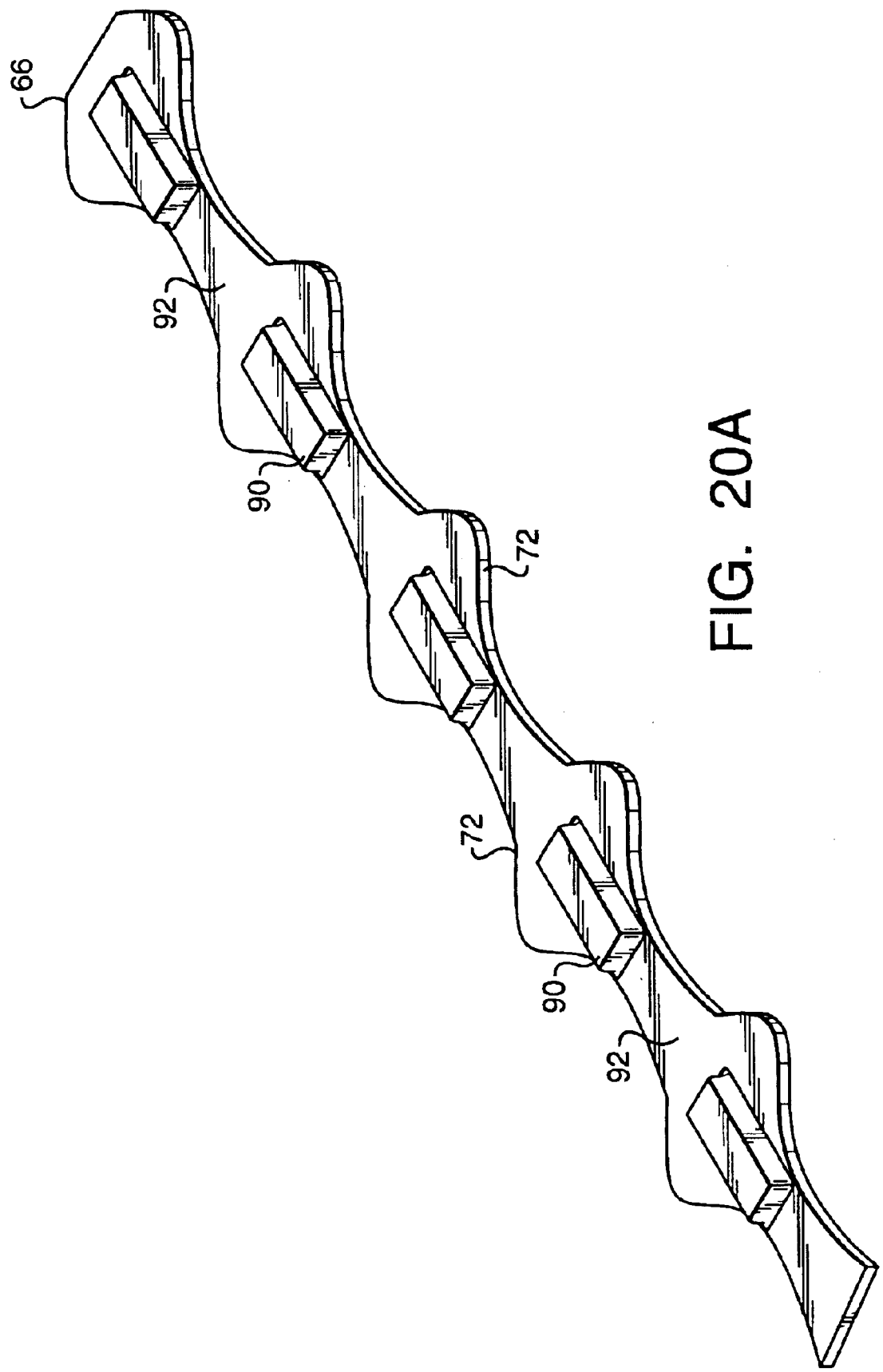
FIG. 20A shows a perspective view of a representative length of a substantially continuous fibrous layer which has been formed with selectively contoured side edge regions and with a selectively contoured thickness dimension.

In an alternative arrangement, the method and apparatus can be configured to produce a substantially continuous fibrous layer which has been formed with selectively contoured side edge regions and with a selectively contoured thickness dimension (e.g. FIG. 20A). Accordingly, predetermined portions of the fibrous layer can have a relatively lower thickness, and other portions of the fibrous layer can have a relatively higher thickness. Additionally, portions 92 of the fibrous layer can have a relatively lower basis weight, and other portions 90 of the fibrous layer can have a relatively higher basis weight.

Figure 20B:
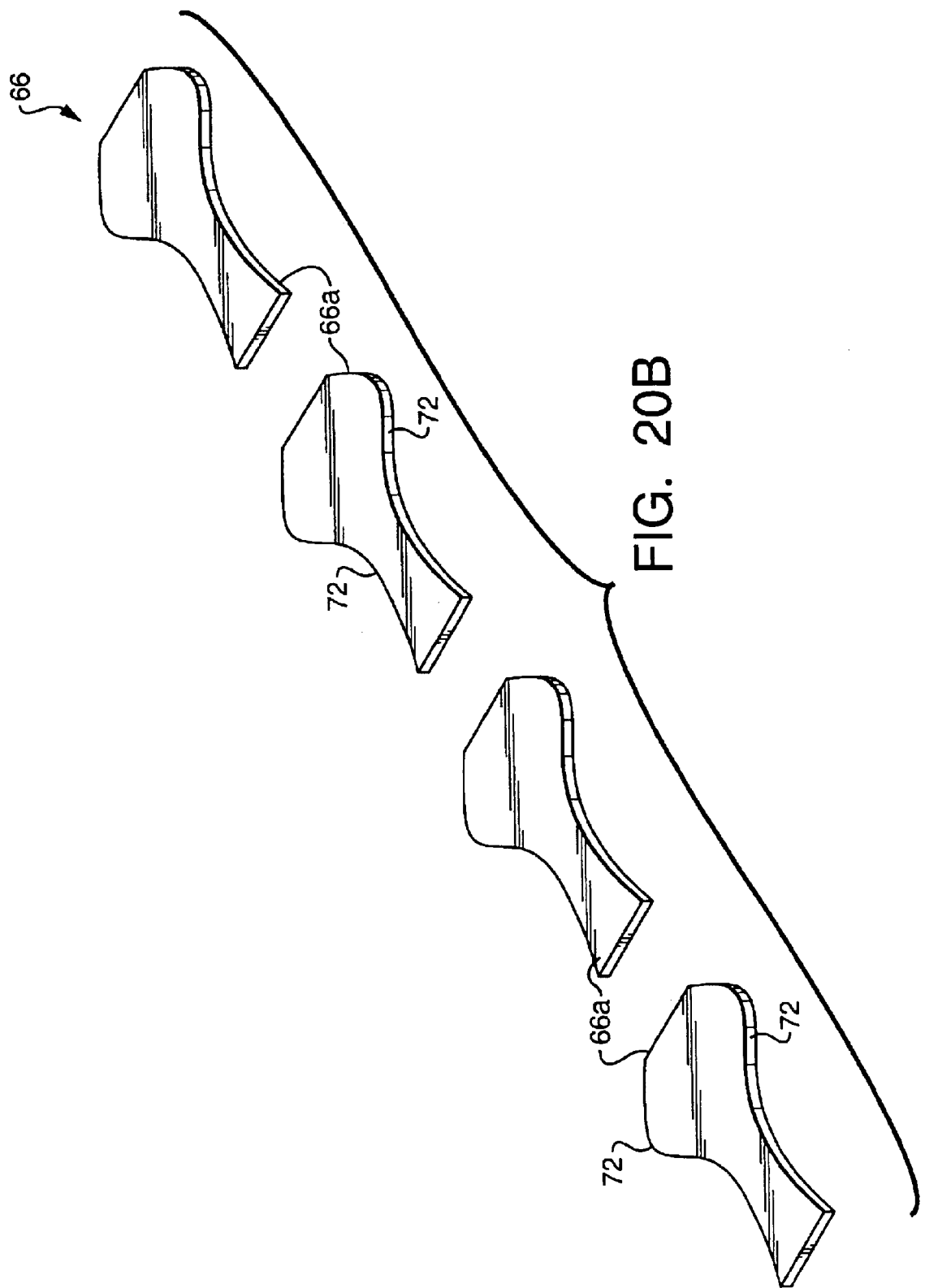
FIG. 20B shows a perspective view of a representative length of a discontinuous fibrous layer which has been formed with selectively contoured side edge regions and with a substantially non-contoured thickness dimension.

With reference to FIG. 20B, the method and apparatus can be configured to produce a discontinuous fibrous layer 66 which includes a serial plurality of separated web portions or segments. The separated portions of the discontinuous fibrous layer can each be formed with laterally shaped side edge regions. Additionally, each of the separated web portions can be formed and with a generally flat and substantially non-contoured thickness dimension.

Figure 20C:
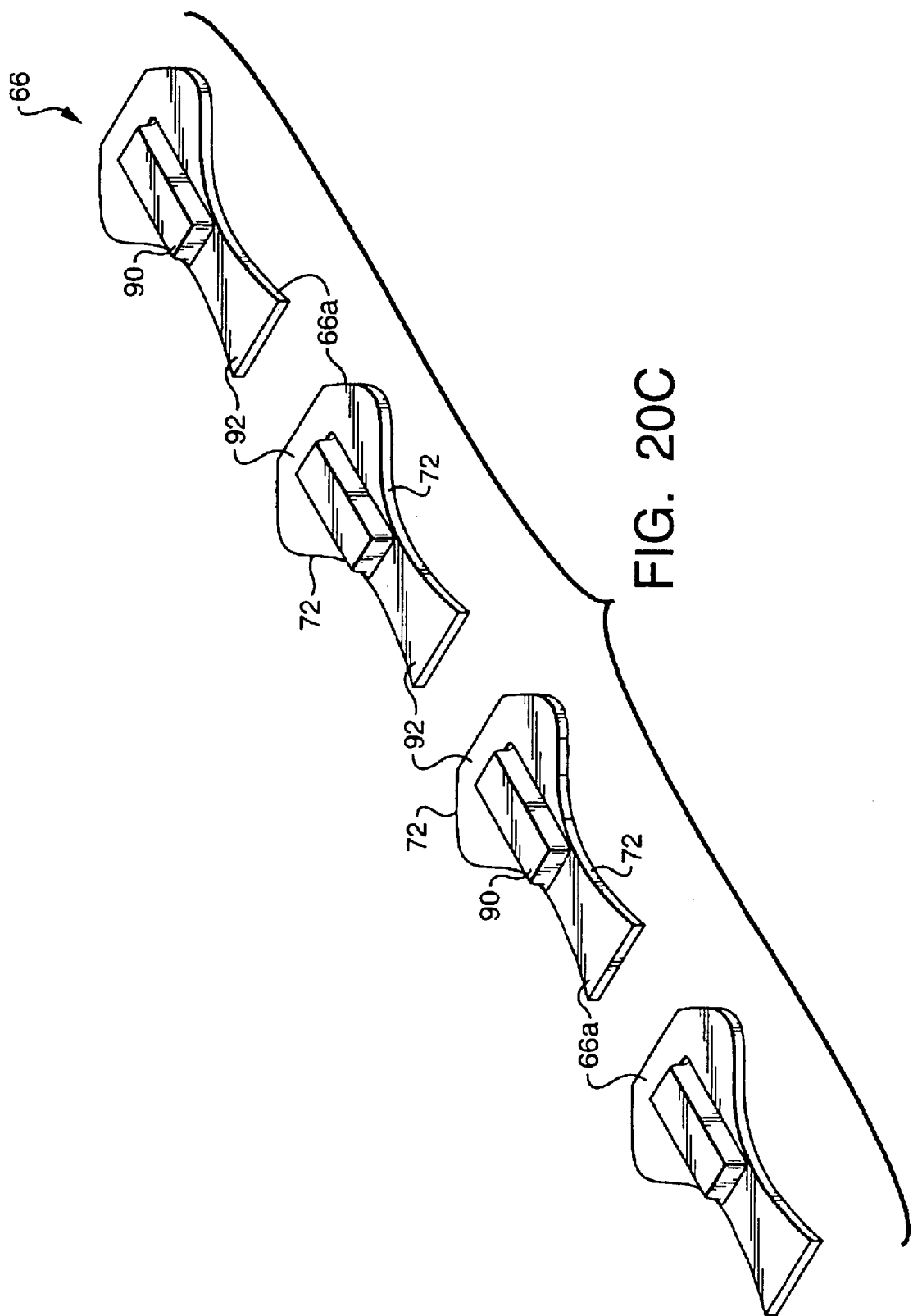
FIG. 20C shows a perspective view of a representative length of a discontinuous fibrous layer which has been formed with selectively contoured side edge regions and with a selectively contoured thickness dimension.

In still another arrangement, the method and apparatus can be configured to produce a discontinuous fibrous layer which has been formed with selectively contoured side edge regions and with a selectively contoured thickness dimension (e.g. FIG. 20C). Accordingly, predetermined regions of each laterally shaped segment of the discontinuous fibrous layer can have a relatively lower thickness, and other regions of each laterally shaped segment of the fibrous layer can have a relatively higher thickness. Additionally, predetermined regions of each laterally shaped segment of the discontinuous fibrous layer can have a relatively lower basis weight, and other regions of each segment of the discontinuous fibrous layer can have a relatively higher basis weight.

In still another aspect of the method and apparatus, the fibrous layer 66 can be delivered from the forming drum 40, and can be directed through the activation system 104 at a selected web speed. In particular, the fibrous layer can be directed through the activation chamber 80 at the selected web speed. The speed of the fibrous layer can be at least a minimum of about 0.5 m/sec. The web speed can alternatively be at least about 1 m/sec, and can optionally be at least about 2 m/sec to provide improved performance. In other aspects, the web speed can be up to a maximum of about 10 m/sec, or more. The web speed can alternatively be up to about 8 m/sec, and can optionally be up to about 7 m/sec to provide improved effectiveness.

In a further aspect, the cross-directional width of the fibrous layer 66 that is delivered from the forming drum 40 can substantially correspond to a maximum of about 10 article dimensions. In a desired configuration, the cross-directional width of the fibrous layer 66 can substantially correspond to a selected, single-article dimension.

The selected, single-article dimension can, for example, substantially correspond to the cross-directionally aligned, "width" dimension of a selected absorbent body, as observed when the absorbent body is assembled in a manufacturing process to provide a final end-article product. Alternatively, the selected single-article dimension can substantially correspond to the cross-directionally aligned "length" dimension of a selected absorbent body, as observed when the absorbent body is assembled in a manufacturing process to provide a final end-article product. It should be readily appreciated that such end-article products can, for example, include infant diapers, feminine care articles, incontinence articles, incontinence garments, children's training pants, absorbent pads, or the like.

After the fibrous layer 66 departs the forming chamber 28, the fibrous layer can be subjected to a scarfing operation to remove excess material and provide a desired basis weight distribution within the fibrous layer 66. The scarfing system can include a scarfing chamber 48, and a scarfing roll 46 which is operatively positioned within the scarfing chamber. The scarfing systems are conventional and well known in the art, and are readily available from commercial vendors.

In a particular feature, the fibrous layer 66 may be selectively pre-compressed prior to a subsequent activation of the binder-fibers. Accordingly, the fibrous layer 66 may be selectively pre-compressed prior to delivering the pre-compressed web into the activation chamber 80. The pre-compressed web 66 can have a density which is at least a minimum of about 0.01 g/cm³, as determined under a restraining pressure of 1.38 KPa (0.2 psi). The pre-compressed web density can alternatively be at least about 0.02 g/cm³, and can optionally be at least about 0.03 g/cm³ to provide improved performance. In other aspects, the pre-compressed web density can be up to a maximum of about 0.5 g/cm³, or more. The pre-compressed web density can alternatively be up to about 0.45 g/cm³, and can optionally be up to about 0.4 g/cm³ to provide improved effectiveness.

In another aspect of the method and apparatus, the fibrous layer 66 may be selectively preheated prior to entering the activation chamber 80. The preheating of the fibrous layer 66 can increase a dielectric loss tangent of the web materials, and can allow a more efficient absorption of energy.

For example, a preheater device can be positioned relatively upstream from and prior to the activation chamber 80. The preheater may include a microwave heater, a radiant heater, a convection heater, a through-air heater, an infrared heater, a frictional heater or the like, as well as combinations thereof.

Alternatively, the binder-fibers may be preheated before the binder-fibers are combined with the absorbent fibers and superabsorbent material. For example, the binder-fibers may be preheated at the metering device 62, and/or at some point during the transport of the binder-fibers through the binder-fiber delivery conduit 56. Such arrangement can help reduce the amount of cooling needed prior to the debulking of the stabilized layer 86. Among other advantages, an increase of the dielectric loss tangent of the web materials can be restricted to the binder-fibers, thereby improving the efficiency of the activation system.

After the fibrous layer 66 is removed from the forming drum 40, an operative web transporter can deliver the fibrous layer to a binder activation system 104. In a particular aspect, the binder activation system can be configured to employ high-frequency, electromagnetic, radiant energy. In another aspect, the binder activation system can employ radio-frequency (RF) energy having an RF frequency which is at least a minimum of about 0.3 megahertz (MHz). The frequency can alternatively be at least about 300 MHz, and can optionally be at least about 850 MHz to provide improved performance. In other aspects, the frequency can be up to a maximum of about 300,000 MHz, or more. The frequency can alternatively be up to about 30,000 MHz, and can optionally be up to about 2,600 MHz to provide desired effectiveness.

The RF energy can be produced by a suitable generator. For example, a suitable microwave generator 76 can produce an operative amount of microwave energy, and can direct the energy through a suitable wave-guide 78 to an activation chamber 80. As representatively shown in FIG. 14, the activation chamber can include a housing 126 which operatively connects to the wave-guide 78, and the housing can include end walls 128. Additionally, the housing can include a entrance opening 82 (e.g. FIG. 15) for admitting the fibrous layer into the activation chamber, and an outlet opening 84 for exiting the fibrous layer from the activation chamber. The entrance and exit openings can be suitably sized and configured to allow an operative movement of the fibrous layer into and out of the activation chamber while also avoiding an excessive leakage of energy from the activation chamber. It should be readily apparent that the various RF components (e.g. the wave-guide and activation chamber) can be constructed with suitable non-ferrous, electrically-conductive materials, such as aluminum, copper, brass, bronze, gold and silver, as well as combinations thereof.

The activation chamber 80 can be a tuned chamber within which the RF energy can produce an operative standing wave. In a particular feature, the activation chamber can be configured to be a resonant chamber. Examples of suitable arrangements for the resonant, activation chamber system are described in a U.S. Pat. No. 5,536,921 entitled SYSTEM FOR APPLYING MICROWAVE ENERGY IN SHEET-LIKE MATERIAL by Hedrick et al. which has an issue date of Jul. 16, 1996; and in U.S. Pat. No. 5,916,203 entitled COMPOSITE MATERIAL WITH ELASTICIZED PORTIONS AND A METHOD OF MAKING THE SAME by Brandon et al which has a issue date of Jun. 29, 1999. The entire disclosures of these documents are incorporated herein by reference in a manner that is consistent herewith.

In another feature, the effectiveness of the activation chamber 80 can be determined by measuring the power that is reflected back from the activation impedance load provided by the combination of the activation chamber 80 and the target material (e.g. the fibrous layer 66) in the activation chamber. In a particular aspect, the method and apparatus can be configured to provided a reflected power which is not more than a maximum of about 50% of the power that is delivered to the activation impedance load. The reflected power can alternatively be not more than about 20% of the delivered power, and can optionally be not more than about 10% of the delivered power to provide improved performance. In a desired feature, the reflected power can be substantially zero. The reflected power can alternatively be about 1%, or less, of the delivered power, and can optionally be about 5%, or less, of the delivered power to provide desired benefits. If the reflected power is too high, inadequate levels of energy are being absorbed by the constituent components of the fibrous layer and the power being directed into the fibrous layer is being inefficiently utilized.

In a particular aspect, the method and apparatus can be configured to provide a Q-factor of at least a minimum of about 200. The Q-factor can alternatively be at least about 5,000, and can optionally be at least about 10,000 to provide further improved performance. In a further feature, the Q-factor can up to about 20,000, or more. If the Q-factor is too low, inadequate electrical field strengths are provided to the constituent components of the fibrous layer. The Q-factor can be determined by the following formula (which may be found in the book entitled *Industrial Microwave Heating* by R. C. Metaxas and R. J. Meredith, published by Peter Peregrinus, Limited, located in London, England, copyright 1983, reprinted 1993):

$$Q\text{-factor} = f_0/\Delta f;$$

where:

$f_0$ = intended resonant frequency (typically the frequency produced by the high-frequency energy source), and $\Delta f$ = frequency separation between the half-power points In the determination of the Q-factor, the power absorbed by the fibrous layer is deemed to be the power delivered into the activation chamber 80 to the fibrous layer, minus the reflected power returned from the activation chamber. The peak-power is the power absorbed by the fibrous layer when the power is provided at the intended resonant frequency, $f_0$. The half-power points are the frequencies at which the power absorbed by the fibrous layer falls to one-half of the peak-power.

For example, a suitable measuring system can include an HP8720D Dielectric Probe, and a model HP8714C Network Analyzer, both available from Agilent Technologies, a business having offices located at Brookfield, Wis., U.S.A. A suitable procedure for determining the Q-factor is described in the User's Manual dated 1998, part number 08712-90056. Substantially equivalent devices and procedures may also be employed.

In another aspect, the activation chamber 80 can have a configuration that can be selectively tuned to operatively "match" the load impedance produced by the presence of the target material (e.g. fibrous layer 66) in the activation chamber. The tuning of the activation chamber can, for example, be provided by any of the techniques that are useful for "tuning" microwave devices. Such techniques can include configuring the activation chamber to have a selectively variable geometry, changing the size and/or shape of a wave-guide aperture, employing adjustable impedance components (e.g. stub tuners), employing a split-shell movement of the activation chamber, employing a variable frequency energy source that can be adjusted to change the frequency of the energy delivered to the activation chamber, or employing like techniques, as well as employing combinations thereof. The variable geometry of the activation chamber can, for example, be provided by a selected moving of either or both of the end walls 128 to adjust the distance therebetween.

Figure 15:
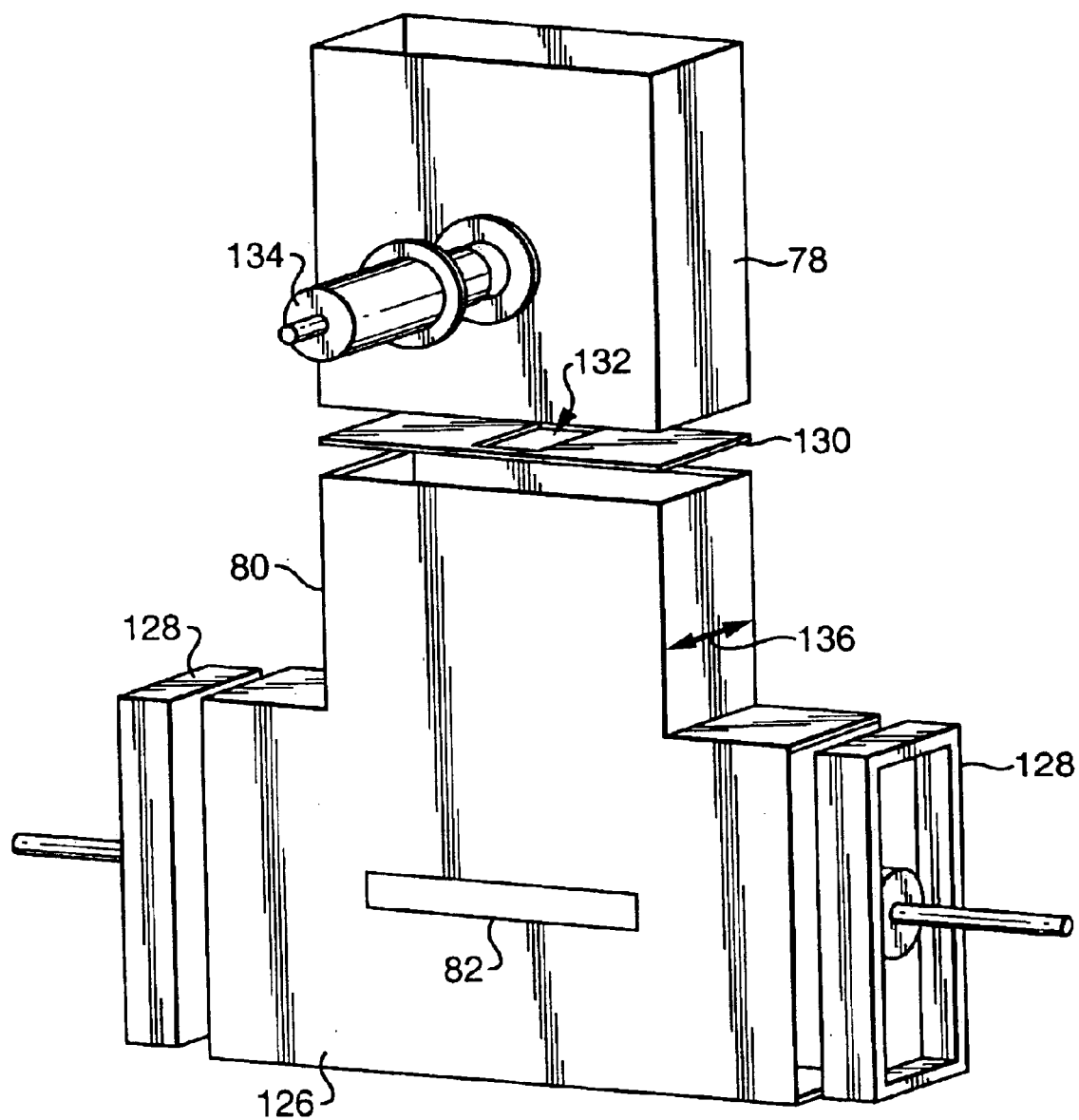
FIG. 15 representatively shows a perspective, exploded view of an adjustable activation chamber that can be selectively tuned.

As representatively shown in FIGS. 15 through 17 and 18A, the tuning feature can include an aperture plate 130 having a selectively sized aperture 132 or other opening. The aperture plate may be positioned at or operatively proximate the location at which the wave-guide 78 joins the activation chamber housing 126. The aperture 132 can be suitably configured and sized to adjust the waveform and/or wavelength of the energy being directed into the activation chamber 80. Additionally, a stub tuner 134 may be operatively connected to the wave-guide 78. With reference to FIG. 15, the wave-guide can direct the activation energy into the chamber 80 at a location that is interposed between the two end walls 128. Either or both of the end walls may be movable to provide selectively positionable end-caps, and either or both of the end walls may include a variable impedance device, such as provided by the representatively shown stub tuner 134. Alternatively, one or more stub tuners 134 may be positioned at other operative locations in the activation chamber 80.

Figure 16:
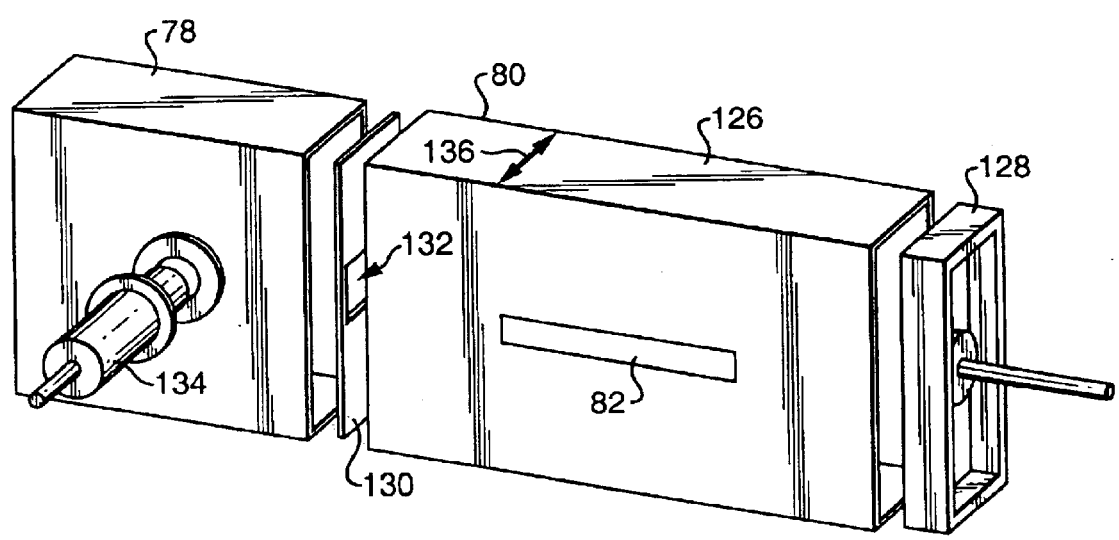
FIG. 16 representatively shows a perspective, exploded view of alternative configuration of an activation chamber that can selectively tuned.

With reference to FIG. 16, the wave-guide 78 may be arranged to deliver the activation energy into one end of the activation chamber 80. Additionally, the end wall 128 at the opposite end of the activation chamber may be selectively movable to adjust the distance between the aperture plate 130 and the end wall 128.

Figure 17:
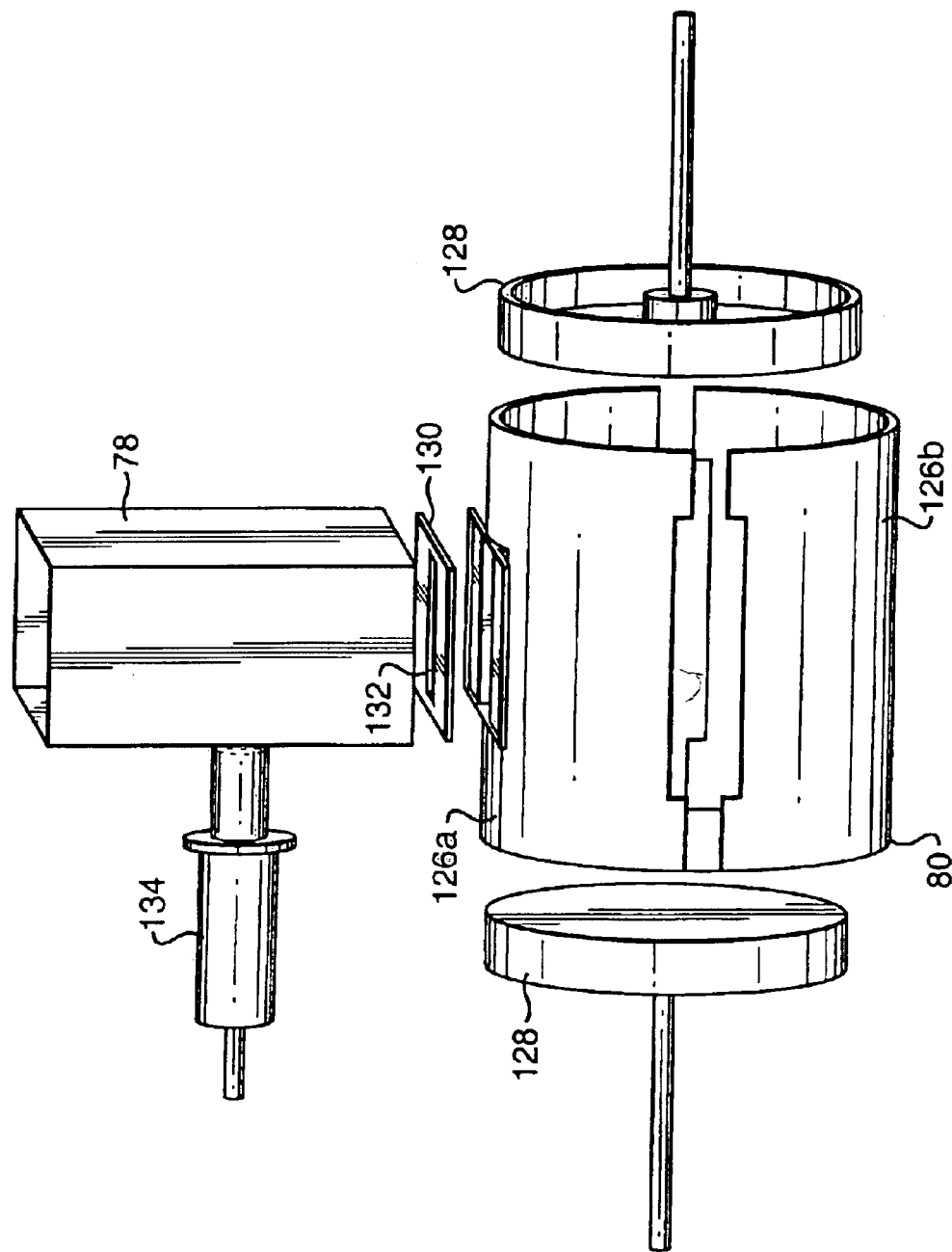
FIG. 17 representatively shows a perspective, exploded view of another configuration of an activation chamber that can be selectively tuned.

With reference to FIG. 17, the activation chamber may have a housing that is non-rectilinear. In a further feature, the rectilinear or non-rectilinear housing 126 may be divided to provide operatively movable split portions 126a and 126b. The chamber split-portions can be selectively postionable to adjust the size and shape of the activation chamber. As representatively shown, either or both of the end walls 128 movable to provide selectively positionable end-caps, and either or both of the end walls may include a variable impedance device, such as provided by the representatively shown stub tuner 134. Alternatively, one or more stub tuners 134 may be positioned at other operative locations in the activation chamber 80.

To tune the activation chamber, the appointed tuning components are adjusted and varied in a conventional, iterative manner to maximize the power into the load (e.g. the fibrous layer), and to minimize the reflected power. Accordingly, the tuning components can be systematically varied to maximize the power into the load and minimize the reflected power. For example, the reflected power can be detected with a conventional power sensor, and can be displayed on a conventional power meter. The reflected power may, for example, be detected at the location of an isolator. The isolator is a conventional, commercially available device which is employed to protect a magnetron from reflected energy. Typically, the isolator is placed between the magnetron and the wave guide. Suitable power sensors and power meters are available from commercial vendors. For example, a suitable power sensor can be provided by a HP E4412 CW power sensor which is available from Agilent Technologies, a business having offices located in Brookfield, Wis., U.S.A. A suitable power meter can be provided by a HP E4419B power meter, also available from Agilent Technologies.

In the various configurations of the method and apparatus, a properly sized aperture plate 130 and a properly sized aperture 132 can help reduce the amount of variable tuning adjustments needed to accommodate a continuous product. The variable impedance device (e.g. stub tuner 134) can also help to reduce the amount of variable tuning adjustments needed to accommodate the processing of a continuous fibrous web or layer. The variable-position end walls or end caps can allow for easier adjustments to a accommodate a varying load. The split-housing configuration of the activation chamber can help accommodate a fibrous web or layer having a varying thickness.

The activation chamber 80 has a chamber entrance 82 and a chamber exit 84. The activation chamber entrance and exit openings are suitably sized and configured to allow a substantially free passage of the fibrous layer 66 therethrough. Within the activation chamber, the fibrous layer can be subjected to or otherwise exposed to the selected high-frequency electromagnetic energy.

To provide a less abrupt binder activation, the method and apparatus can employ a plurality of more than one activation chamber 80. In particular, the method and apparatus can employ two or more activation chambers 80 (e.g. 80a+ 80b+ . . . ). The plurality of activation chambers can, for example, be arranged in the representatively shown serial array (e.g. FIGS. 18 and 18A).

In the various configurations of the method and apparatus, each of the activation chambers 80 can have a machine-directional length 136 (e.g. FIGS. 14 and 15) which can be at least a minimum of about 20 cm. In other aspects, the activation chamber length 136 can be up to a maximum of about 800 cm, or more. The activation chamber length can alternatively be up to about 400 cm, and can optionally be up to about 200 cm to provide improved effectiveness.

Where the activation system employs a multiplicity of individual activation chambers arranged in series, the total sum of the machine-directional activation lengths (e.g. 136a+136b+ . . . ) provided by the plurality of chambers (e.g. FIG. 18A) can be at least a minimum of about 40 cm. In other aspects, the total of the activation chamber lengths can be up to a maximum of about 3000 cm, or more. The total of the activation chamber lengths can alternatively be up to about 2000 cm, and can optionally be up to about 1000 cm to provide improved effectiveness.

The total residence time within the activation chamber or chambers can provide distinctively efficient activation period. In a particular aspect, the activation period can be at least a minimum of about 0.002 sec. The activation period can alternatively be at least about 0.005 sec, and can optionally be at least about 0.01 sec to provide improved performance. In other aspects, the activation period can be up to a maximum of about 3 sec. The activation period can alternatively be up to about 2 sec, and can optionally be up to about 1.5 sec to provide improved effectiveness.

The binder activation system 104 can be configured to activate the binder-fiber material and operatively provide a plurality of interconnections between the absorbent fibers and binder-fibers that are dispersed within the fibrous layer 66. In a particular arrangement, the microwave energy or other electromagnetic energy in the activation chamber 80 can operatively heat the binder-fibers to a temperature above the melting point of the binder-fiber material. The melted binder-fibers can then adhere or otherwise bond and operatively connect to the absorbent fibers. Additionally, the binder-fibers can operatively adhere or otherwise bond and interconnect with superabsorbent particles that are present within the fibrous layer 66. The method and apparatus can advantageously activate the binder-fibers substantially without heating up the entire mass of the fibrous layer 66. In a particular feature, the binder-fibers can be rapidly activated while substantially avoiding any excessive burning of the fibrous layer.

The heating and melt activation of the binder-fibers can be produced by any operative mechanism that is available in the fibrous layer. For example, the electromagnetic energy (e.g. microwave energy) may heat any water vapor that is present within the fibrous layer 66, and the heated vapor can operatively melt the binder-fibers. In another mechanism, the energy can be absorbed by the binder-fibers and the absorbed energy can operatively heat and melt the binder-fibers.

The activation of the binder-fibers within the activation chamber or chambers 80 can operatively produce a stabilized absorbent web 86. The stabilized layer 86 can have a basis weight which is at least a minimum of about 100 g/m². The stabilized layer basis weight can alternatively be at least about 150 g/m², and can optionally be at least about 200 g/m² to provide improved performance. In other aspects, the stabilized layer basis weight can be up to a maximum of about 2500 g/m², or more. The stabilized layer basis weight can alternatively be up to about 2000 g/m², and can optionally be up to about 1500 g/m² to provide improved effectiveness.

In anther aspect, the stabilized layer 86 can have a distinctive density which is at least a minimum of about 0.01 g/cm³. The stabilized layer density can alternatively be at least about 0.02 g/cm³, and can optionally be at least about 0.03 g/cm³ to provide improved performance. In other aspects, the stabilized layer density can be up to a maximum of about 0.5 g/cm³, or more. The stabilized layer density can alternatively be up to about 0.45 g/cm³, and can optionally be up to about 0.4 g/cm³ to provide improved effectiveness.

In a further aspect, the stabilized layer 86 can have a web strength that can support a peak tensile load which is at least a minimum of about 100 gram per inch of cross-directional width of the stabilized layer (g/inch). The stabilized layer strength can alternatively be at least about 200 g/inch, and can optionally be at least about 500 g/inch to provide improved performance. In other aspects, the stabilized layer strength can be up to a maximum of about 10,000 g/inch, or more. The stabilized layer strength can alternatively be up to about 5000 g/inch, and can optionally be up to about 2000 g/inch to provide improved effectiveness. In determining the strength of the stabilized layer 86, any previously formed, separately provided reinforcing component should be excluded from the determination. Such reinforcing components may, for example, be provided by a scrim, a continuous filament fiber, a yarn, an elastic filament, a tissue, a woven fabric, a nonwoven fabric, an elastic film, a polymer film, a reinforcing substrate, or the like, as well as combinations thereof.

The stabilized layer 86 can be configured to have a strength sufficient to support a peak tensile load which is significantly greater than the peak tensile load that can be supported by the precursor, substantially unbonded, fibrous layer 66. In a particular aspect, the stabilized layer 86 can be configured to have sufficient strength to support a peak tensile load which is at least about 100% greater than the peak tensile load that can be supported by the precursor, substantially unbonded, fibrous layer 66. The stabilized layer can alternatively be configured to support a peak tensile load which is at least about 200% greater than the peak tensile load that can be supported by the precursor, substantially unbonded, fibrous layer. Optionally, the stabilized layer 86 can be configured to support a peak tensile load which is at least about 300% greater than the peak tensile load that can be supported by the precursor, substantially unbonded, fibrous layer 66. The percentage of increase in the supported peak-load can be determined by the formula:

$$100*(F2-F1)/F1;$$

where:
F1=the peak tensile load that can be supported by the precursor, substantially unbonded, fibrous layer 66; and
F2=the peak tensile load that can be supported by the stabilized fibrous layer 86.

The peak load, that can be supported by a fibrous layer or by a stabilized layer, can be determined by employing TAPPI Test Method Number T 494 om-96 entitled "Tensile Properties of Paper and Paperboard" (using constant rate of elongation apparatus) dated 1996. The test sample has a width of 1 inch (2.54 cm), and a length of 6 inch (15.24 cm). The jaws used were INSTRON part number 2712-001 (available from Sintech, Inc., a business having offices in Research Triangle Park, N.C., U.S.A.), and were arranged with an initial separation distance of 5 inch (12.7 cm). The cross-head speed was 12.7 mm/min, and the testing employed a MTS Systems Corp. model RT/1 testing machine controlled by TESTWORKS version 4.0 software, which are available from MTS Systems Corp., a business having office in Eden Prairie, Minn., USA. Substantially equivalent equipment may optionally be employed.

In another feature, the activation chamber 80 can be operatively configured to remove excess condensation of water or other liquid from the activation chamber 80. The system for removing excess liquid can include: a system of drain holes in the activation chamber, a vacuum or forced air flow through the activation chamber 80, an activation chamber that is heated, an activation chamber with a housing having a screen-like or otherwise porous configuration, or the like, as well as combinations thereof. Where the liquid removal system employs an airflow exit conduit, the conduit can include a microwave choke.

To help provide the desired stabilization of the target web, the stabilized web or layer 86 leaving the activation chamber 80 can be selectively cooled or otherwise processed prior to performing further operations on the target web. In particular, the stabilized layer 86 can be cooled prior to a desired debulking operation. The cooling of the stabilized layer 86 can be provided by a cooling system that includes: chilled air, a refrigerated atmosphere, radiant cooling, transvector cooling, ambient air cooling, or the like, as well as combinations thereof. As representatively shown in FIG. 1, the cooling system may include a chilled-air supply hood 138, a vacuum conveyor 140, a blower 142, and a chiller or other refrigeration unit 144. The refrigeration unit can provide a suitable coolant to a heat exchanger 146, and the blower can circulate air through the heat exchanger 146 for cooling. The cooled air can be directed into the chilled hood 138 and onto the stabilized layer 86. The air can then be drawn out of the chilled hood 138 for recirculation through the heat exchanger.

In a particular aspect, the method and apparatus can cool or otherwise process the stabilized layer 86 to a setting temperature which is below the melting temperature of the binder-fiber material. In another aspect, the stabilized layer can be cooled to a temperature of not more than a maximum of 200° C. within a selected setting distance measured from the exit region 84 of the activation chamber 80. In a further feature, the stabilized layer can be cooled to a temperature of not more than a maximum of 150° C. within the selected setting distance. Accordingly, the setting distance can be measured after ending the exposure of the fibrous layer to the high-frequency electromagnetic energy in the activation chamber. In a particular feature, the setting distance can be a minimum of about 0.5 m. The setting distance can alternatively be at least a minimum of abut 0.75 m, and can optionally be at least about 1 m to provide improved performance. In another feature, the setting distance can be a maximum of not more than about 30 m. The setting distance can alternatively be not more than about 20 m, and can optionally be not more than about 10 m to provide improved benefits.

In another aspect, the method and apparatus can cool or otherwise process an incremental portion of the activated web 86 to the desired setting temperature within a distinctive setting period, as determined from the time that the incremental portion of the activated web exits the activation chamber 80. Accordingly, the setting period can be measured after ending the exposure of the fibrous layer to the high-frequency electromagnetic energy in the activation chamber. In a particular feature, the setting period can be a minimum of about 0.05 sec. The setting period can alternatively be at least a minimum of abut 0.075 sec, and can optionally be at least about 0.1 sec to provide improved performance. In another feature, the setting period can be a maximum of not more than about 3 sec. The setting period can alternatively be not more than about 2 sec, and can optionally be not more than about 1 sec to provide improved benefits.

The temperature of the fibrous web or layer can be determined by employing an infrared scanner, such as a model No. LS601RC60 available from Land Infrared, a business having offices located in Bristol, Pa., U.S.A. With this device, the temperature can be determined by aiming the measurement probe at the centerline of the web, and setting up the probe (in accordance with the instruction manual) at a separation distance of 12 inches, as measured perpendicular to the web. Alternatively, a substantially equivalent device may be employed.

After the stabilized layer 86 departs the activation chamber 80, the stabilized layer can be debulked to provide a desired thickness and density. In a desired aspect, the debulking can be conducted after the stabilized layer 86 has been selectively cooled, and as representatively shown, the debulking operation can be provided by a pair of counter-rotating nip rollers 88. The debulking operation can alternatively be provided by a converging conveyor system, indexed platens, elliptical rollers, or the like, as well as combinations thereof.

The debulking or compressing operation can provide a debulked, stabilized layer 110 which has a distinctive thickness. In a particular aspect, the debulked thickness can be a minimum of about 0.5 mm. The debulked thickness can alternatively be at least about 1 mm, and can optionally be at least about 2 mm. In another aspect, the debulked thickness can be up to a maximum of about 25 mm. The debulked thickness can alternatively be up to about 15 mm, and can optionally be up to about 10 mm to provide improved benefits.

In another aspect, the debulked layer 110 can have a density which is at least a minimum of about 0.05 g/cm$^3$. The debulked layer density can alternatively be at least about 0.08 g/cm$^3$, and can optionally be at least about 0.1 g/cm$^3$ to provide improved performance. In further aspects, the debulked layer density can be up to a maximum of about 0.5 g/cm$^3$, or more. The debulked layer density can alternatively be up to about 0.45 g/cm$^3$, and can optionally be up to about 0.4 g/cm$^3$ to provide improved effectiveness.

In optional configurations, the fibrous layer may be cut or otherwise divided to provide a desired lateral shaping of the fibrous layer, and/or to provide a laterally contoured web. The cutting system may, for example, include a die cutter, a water cutter, a rotary knives, reciprocating knives or the like, as well as combinations thereof. The web shaping may be conducted prior to and/or after fibrous layer is subjected to the activation of the binder-fiber with the selected activation system 104. In additional features, the material removed by the shaping operation may be recycled back to the fiberizer 44, or may be recycled back to the binder-fiber feeder 62. The removed material may alternatively be recycled back to the binder-fiber opener 60, and may optionally be recycled back to the binder-fiber metering device 62.

Where the stabilized layer 86 has a substantially continuous machine-directional length, it will be readily apparent that various conventional devices and techniques can be employed to separate the stabilized fibrous layer into predetermined lengths to provide selected laid fibrous articles. For example, the longitudinally extending fibrous layer 86 can be transferred from the take-off conveyor 114 to a transverse severing system. The severing system may, for example, include a die cutter, a water cutter, a rotary knives, reciprocating knives or the like, as well as combinations thereof. A mechanical or electronic sensor mechanism can, for example detect the key notches or other markers within the web 66, and the severing system can operate an actuator which operatively moves a cutting member against selected regions of web 66, thereby transversely severing the web into discrete articles, such as the pads 120. After severing, the discrete fibrous pads 120 can be transported and delivered for further processing operations, as desired.

FIGS. 21 through 24 show representative fibrous articles, which can be formed by the method and apparatus of the invention. The fibrous article is particularly suitable for use in an absorbent article, such as disposable diaper. The airformed fibrous web pad 120 can be formed from the longitudinally extending web 66 by appropriately severing the web 66 transversely into suitable lengths. The fibrous pad 120 can have an appointed, article rear section 124, and an appointed, article front section 122. As mentioned previously, this fibrous pad may feature leg cut-outs along its side margins when the invention employs side-masking members 36 and 36a that are configured to provide contour rings. A key notch can be formed at a selected side edge of each fibrous pad article, and the notch or other operative marker can be employed as a reference point for severing the longitudinally extending fibrous layer into lengths of predetermined dimension.

A longitudinal first region of the fibrous pad 120, such as provided by the pad front section 122, can provide a higher basis weight region 90 of the article relative to a second, lower basis weight region 92 of the pad, such as provided by the rear pad section 124. Where the fibrous pad has shaped, leg cut-outs, the pad may include laterally extending corner segments or "ears". The pad 120 includes a relatively low-basis-weight region and a contiguous, relatively high-basis-weight region. The high-basis-weight region can substantially correspond to a non-separable protrusion from a first surface of the fibrous pad that corresponds to the concavely contoured surface portion of the forming surface 34. The pad 120 can feature a second major surface which can be substantially flat, and can typically correspond to the surface processed by the scarfing roll 46. The pad side surfaces correspond to the side walls provided by side-masking members 36 and 36a. The end surfaces of the pad can correspond to severed edges, or may correspond to the transverse and depth-wise extending, end wall surfaces provided by one or more end-masking members 102.

Figure 21:
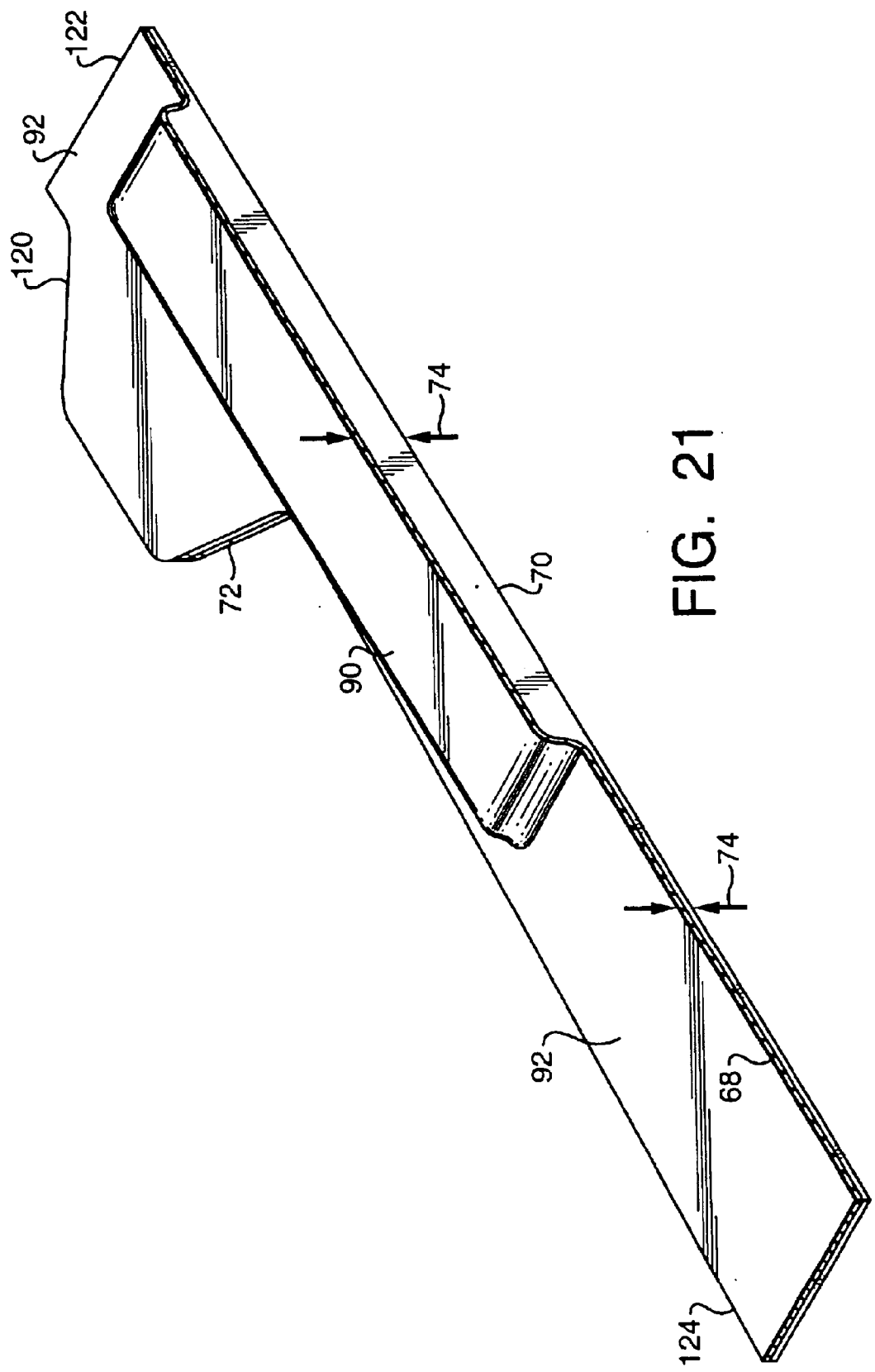
FIG. 21 representatively shows a perspective view of a cross-section through a fibrous layer segment or pad in which the binder-fiber is more heavily concentrated in a fibrous layer stratum that was located relatively closer to and generally adjacent the forming surface employed by the method and apparatus.

With reference to FIG. 21, the method and apparatus can be configured to provide a fibrous web segment or pad 120 in which the binder-fiber is more heavily concentrated in a fibrous web stratum that was located relatively closer to and generally adjacent a forming-surface side 68 of the pad. The forming-surface side is the side that was located relatively closer to and generally adjacent the forming surface employed by the method and apparatus. Such a pad configuration can, for example, be produced by the configurations of the method and apparatus that are representatively shown in FIGS. 10 and 11. Accordingly, the web stratum that was closer to the forming surface, with the relatively higher concentration of binder-fiber, can have a relatively higher strength, as compared to the other portions of the web.

Figure 22:
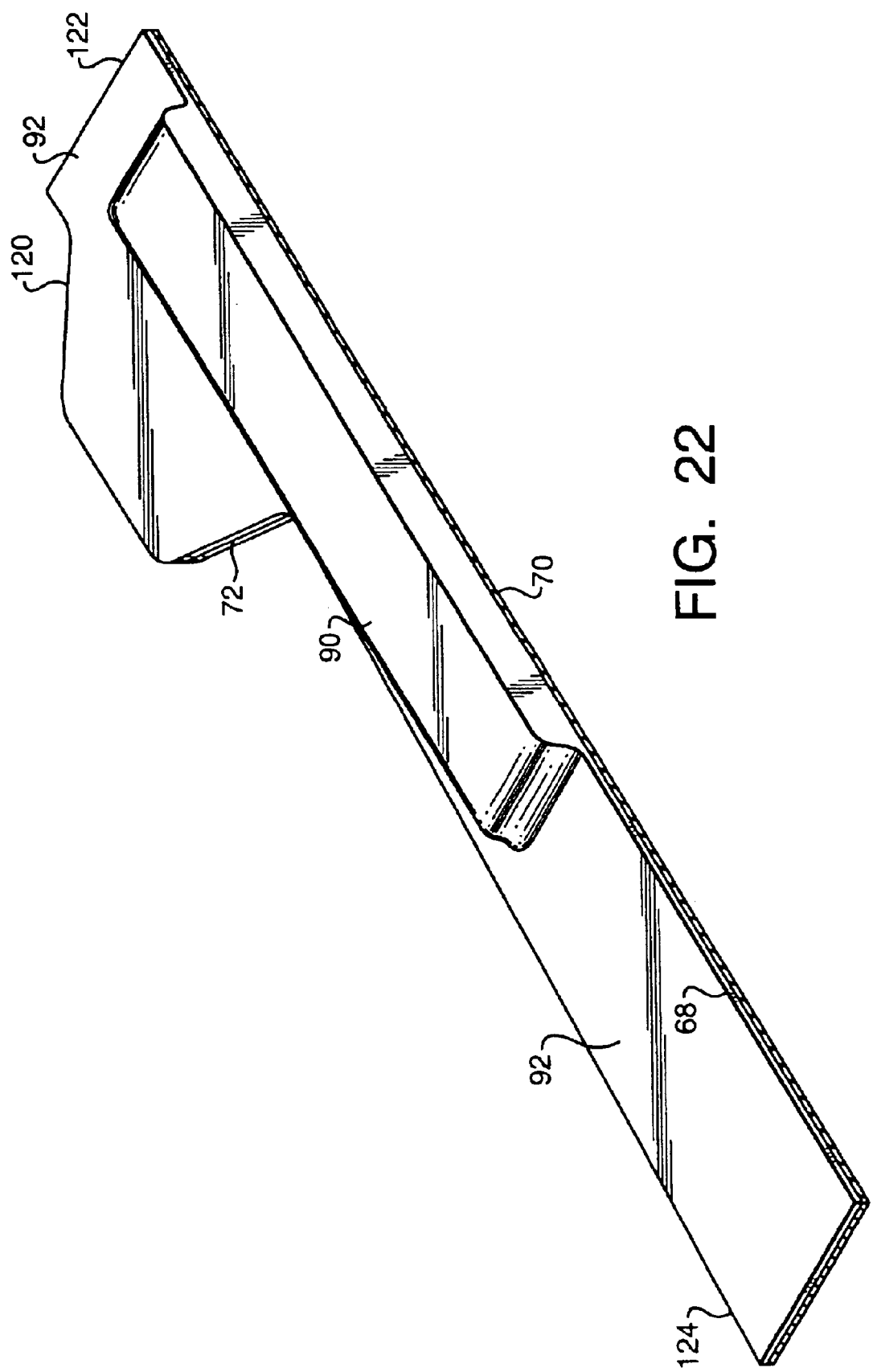
FIG. 22 representatively shows a perspective view of a cross-section through a fibrous layer segment or pad in which the binder-fiber is more heavily concentrated in a fibrous layer stratum that was located relatively farther from the employed forming surface and relatively closer to and generally adjacent a free-surface side of the formed web.
Figure 23:
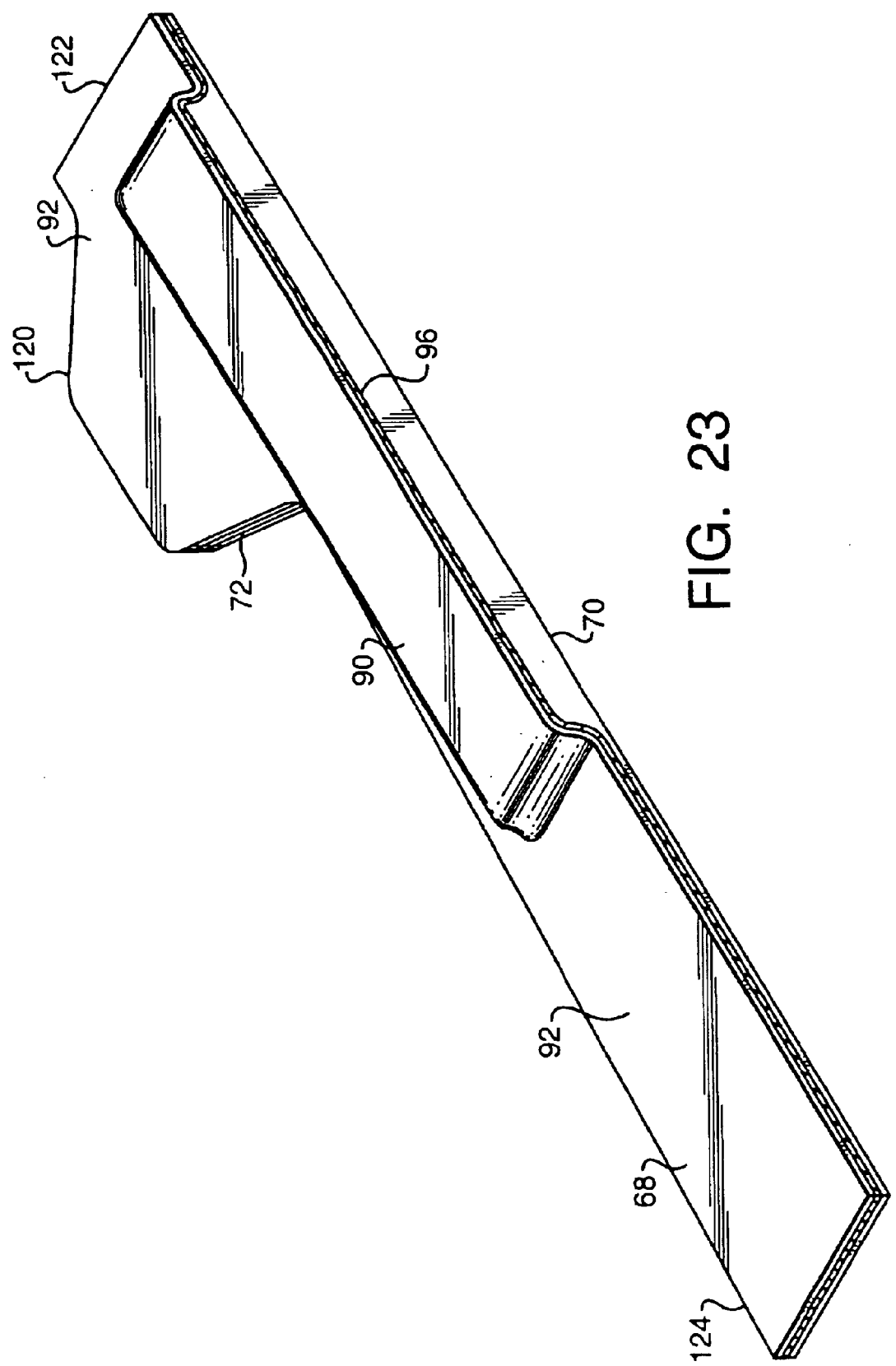
FIG. 23 representatively shows a perspective view of a cross-section through a fibrous layer segment or pad in which the binder-fiber is more heavily concentrated in an intermediate-level fibrous web stratum.
Figure 24:
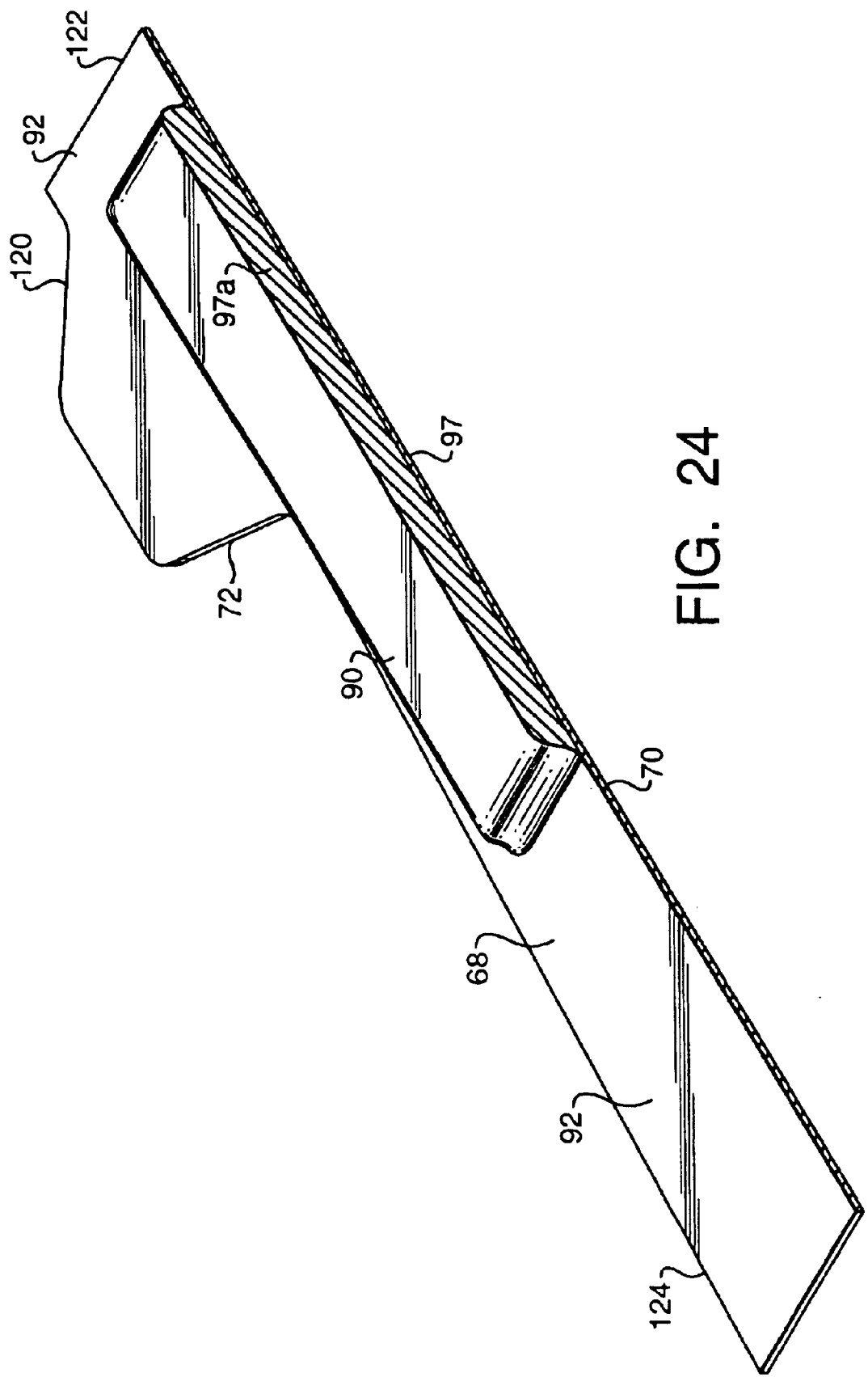
FIG. 24 representatively shows a perspective view of a cross-section through a fibrous layer segment or pad in which a first concentration of binder-fiber is located in a first fibrous web stratum, and a different, second concentration of binder-fiber is located in a second fibrous web stratum.

With reference to FIG. 22, the method and apparatus can be configured to provide a fibrous web segment or pad in which the binder-fiber is more heavily concentrated in a fibrous web stratum that was located relatively farther from the employed forming surface and relatively closer to and generally adjacent a free-surface side 70 of the formed web. Such a pad configuration can, for example, be produced by the configurations of the method and apparatus that are representatively shown in FIG. 13. Accordingly, the web stratum that was farther from the forming surface, with the relatively higher concentration of binder-fiber, can have a relatively higher strength, as compared to the other portions of the web.

It should be readily appreciated that various aspects of the method and apparatus can be further configured to produce other distributions of the binder-fiber through the fibrous web or layer, and to produce web segments or pads having such other distributions of the binder-fiber. As mentioned in the present disclosure, the arrangement representatively shown in FIG. 12 can produce a substantially uniform mixture of the binder-fiber within the web segment or pad. The method and apparatus can alternatively be configured to produce a fibrous web segment or pad in which the binder-fiber is more heavily concentrated in an intermediate-level fibrous web stratum 96 (e.g. FIG. 23), and can optionally be configured to produce a fibrous web segment or pad in which a first concentration of binder-fiber is located in a first fibrous web stratum 97, and a different, second concentration of binder-fiber is located in a second fibrous web stratum 97a (e.g. FIG. 24).

Various transport devices may be employed to move the target work material (e.g. the fibrous layer 66) through the various operations provided by the method and apparatus, and any suitable transport mechanism may be employed. Such transport devices can, for example, be provided by transport rollers, conveyor belts, pneumatic conveyors, vacuum conveyors or the like, as well as combinations thereof.

In the various attachments and securements employed in the constructions of the method and apparatus of the invention, it should be readily apparent that any conventional attachment or securement technique may be employed. Such techniques may, for example, include adhesives, welds, screws, bolts, rivets, pins, latches, clamps or the like, as well as combinations thereof.

Similarly, it should be readily apparent that any conventional material may be employed to construct the various components incorporated into the method and apparatus of the invention. Such materials can include synthetic polymers, fiberglass-resin composites, carbon fiber-resin composites, metallic composites, ceramic composites, and the like, as well as combinations thereof. The materials are typically selected to provide desired levels of strength, durability, ease of manufacture, and ease of maintenance.

Although various illustrative and representative configurations have been described in detail herein, it is to be appreciated that other variants, modifications and arrangements are possible. All of such variations, modifications and arrangements are to be considered as being within the scope of the present invention.

What is claimed is:

1. A method for forming a stabilized airlaid layer, comprising:
    an airforming of a substantially unbonded fibrous layer, which is substantially free of active inter-fiber bonds, said fibrous layer including absorbent fibers arid binder-fibers;
    a moving of said fibrous layer at a fibrous layer speed of at least a minimum of about 0.5 m/sec; and
    an exposing of said fibrous layer to high-frequency electromagnetic energy during an activation period of not more than a maximum of about 3 sec to activate said binder-fibers to provide said stabilized, airlaid layer.

2. A method for forming a stabilized airlaid layer, comprising:
    an airforming of a substantially unbonded fibrous layer, which is substantially free of active inter-fiber bonds, said fibrous layer including substantially unbonded absorbent fibers and substantially unbonded binder-fibers which are substantially unbonded to one another;
    a moving of said fibrous layer at a fibrous layer speed of at least a minimum of about 0.5 m/sec; and
    an exposing of said fibrous layer to high-frequency electromagnetic energy during an activation period of not more than a maximum of about 3 sec to activate said binder-fibers to provide a stabilized, airlaid layer.

3. A method for forming an airlaid layer, comprising:
    an airforming of a fibrous layer which includes absorbent fibers and binder-fibers, said absorbent fibers and binder-fibers arranged substantially free of active inter-fiber bonds, and said fibrous layer formed with a cross-directional width that substantially corresponds to a single-article dimension;
    a moving of said fibrous layer at a fibrous layer speed of at least a minimum of about 0.5 m/sec;
    an exposing of said fibrous layer to high-frequency electromagnetic energy during an activation period of not more than a maximum of about 3 sec to activate said binder-fibers to provide a stabilized, airlaid layer.

4. A method for forming an airlaid layer, comprising:
    an airforming of a fibrous layer which includes absorbent fibers and binder-fibers;
    a moving of said fibrous layer at a fibrous layer speed of at least a minimum of about 0.5 m/sec;

an exposing of said fibrous layer to high-frequency electromagnetic energy in a tuned activation chamber during an activation period of not more than a maximum or about 3 sec to thereby activate said binder-fibers to provide a stabilized, airlaid layer, said activation chamber operatively tuned to provide a reflected power value of not more than a maximum of about 50%.

5. A method for forming an airlaid layer, comprising:
an airforming of a fibrous layer which includes absorbent fibers and binder-fibers, said absorbent fibers and binder-fibers arranged substantially free of active inter-fiber bonds;
a moving of said fibrous layer at a fibrous layer speed of at least a minimum of about 0.5 m/sec;
an exposing of said fibrous layer to high-frequency electromagnetic energy in a tuned activation chamber to activate said binder-fibers and thereby provide a stabilized, airlaid layer, said activation chamber operatively tuned to provide a Q-factor of at least a minimum of about 200.

6. A method as recited in claim 5, wherein said exposing of said fibrous layer to high-frequency electromagnetic energy is configured to occur over an activation period of not more than a maximum of about 3 sec.

7. A method as recited in claim 5, wherein said exposing of said fibrous layer to high-frequency electromagnetic energy is configured to provide a reflected power of not more than about 50%.

8. A method as recited in claim 5, further including a configuring of said binder-fibers to have a dielectric loss factor which is greater than a dielectric loss factor of said absorbent fibers.

9. A method for forming an airlaid layer, comprising:
an airforming of a fibrous layer which includes absorbent fibers and binder-fibers, said absorbent fibers and binder-fibers substantially free of active inter-fiber bonds, and said fibrous layer formed with a non-constant, contoured basis weight;
a moving of said fibrous layer at a fibrous layer speed of at least a minimum of about 0.5 m/sec;
an exposing of said binder-fibers to high-frequency electromagnetic energy during an activation period of not more than a maximum of about 3 sec to provide a stabilized, airlaid layer.

10. A method for forming a stabilized airlaid layer, comprising:
a providing of absorbent fibers with a fiberizer;
a directing of said absorbent fibers into a forming chamber;
an introducing of binder-fibers into said forming chamber by directing said binder-fibers into said forming chamber at an binder-fiber inlet location that is closely adjacent said fiberizer;
an airforming of a fibrous layer which includes a mixture of said absorbent fibers and binder-fibers, said absorbent fibers and binder-fibers arranged substantially free of active inter-fiber bonds;
a moving of said fibrous layer at a fibrous layer speed of at least, minimum of about 0.5 m/sec;
an exposing of said fibrous layer to high-frequency electromagnetic energy during an activation period of not more than a maximum of about 3 sec to thereby activate said binder-fibers to provide said stabilized, airlaid layer.

11. A method as recited in claim 10, wherein said introducing of binder-fibers into said forming chamber includes a directing of binder-fibers into said fiberizer.

12. A method as recited in claim 10, further including a directing of superabsorbent material into said forming chamber to mix with said absorbent fibers and binder-fibers.

13. A method as recited in claim 10, wherein said binder-fibers have been configured to have a dielectric loss factor of at least about 0.05.

14. A method for forming a stabilized airlaid layer, comprising:
an airforming of a fibrous layer which includes absorbent fibers and binder-fibers, said absorbent fibers and binder-fibers arranged substantially free of active inter-fiber bonds, said binder-fibers having a fiber length of at least a minimum of about 6 mm;
a moving of said fibrous layer at a fibrous layer speed of at least a minimum of about 0.5 m/sec; and
an exposing of said fibrous layer to high-frequency electromagnetic energy during an activation period of not more than a maximum of about 3 sec to activate said binder-fibers to provide said stabilized, airlaid layer.

15. A method for forming an airlaid layer, comprising:
an airforming of a fibrous layer which includes absorbent fibers and binder-fibers;
a moving of said fibrous layer at a fibrous layer speed of at least a minimum of about 0.5 m/sec;
an exposing of said fibrous layer to high-frequency electromagnetic energy during an activation period of not more than a maximum of about 3 sec to activate said binder-fibers to provide a stabilized, airlaid layer;
a presenting of said stabilized layer at a setting temperature of not more than about 200° C. which is provided within a period of not more than about 3 sec after an ending of said exposing of the fibrous layer to high-frequency electromagnetic energy;
a debulking of said stabilized layer to increase a density thereof, said debulking occurring at a temperature that is not higher than said setting temperature.

16. A method for forming an airlaid layer, comprising:
an airforming of a fibrous layer which includes absorbent fibers and binder-fibers, said absorbent fibers and binder-fibers arranged substantially free of active inter-fiber bonds said fibrous layer having an average density of not more than a maximum of about 0.1 g/cm$^3$, and an average basis weight of at least about 100 g/cm$^2$;
an exposing of said fibrous layer to high-frequency electromagnetic energy during an activation period of not more than a maximum of about 3 sec to activate said binder-fibers arid provide a stabilized, airlaid layer, said electromagnetic energy having a frequency of at least about 0.3 MHz;
a debulking of said stabilized layer to provide a debulked, stabilized layer having a relatively greater average density.

17. A method for forming an airlaid layer, comprising:
a providing of absorbent fibers from a fiberizer into a forming chamber;
an introducing of a metered amount of binder-fibers into said forming chamber by directing said binder-fibers into said forming chamber at an binder-fiber inlet location that is closely adjacent said fiberizer;
an airforming of an fibrous layer within said forming chamber, said fibrous layer including a mixture of said absorbent fibers and said binder-fibers, said absorbent fibers and binder-fibers arranged substantially free of active inter-fiber bonds;

a scarfing of said fibrous layer to provide
   an average fibrous layer density of not more than a maximum of about 0.1 g/cm³, and
   a fibrous layer, basis weight of at least about 100 g/m²;
a moving of said fibrous layer at a fibrous layer speed of at least a minimum of about 0.5 m/sec;
an exposing of said fibrous layer to high-frequency electromagnetic energy during an activation period of not more than a maximum of about 3 sec to thereby activate said binder-fibers and provide a stabilized, airlaid layer, said electromagnetic energy having a frequency of at least about 0.3 MHz;
a debulking of said stabilized layer to provide a debulked, stabilized layer having a relatively greater average density.

18. A method for forming an airlaid layer, comprising:
an airforming of a fibrous layer which includes absorbent fibers and binder-fibers, said absorbent fibers and binder-fibers arranged substantially free of active inter-fiber bonds;
a moving of said fibrous layer at a fibrous layer speed of at least a minimum of about 0.5 m/sec;
an exposing of said fibrous layer to high-frequency electromagnetic energy in a tuned activation chamber during an activation period of not more than a maximum of about 3 sec to activate said binder-fibers to provide a stabilized, airlaid layer, said electromagnetic energy having a frequency of at least about 0.3 MHz;
a tuning of said activation chamber to provide a Q-factor of at least about 200 when activating said binder-fibers, said tuning employing a variable geometry activation chamber.

19. A method for forming an airlaid layer, comprising:
a providing of absorbent fibers with a fiberizer,
a directing of said absorbent fibers into a forming chamber;
an introducing of a metered amount of binder-fibers into said forming chamber by directing said binder-fibers into said forming chamber at an binder-fiber inlet location that is closely adjacent said fiberizer, said metered amount of binder-fibers arranged to provide not more than about 30 wt % of said stabilized airlaid layer;
an airforming of a fibrous layer within said forming chamber, said fibrous layer including a mixture of said absorbent fibers and said binder-fibers, said absorbent fibers and binder-fibers arranged substantially free of active inter-fiber bonds, and said fibrous layer formed with a cross-directional width that substantially corresponds to a selected single-article dimension;
a scarfing of said fibrous layer to provide at least a portion of said fibrous layer with a basis weight of at least about 100 g/m2;
a moving of said fibrous layer to provide a fibrous layer speed of at least a minimum of about 0.5 m/sec;
an exposing of said fibrous layer to high-frequency electromagnetic energy within a tuned activation chamber during an activation period of not more than a maximum of about 3 sec to activate said binder-fibers to provide a stabilized, airlaid layer, said electromagnetic energy having a frequency of at least about 0.3 MHz;
a tuning of said activation chamber to provide Q-factor of at least about 200 when activating said binder-fibers, said tuning employing a variable geometry activation chamber and a variable impedance; and
a debulking of said stabilized layer to provide a debulked, stabilized layer having an average density of at least a minimum of about 0.05 g/cm³.

20. A method as recited in claim 19, further including a tuning of said activation chamber to provide a reflected power of not more than about 50%.

* * * * *

UNITED STATES PATENT AND TRADEMARK OFFICE
Certificate

Patent No. 6,846,448 B2                                    Patented: January 25, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Timothy James Rymer, Appleton, WI (US); Michael Barth Venturino, Appleton, WI (US); Mark Scott Lancaster, Neenah, WI (US); Robert Eugene Vogt, Neenah, WI (US); Dennis John DeGroot, Appleton, WI (US); Michael Joseph Garvey, Appleton, WI (US); James Alvin Boldra, Menasha, WI (US); Frank Paul Abuto, Duluth, GA (US); Fung-jou Chen, Appleton, WI (US); and Jeffrey Dean Lindsay, Appleton, WI (US).

Signed and Sealed this Eighth Day of April 2008.

YOGENDRA N. GUPTA
*Supervisory Patent Examiner*
Art Unit 1791